(12) United States Patent
Edgell et al.

(10) Patent No.: US 12,412,655 B2
(45) Date of Patent: Sep. 9, 2025

(54) INVENTORY MANAGEMENT OF PORTABLE MEDICAL TREATMENT AND GUIDANCE APPARATUSES

(71) Applicant: ZOLL Medical Corporation, Chelmsford, MA (US)

(72) Inventors: Kristopher M. Edgell, Shreveport, LA (US); Gary A. Freeman, Waltham, MA (US); Matthew J. Grey, Fairport, NY (US); John P. Pierson, Tewksbury, MA (US); Paolo Giacometti, Chelmsford, MA (US); Denise L. Angwin, Chelmsford, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 170 days.

(21) Appl. No.: 18/027,547

(22) PCT Filed: Dec. 9, 2021

(86) PCT No.: PCT/US2021/062591
§ 371 (c)(1),
(2) Date: Oct. 13, 2023

(87) PCT Pub. No.: WO2022/125766
PCT Pub. Date: Jun. 16, 2022

(65) Prior Publication Data
US 2024/0006057 A1  Jan. 4, 2024

Related U.S. Application Data

(60) Provisional application No. 63/123,977, filed on Dec. 10, 2020.

(51) Int. Cl.
*G16H 40/20* (2018.01)
*A61B 90/96* (2016.01)
(Continued)

(52) U.S. Cl.
CPC ............. *G16H 40/20* (2018.01); *A61B 90/96* (2016.02); *A61B 90/98* (2016.02); *A61F 17/00* (2013.01); *A61N 1/046* (2013.01)

(58) Field of Classification Search
CPC ........ G16H 40/20; G16H 20/30; G16H 20/40; G16H 40/40; G16H 40/63; A61B 90/96; A61B 90/98; A61F 17/00; A61N 1/046
See application file for complete search history.

(56) References Cited

U.S. PATENT DOCUMENTS

| 2017/0340221 A1 | 11/2017 | Cronin et al. |
| 2020/0375825 A1 | 12/2020 | Gerstner et al. |
| 2022/0181019 A1* | 6/2022 | Ukrainksy ............. A61B 50/20 |

FOREIGN PATENT DOCUMENTS

| CN | 210844587 U | * | 6/2020 |
| WO | 2019112844 A1 | | 6/2019 |
| WO | 2022125766 A1 | | 6/2022 |

OTHER PUBLICATIONS

Kibira, Deogratias, Y. Tina Lee, and Mehdi Dadfarnia. "Modeling for optimal ambulance patient compartment layout." Proceedings of the 2012 Spring Simulation Multiconference: Orlando. 2012 (Year: 2012).*

(Continued)

*Primary Examiner* — Linh Giang Le
(74) *Attorney, Agent, or Firm* — Mintz, Levin, Cohn, Ferris, Glovsky and Popeo, P.C.

(57) ABSTRACT

In one aspect, a portable medical treatment and guidance apparatus for interactively assisting a user in treating a patient is provided. The apparatus can include: a housing having at least one compartment; a plurality of medical supplies housed within the at least one compartment; a user interface configured to provide an interactive query flow for assisting the user in providing medical treatment; at least one sensor adapted to detect removal of at least one medical (Continued)

item of the plurality of medical supplies; and at least one processor and memory mechanically coupled to the housing and communicatively coupled to the user interface, the at least one sensor, and communications circuitry.

34 Claims, 30 Drawing Sheets

(51) Int. Cl.
    *A61B 90/98*     (2016.01)
    *A61F 17/00*     (2006.01)
    *A61N 1/04*     (2006.01)

(56)     References Cited

OTHER PUBLICATIONS

International Search Report and Written Opinion for International Patent Application No. PCT/US2021/062591 mailed Apr. 25, 2022.

\* cited by examiner

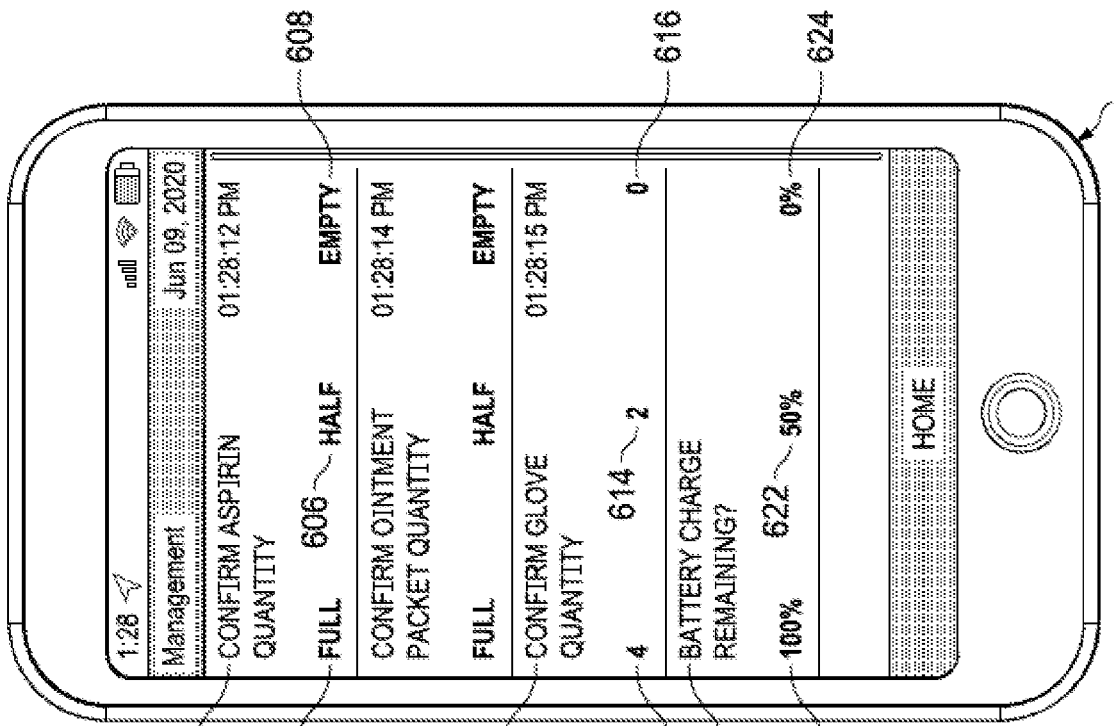
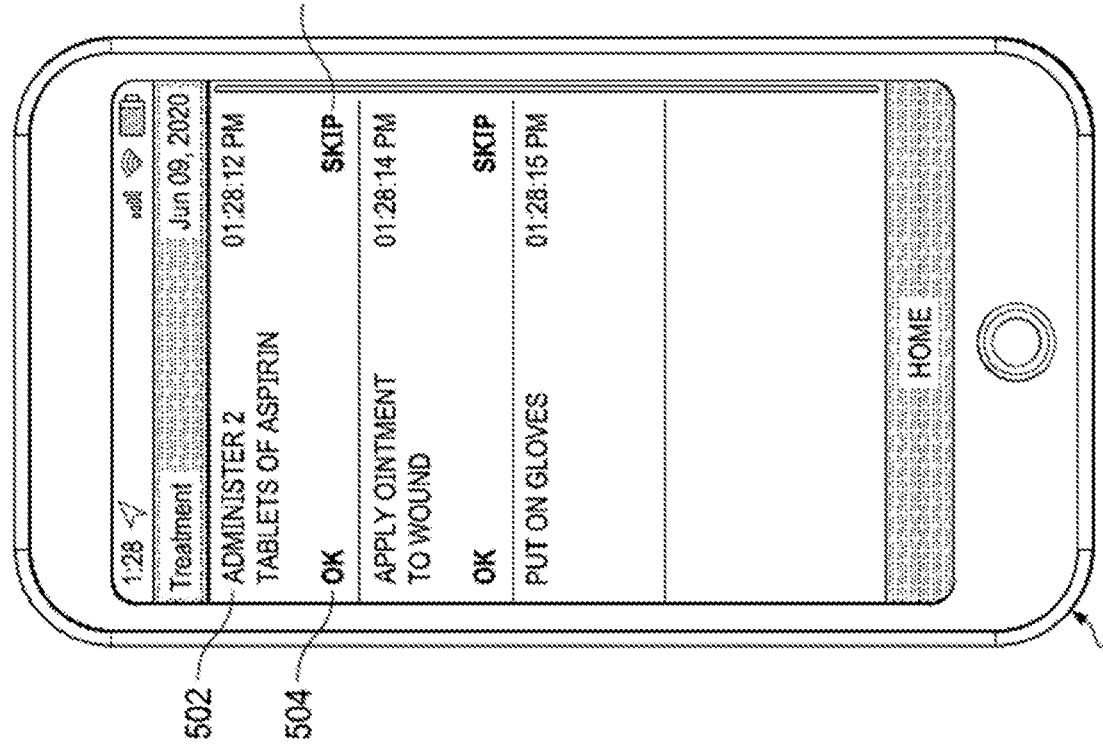

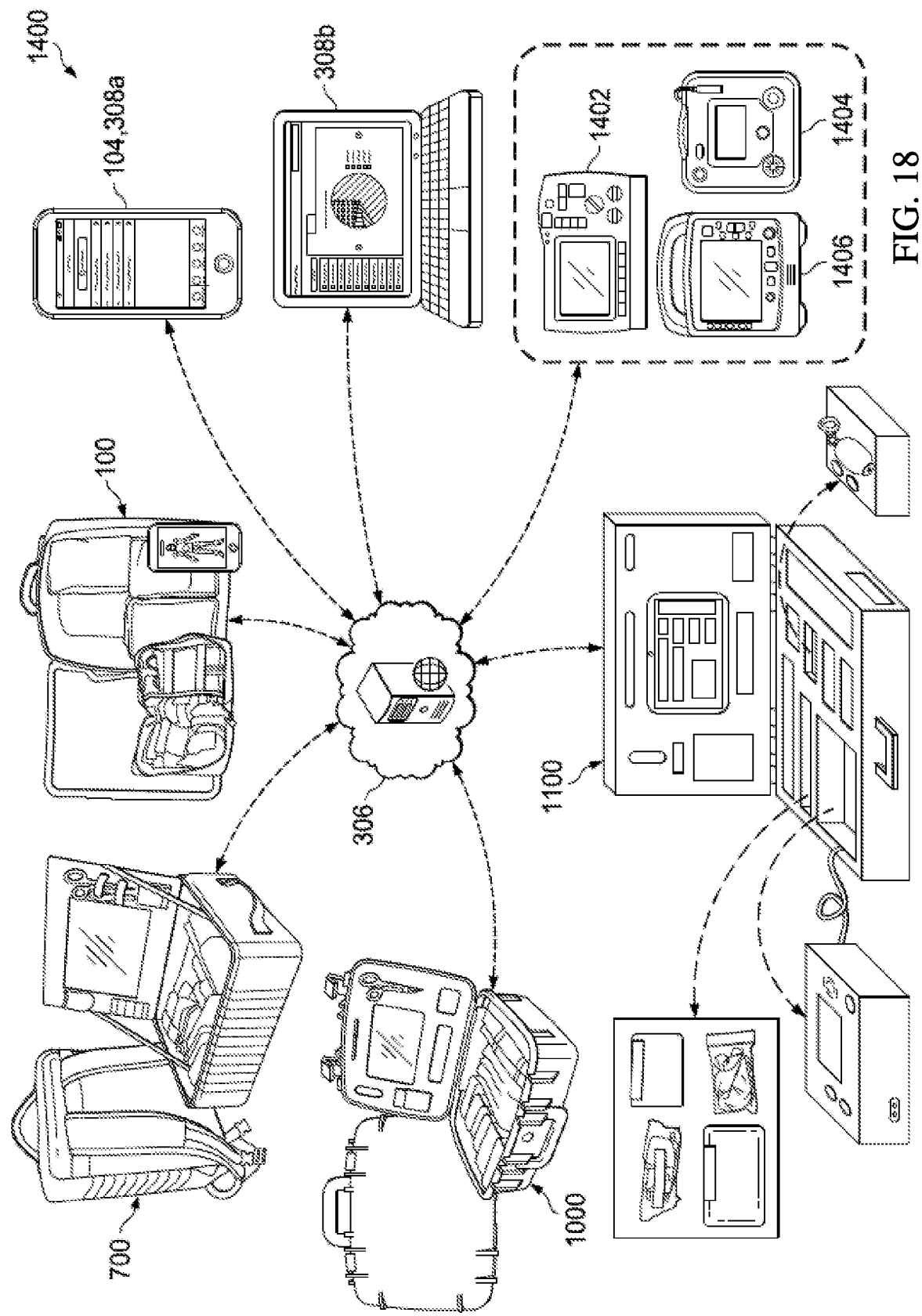

ZOLL® Portable Medical Treatment and Guidance Apparatus Management System

Kit Status | Search | Setup | Reports | Help | Log Out

Kit Type: ALL  Location: ALL
Last Checked: ALL  Status: ALL

| Kit | Serial Number | Last Checked | Summary | Location |
|---|---|---|---|---|
| | AR140212001 | One minute ago | Fully Stocked Ready | Floor 7, Hallway |
| | AR11123333 | One minute ago | Missing 1 Item Needs Inspection | Floor 6, Hallway |
| | AR120039818 | 3 hours ago | Low Battery Missing 2 Items Needs Inspection | Floor 1, Reception Area |
| | AX15A008888 | 5 months ago | Please confirm status Needs Inspection | Floor 3, Elevator Area |
| | AX15A000555 | Never | Please initialize unit Needs Inspection | Unknown |
| | 03026015 | 7/7/2015 5:01:06 AM | Last Self-Check: OK Ready | Floor 3, Hallway |

FIG. 20A

INVENTORY MANAGEMENT OF PORTABLE MEDICAL TREATMENT AND GUIDANCE APPARATUSES

CROSS REFERENCE

The present application claims priority to and is the 35 U.S.C. 371 United States National Phase application based on International Patent Application No. PCT/US21/62591, filed on Dec. 9, 2021, entitled "INVENTORY MANAGEMENT OF PORTABLE MEDICAL TREATMENT AND GUIDANCE APPARATUSES," which claims priority to U.S. Application No. 63/123,977 entitled "Inventory Management Of Portable Medical Treatment And Guidance Apparatuses" filed Dec. 10, 2020, which are hereby incorporated by reference in their entireties.

FIELD

The present disclosure relates to portable medical treatment systems, apparatuses, and processes and management systems for portable medical treatment systems that provide interactive guidance in administering medical treatment.

BACKGROUND

Various different types of medical first aid kits exist to supply first aid to an injured person. Some such first aid kits also provide written and/or audible instructions for how to treat patients, using the medical supplies contained within the first aid kits. First aid kits may be stored at places where people congregate and therefore medical emergencies are likely to occur (e.g., at workplaces, stores, and schools). In an emergency, a caregiver may locate a portable first aid kit and carry the portable first aid kit to a location of a patient. The caregiver may use the supplies in the portable first aid kit to treat one or more medical emergencies from which the patient may be suffering.

SUMMARY

In one aspect, a portable medical treatment and guidance apparatus for interactively assisting a user in treating a patient is provided. The apparatus can include: a housing having at least one compartment; a plurality of medical supplies housed within the at least one compartment; a user interface configured to provide an interactive query flow for assisting the user in providing medical treatment; at least one sensor adapted to detect removal of at least one medical item of the plurality of medical supplies; and at least one processor and memory mechanically coupled to the housing and communicatively coupled to the user interface, the at least one sensor, and communications circuitry. The at least one processor and memory can be configured to: present via the user interface at least one inquiry as part of the interactive query flow, receive at least one user input via the user interface in response to the at least one inquiry, present via the user interface instructions for administering medical treatment based on the at least one user input, determine whether the at least one sensor has detected removal of the at least one medical item, and transmit an output signal based on the detected removal of the at least one medical item to provide a status indication regarding the portable medical treatment and guidance apparatus.

In some implementations, the at least one processor and memory are further configured to present via the user interface instructions for administering medical treatment based on the detected removal of the at least one medical item.

In some implementations, the instructions for administering medical treatment involve one or more steps for using the at least one medical item.

In some implementations, the status indication regarding the portable medical treatment and guidance apparatus identifies an inventory of the plurality of medical supplies.

In some implementations, the status indication regarding the portable medical treatment and guidance apparatus identifies an expiration date of the plurality of medical supplies.

In some implementations, the at least one processor and memory are further configured to receive the instructions from the at least one medical item.

In some implementations, the at least one processor and memory are further configured to control an operation of the at least one medical item.

In some implementations, the at least one processor and memory are further configured to receive remote control information regarding remote control of an operation of the at least one medical item.

In some implementations, the at least one processor and memory are further configured to receive remote control information regarding remote control of the at least one medical item.

In some implementations, the at least one processor and memory are further configured to receive a status indication regarding the at least one medical item.

In some implementations, the at least one processor and memory are further configured to transmit a status indication regarding the at least one medical item. The status indication regarding the at least one medical item can identify a readiness status of whether the at least one medical item is ready to be used in an emergency. The status indication regarding the at least one medical item can identify a battery charge level of a battery of the at least one medical item. The status indication regarding the at least one medical item can identify an expiration date of the at least one medical item.

In some implementations, the at least one processor and memory are further configured to receive a self-diagnostic signal indicating that a self-diagnostic test of the at least one medical item is required. The self-diagnostic test can include ensuring a battery level of the at least one medical item is above a threshold, ensuring an expiration date of the at least one medical item has not occurred, and/or ensuring the at least one medical item is present in the portable medical treatment and guidance apparatus.

In some implementations, the at least one processor and memory are further configured to determine when a self-diagnostic test of the at least one medical item is required.

In some implementations, the at least one processor and memory are further configured to transmit a self-diagnostic signal indicating that a self-diagnostic test of the at least one medical item is required.

In some implementations, the at least one processor and memory are further configured to transmit a self-diagnostic signal to the at least one medical item to initiate a self-diagnostic test of the at least one medical item.

In some implementations, the at least one processor and memory are further configured to determine when a component of the at least one medical item is missing based on a result of a self-diagnostic test and the at least one sensor.

In some implementations, the at least one processor and memory are further configured to present instructions to use a spare at least one medical item to replace a functionality of the at least one medical item that has failed a self-diagnostic test.

In some implementations, the at least one processor and memory are further configured to search for a nearby spare at least one medical item matching a functionality of the at least one medical item. The at least one processor and memory can be further configured to determine whether the nearby spare at least one medical item is ready for use. The at least one processor and memory can be further configured to present a notification that the nearby spare at least one medical item is nearby and ready for use. The at least one processor and memory can be further configured to present directions for navigating to the nearby spare at least one medical item.

In some implementations, the at least one processor and memory are further configured to determine when a component of the at least one medical item has failed a self-diagnostic test based on a result of the self-diagnostic test. The at least one processor and memory can be further configured to determine identifying information of the component of the at least one medical item that has failed the self-diagnostic test. The at least one processor and memory can be further configured to present the determined identifying information of the component to the user interface. The at least one processor and memory can be further configured to present repair instructions for the component to the user interface. The repair instructions can include instructions to partially disassemble the at least one medical item.

In some implementations, the portable medical treatment and guidance apparatus includes an indicator configured to alert a user that the at least one medical item has failed a self-diagnostic test and needs servicing.

In some implementations, the at least one processor and memory are further configured to determine when a component of the at least one medical item has passed a self-diagnostic test based on a result of the self-diagnostic test.

In some implementations, the portable medical treatment and guidance apparatus includes an indicator configured to notify a user when the at least one medical item has passed a self-diagnostic test and is ready for use.

In some implementations, presenting via the user interface includes displaying the instructions on a display integrated into the housing.

In some implementations, presenting via the user interface comprises verbalizing the instructions using a speaker integrated into the housing.

In some implementations, the portable medical treatment and guidance apparatus includes a near-field communication device configured to communicate with an external device. The near-field communication device can be configured to transmit the status indication regarding the portable medical treatment and guidance apparatus to a nearby mobile device.

In some implementations, the at least one sensor is a radio frequency identification (RFID) reader and is configured to receive an RFID signal from the at least one medical item. Each of the at least one compartments may have at least one light associated therewith, and, in response to the interactive query flow indicating that the at least one medical item should be removed from the portable medical treatment and guidance apparatus, the light associated with the compartment in which the at least one medical item is located may illuminate. The at least one medical item that is removed may not be reusable. The at least one medical item that is removed may be reusable, and, in response to the interactive query flow indicating that the at least one medical item that is reusable should be returned to the portable medical treatment and guidance apparatus, the light associated with the compartment in which the at least one medical item should be located may illuminate.

In some implementations, the at least one sensor is an optical sensor.

In some implementations, the plurality of medical supplies include electrodes for electrotherapy treatment.

In some implementations, the plurality of medical supplies include a resuscitation treatment. In some implementations, the plurality of medical supplies include a resuscitation treatment protocol corresponding to electrotherapy treatment.

In another aspect, a medical treatment and guidance apparatus system is provided. The apparatus can include: a housing having at least one compartment; a plurality of medical supplies housed within the at least one compartment; a user interface configured to provide an interactive query flow for assisting a user in providing medical treatment; and a mobile computing device including: at least one camera; a storage device storing processor-executable instructions; and at least one data processor communicatively coupled to the storage device and the at least one camera, in which upon execution of the processor-executable instructions by the at least one data processor. The at least one data processor can be configured to: determine, based at least in part on information provided by the at least one camera, first identifying information of the medical treatment and guidance apparatus system; determine, based at least in part on information provided by the at least one camera, second identifying information of at least one medical item of the plurality of medical supplies; generate, based at least in part on the first identifying information and the second identifying information, a report representing an inventory of the medical treatment and guidance apparatus system; and transmit the generated report to a server associated with a database for managing an inventory of a plurality of medical treatment and guidance apparatus systems.

In some implementations, the at least one data processor is configured to: present via the user interface at least one inquiry as part of the interactive query flow, receive at least one user input via the user interface in response to the at least one inquiry, and present via the user interface instructions for administering medical treatment based on the at least one user input, wherein the generated report includes the user interface instructions and the at least one user input.

In some implementations, the at least one data processor is configured to: receive via the user interface a confirmation that the at least one medical item was used as part of providing the medical treatment, and wherein the generated report includes the confirmation.

In some implementations, the at least one data processor is configured to: present via the user interface instructions for administering a dosage quantity as part of the medical treatment, receive via the user interface an administered dosage quantity, wherein the generated report includes the administered dosage quantity.

In some implementations, the at least one data processor is configured to: provide instructions regarding using the at least one camera of the mobile computing device to capture an image of the at least one medical item.

In some implementations, the at least one data processor is configured to: receive at least one user input via the user interface, and wherein transmitting the generated report is responsive to receiving the at least one user input.

In some implementations, responsive to receiving the generated report, the server is configured to: provide a notification that the medical treatment has been initiated, update the database, using the first identifying information associated with the housing of the medical treatment and guidance apparatus system, to indicate that the medical treatment and guidance apparatus system has been used, and update the database, using the second identifying information associated with the housing of the medical treatment and guidance apparatus system, to indicate that the at least one medical item has been used.

In some implementations, responsive to receiving the generated report, the server is configured to: initiate a replenishment of the at least one medical item associated with the medical treatment and guidance apparatus system.

In some implementations, determining the first identifying information includes: transmitting information of a first bar code marking of the housing to the server, wherein the information is obtained by the at least one camera of the mobile computing device; instructing the server to perform a query of the database for a match between the first bar code marking and a list of bar code markings associated with respective medical treatment and guidance apparatus systems; and responsive to the querying, retrieving the first identifying information associated with the match.

In some implementations, determining the second identifying information includes: transmitting information of a second bar code marking of the at least one medical item to the server, wherein the information is obtained by the at least one camera of the mobile computing device; instructing the server to perform a query of the database for a match between the second bar code marking and a list of bar code markings associated with respective medical items; and responsive to the querying, retrieving the second identifying information associated with the match.

In some implementations, wherein determining the second identifying information includes: transmitting information representing an image of the at least one medical item; querying the database for a match between the image and a list of images associated with respective medical items; and responsive to the querying, retrieving the second identifying information associated with the match.

In some implementations, the first identifying information includes expiration information of the medical treatment and guidance apparatus system.

In some implementations, the second identifying information includes expiration information of the at least one medical item of the medical treatment and guidance apparatus system.

In some implementations, the mobile computing device is housed within the housing of the medical treatment and guidance apparatus system.

In some implementations, the mobile computing device is detachable from the medical treatment and guidance apparatus system.

In some implementations, the mobile computing device is a standalone device separate from the medical treatment and guidance system, and the user interface is provided on the mobile computing device.

In some implementations, a first bar code marking is attached to the housing of the medical treatment and guidance apparatus system and the first identifying information is associated with the first bar code marking. The first bar code marking may be a QR code. The mobile computing device may be configured to read the first bar code marking, the reading of the first bar code marking may be configured to cause an application to be installed on the mobile computing device, and the application may be configured to provide the interactive query flow. The mobile computing device may be configured to read the first bar code marking, and the reading of the first bar code marking may be configured to cause a browser of the mobile computing device to be directed to a web page configured to provide the interactive query flow.

In some implementations, a second bar code marking is located within the at least one compartment of the medical treatment and guidance apparatus system and the second identifying information is associated with the second bar code. The second bar code marking may not be viewable by the at least one camera when the at least one medical item is housed within the at least one compartment. The second bar code marking may be viewable by the at least one camera when the at least one medical item is removed from the at least one compartment. The second bar code marking may be a QR code.

In some implementations, the at least one data processor is configured to: present via the user interface a map of the medical treatment and guidance apparatus system and a distance of the medical treatment and guidance apparatus system relative to a current position of the mobile computing device. The map can indicate whether the medical treatment and guidance apparatus system is missing the at least one medical item.

In some implementations, the first identifying information includes information on whether the medical treatment and guidance apparatus system has been previously opened.

In some implementations, the first identifying information includes information on whether a battery within the medical treatment and guidance apparatus system is charged.

In some implementations, the first identifying information includes information on whether a first seal is broken.

In some implementations, the server is configured to: perform a query of the database for respective medical treatment and guidance apparatus systems associated with past due inspections; and responsive to the querying, presenting a notification that the respective medical treatment and guidance apparatus systems are associated with the past due inspections.

In some implementations, the at least one data processor is configured to: instruct the server to perform a query of the database for respective medical treatment and guidance apparatus systems associated with past due inspections; and responsive to the querying, presenting a notification that the respective medical treatment and guidance apparatus systems are associated with the past due inspections.

In some implementations, the generated report includes information on a usage of the at least one medical item.

In some implementations, the at least one data processor is configured to: receive via the user interface a confirmation that the at least one medical item was used during the medical treatment.

In some implementations, the at least one data processor is configured to: present via the user interface instructions for administering medical treatment based on the at least one user input, present via the user interface at least one question regarding the provided medical treatment, and receive via the user interface at least one answer regarding the provided medical treatment, wherein the generated report includes the at least one question and at least one answer.

In some implementations, the first identifying information includes information on whether a battery within the medical treatment and guidance apparatus system needs replacement.

In some implementations, the at least one data processor is configured to search for a nearby spare of the at least one medical item matching a functionality of the at least one medical item.

In another aspect, a medical treatment and guidance apparatus management system is provided. The management system can include: a database including status information regarding a plurality of portable medical treatment and guidance apparatuses, wherein the status information includes at least inventory data for each of the plurality of portable medical treatment and guidance apparatuses; a user interface configured to provide a status indication of the plurality of portable medical treatment and guidance apparatuses based on the status information; and at least one processor and memory communicatively coupled with the database and the user interface. The at least one processor and memory can be configured to: receive status updates regarding the plurality of portable medical treatment and guidance apparatuses, update the status information in the database based on the received status updates, and control the user interface to present the status indication of the plurality of portable medical treatment and guidance apparatuses based on the updated status information.

In some implementations, the received status updates identify a presence of at least one medical item housed within at least one of the plurality of portable medical treatment and guidance apparatuses.

In some implementations, the at least one processor and memory are further configured to determine an inventory of at least one medical item housed within at least one of the plurality of portable medical treatment and guidance apparatuses. The at least one processor and memory can be further configured to determine whether the inventory of the at least one medical item is below a threshold. The at least one processor and memory can be further configured to present via the user interface whether the inventory of the at least one medical item is below a threshold.

In some implementations, the at least one processor and memory are further configured to initiate a request to acquire more of at least one medical item.

In some implementations, the at least one processor and memory are further configured to initiate a purchase to acquire more at least one medical item.

In some implementations, the at least one processor and memory are further configured to prioritize a purchase of at least one medical item over another at least one medical item.

In some implementations, the received status updates identify battery levels for at least one medical item housed within at least one of the plurality of portable medical treatment and guidance apparatuses.

In some implementations, the received status updates identify a readiness of at least one medical item housed within at least one of the plurality of portable medical treatment and guidance apparatuses.

In some implementations, the at least one processor and memory are further configured to transmit a request for a self-diagnostic test to be performed by each portable medical treatment and guidance apparatuses of the plurality of portable medical treatment and guidance apparatuses. The self-diagnostic test can include ensuring battery levels for each battery operable medical item within the respective portable medical treatment and guidance apparatus is above a threshold, ensuring an expiration date of each expireable medical item within the respective portable medical treatment and guidance apparatus has not occurred, and/or ensuring each removable medical item is present within the respective portable medical treatment and guidance apparatus.

In some implementations, the at least one processor and memory are further configured to transmit a request for a self-diagnostic test to be performed by at least one medical item housed within at least one of the plurality of portable medical treatment and guidance apparatuses. The self-diagnostic test can include ensuring a battery level of the at least one medical item is above a threshold, ensuring an expiration date of the at least one medical item has not occurred, and/or ensuring the at least one medical item is present in the respective portable medical treatment and guidance apparatus.

In some implementations, the received status updates comprise information related to a self-diagnostic test for at least one medical item housed within at least one of the plurality of portable medical treatment and guidance apparatuses.

In some implementations, the updated status information comprises updating whether a respective portable medical treatment and guidance apparatus has passed a self-diagnostic test.

In some implementations, the at least one processor and memory are further configured to indicate which portable medical treatment and guidance apparatuses of the plurality of portable medical treatment and guidance apparatuses have passed a self-diagnostic test representing that the respective portable medical treatment and guidance apparatus is ready for use.

In some implementations, the medical treatment and guidance apparatus management system includes a mobile device configured to perform the operations of the at least one processor and memory.

In some implementations, the at least one processor and memory are further configured to indicate which portable medical treatment and guidance apparatuses of the plurality of portable medical treatment and guidance apparatuses require attention.

In some implementations, the at least one processor and memory are further configured to indicate a location of each portable medical treatment and guidance apparatuses of the plurality of portable medical treatment and guidance apparatuses that require attention.

In some implementations, the at least one processor and memory are further configured to indicate a date that each portable medical treatment and guidance apparatuses of the plurality of portable medical treatment and guidance apparatuses last passed a self-diagnostic test.

In some implementations, the at least one processor and memory are further configured to indicate a date that each portable medical treatment and guidance apparatuses of the plurality of portable medical treatment and guidance apparatuses was last opened.

In some implementations, the at least one processor and memory are further configured to indicate a date that each portable medical treatment and guidance apparatuses of the plurality of portable medical treatment and guidance apparatuses was last used.

In some implementations, the at least one processor and memory are further configured to determine the closest nearby portable medical treatment and guidance apparatuses to a respective portable medical treatment and guidance apparatus.

In some implementations, the at least one processor and memory are further configured to remote control at least one of the plurality of portable medical treatment and guidance apparatuses.

In some implementations, the at least one processor and memory are further configured to remote control at least one medical item within a respective portable medical treatment and guidance apparatus of the plurality of portable medical treatment and guidance apparatuses.

In some implementations, the at least one processor and memory are further configured to notify mobile devices within a proximal location of a respective portable medical treatment and guidance apparatus of the plurality of portable medical treatment and guidance apparatuses when the respective portable medical treatment and guidance apparatus is turned on.

In some implementations, the at least one processor and memory are further configured to notify mobile devices within a proximal location of a respective portable medical treatment and guidance apparatuses of the plurality of portable medical treatment and guidance apparatuses when at least one medical item is removed from the respective portable medical treatment and guidance apparatuses.

In another aspect, a medical treatment and guidance apparatus management system is provided. The management system can include: a plurality of portable medical treatment and guidance apparatuses, each portable medical treatment and guidance apparatus including: a treatment and guidance user interface configured to provide an interactive query flow for assisting a user in providing medical treatment, a plurality of medical supplies for the user to provide the medical treatment, and communications circuitry configured to provide status information of the portable medical treatment and guidance apparatus to at least one medical treatment and guidance apparatus management device wherein the status information includes at least inventory data for the portable medical treatment and guidance apparatus; the at least one medical treatment and guidance apparatus management device having a management user interface for providing a status indication of the plurality of portable medical treatment and guidance apparatuses. The at least one medical treatment and guidance apparatus management device configured to: receive status updates regarding the plurality of portable medical treatment and guidance apparatuses, and update, on the management user interface, the status indication of the plurality of portable medical treatment and guidance apparatuses based on the received status updates.

In some implementations, the status indication of the plurality of portable medical treatment and guidance apparatuses comprises readiness information of each respective portable medical treatment and guidance apparatus representing whether each respective portable medical treatment and guidance apparatus is ready to be used.

In some implementations, the status indication of the plurality of portable medical treatment and guidance apparatuses comprises battery information of each respective portable medical treatment and guidance apparatus representing whether each respective portable medical treatment and guidance apparatus is sufficiently charged.

In some implementations, the status indication of the plurality of portable medical treatment and guidance apparatuses comprises self-diagnostic information of each respective portable medical treatment and guidance apparatus representing whether each respective portable medical treatment and guidance apparatus has passed a self-diagnostic test. The self-diagnostic test can include ensuring battery levels for each battery operable medical item within the respective portable medical treatment and guidance apparatus is above a threshold, ensuring an expiration date of each expireable medical item within the respective portable medical treatment and guidance apparatus has not occurred, and/or ensuring each removable medical item is present within the respective portable medical treatment and guidance apparatus.

In some implementations, the at least one medical treatment and guidance apparatus management device is further configured to transmit a request for a self-diagnostic test to be performed by at least one of the plurality of portable medical treatment and guidance apparatuses.

In some implementations, the at least one medical treatment and guidance apparatus management device is further configured to transmit a request for a self-diagnostic test to be performed by at least one medical item housed within at least one of the plurality of portable medical treatment and guidance apparatuses. The self-diagnostic test can include ensuring a battery level of the at least one medical item is above a threshold, ensuring an expiration date of the at least one medical item has not occurred, and/or ensuring the at least one medical item is present in the respective portable medical treatment and guidance apparatus.

In some implementations, the at least one medical treatment and guidance apparatus management device is further configured to present via the management user interface whether the inventory data for the portable medical treatment and guidance apparatus is below a threshold.

In some implementations, the at least one medical treatment and guidance apparatus management device is further configured to initiate a request to acquire more of at least one medical item.

In some implementations, the at least one medical treatment and guidance apparatus management device is further configured to initiate a purchase to acquire more at least one medical item.

In some implementations, the at least one medical treatment and guidance apparatus management device is further configured to prioritize a purchase of at least one medical item over another at least one medical item.

In some implementations, the at least one medical treatment and guidance apparatus management device is further configured to indicate which portable medical treatment and guidance apparatuses of the plurality of portable medical treatment and guidance apparatuses have passed a self-diagnostic test representing that the respective portable medical treatment and guidance apparatus is ready for use.

In some implementations, the at least one medical treatment and guidance apparatus management device is further configured to indicate which portable medical treatment and guidance apparatuses of the plurality of portable medical treatment and guidance apparatuses require attention.

In some implementations, the at least one medical treatment and guidance apparatus management device is further configured to indicate a location of each portable medical treatment and guidance apparatuses of the plurality of portable medical treatment and guidance apparatuses that require attention.

In some implementations, the at least one medical treatment and guidance apparatus management device is further configured to indicate a date that each portable medical treatment and guidance apparatuses of the plurality of portable medical treatment and guidance apparatuses last passed a self-diagnostic test.

In some implementations, the at least one medical treatment and guidance apparatus management device is further configured to indicate a date that each portable medical treatment and guidance apparatuses of the plurality of portable medical treatment and guidance apparatuses was last opened.

In some implementations, the at least one medical treatment and guidance apparatus management device is further configured to indicate a date that each portable medical treatment and guidance apparatuses of the plurality of portable medical treatment and guidance apparatuses was last used.

In some implementations, the at least one medical treatment and guidance apparatus management device is further configured to determine the closest nearby portable medical treatment and guidance apparatuses to a respective portable medical treatment and guidance apparatus.

In some implementations, the at least one medical treatment and guidance apparatus management device is further configured to remote control at least one of the plurality of portable medical treatment and guidance apparatuses.

In some implementations, the at least one medical treatment and guidance apparatus management device is further configured to remote control at least one medical item within a respective portable medical treatment and guidance apparatus of the plurality of portable medical treatment and guidance apparatuses.

In some implementations, the at least one medical treatment and guidance apparatus management device is further configured to notify mobile devices within a proximal location of a respective portable medical treatment and guidance apparatus of the plurality of portable medical treatment and guidance apparatuses when the respective portable medical treatment and guidance apparatus is turned on.

In some implementations, the at least one medical treatment and guidance apparatus management device is further configured to notify mobile devices within a proximal location of a respective portable medical treatment and guidance apparatuses of the plurality of portable medical treatment and guidance apparatuses when at least one medical item is removed from the respective portable medical treatment and guidance apparatuses.

BRIEF DESCRIPTIONS OF THE DRAWINGS

Many advantages of the present disclosure will be apparent to those skilled in the art with a reading of this specification in conjunction with the attached drawings, wherein like reference numerals are applied to like elements and wherein.

Figure 4A:
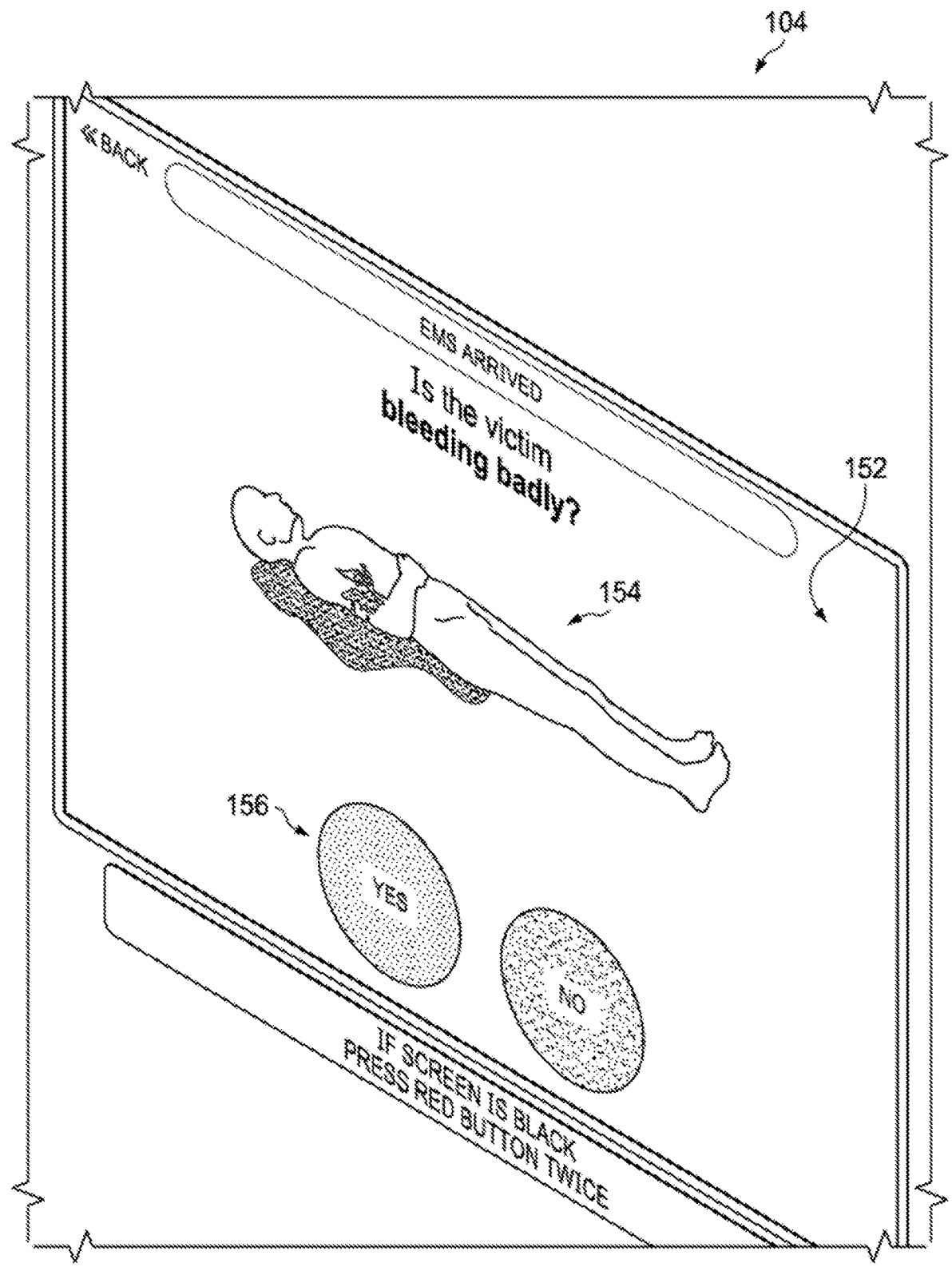
Figure 4B:
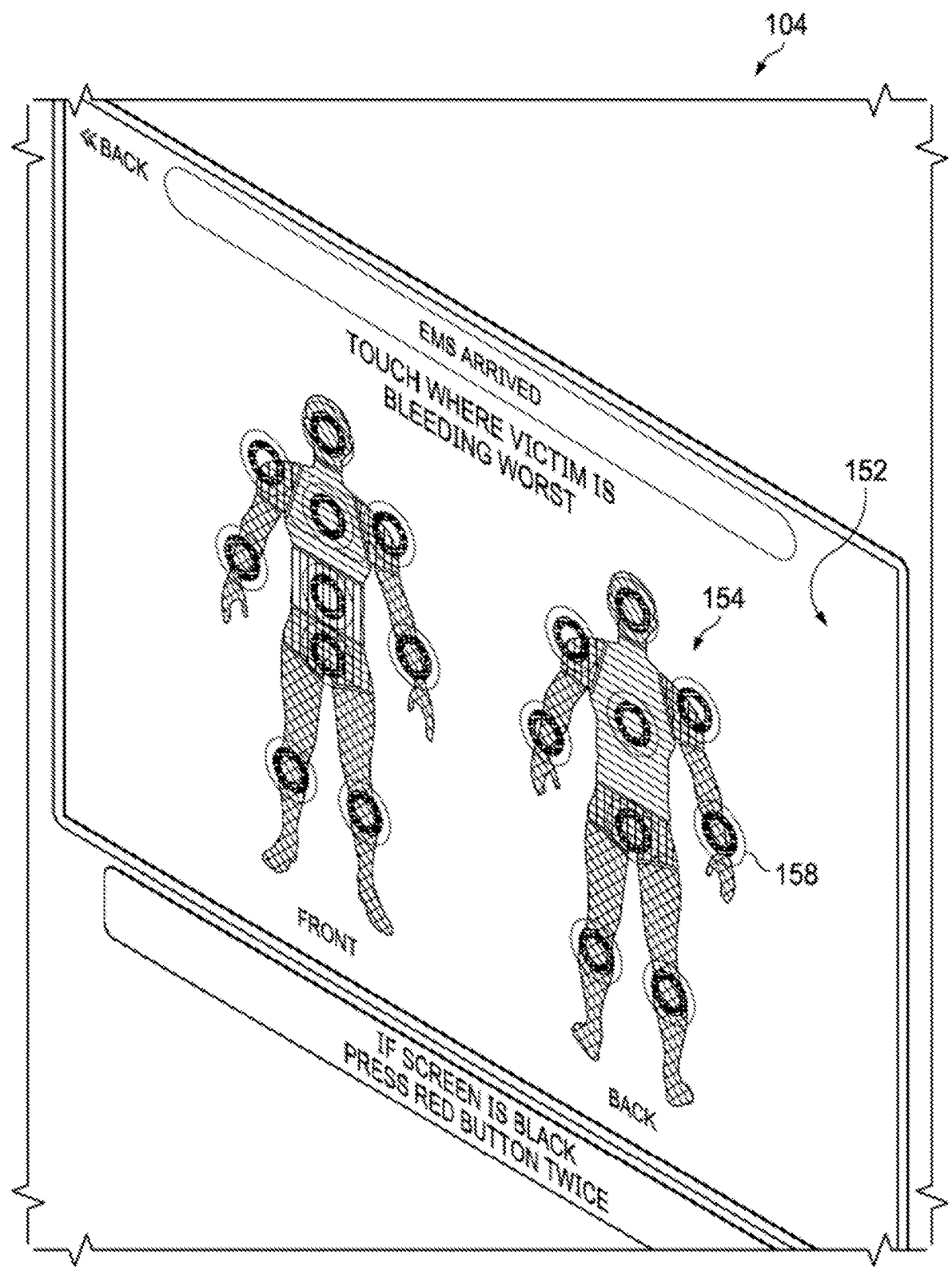
Figure 4C:
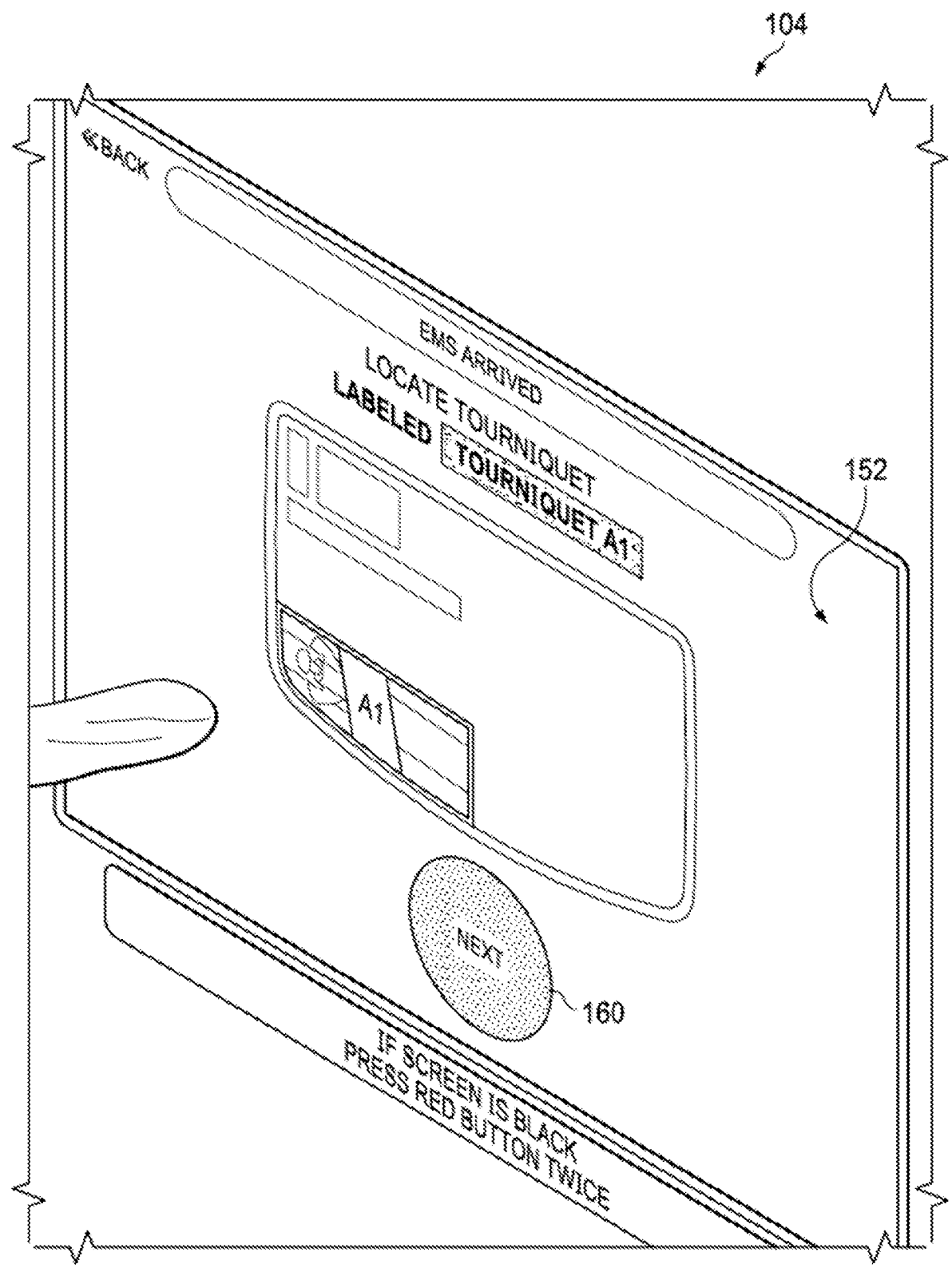
Figure 5:
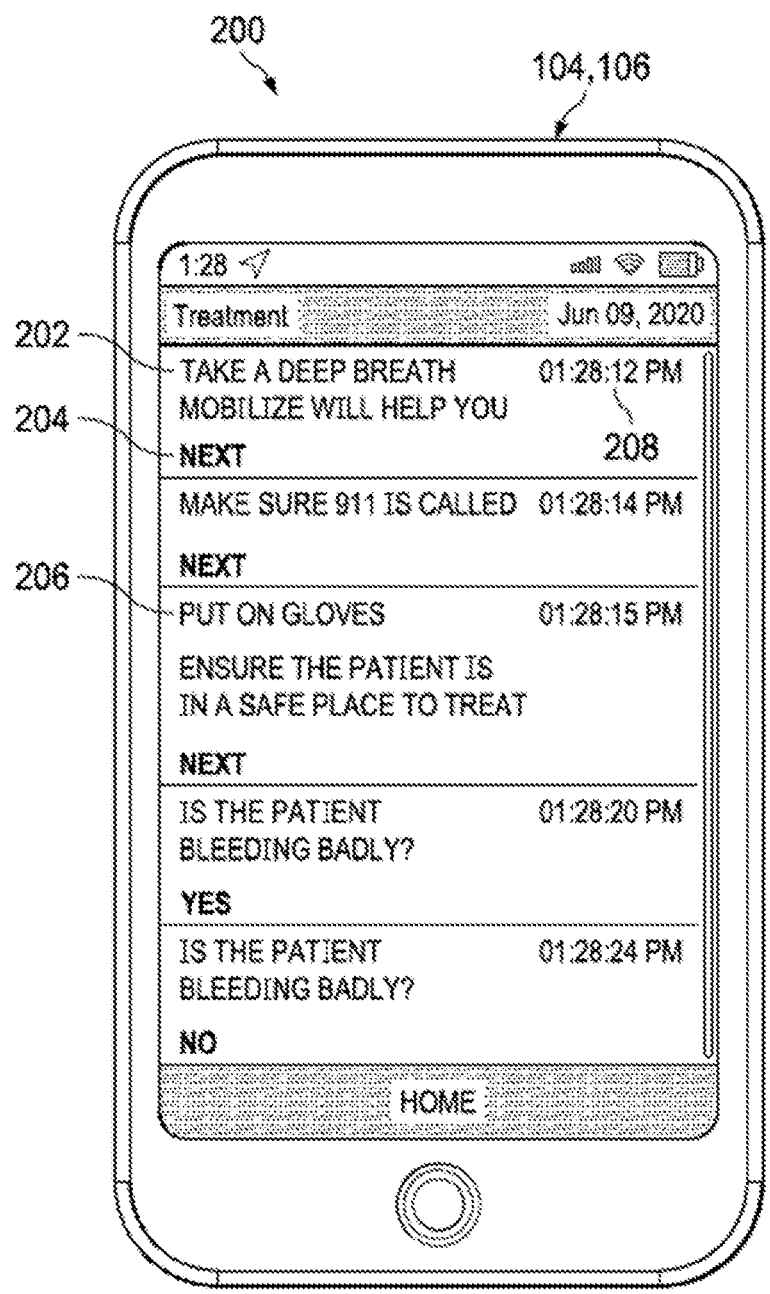
Figure 6:
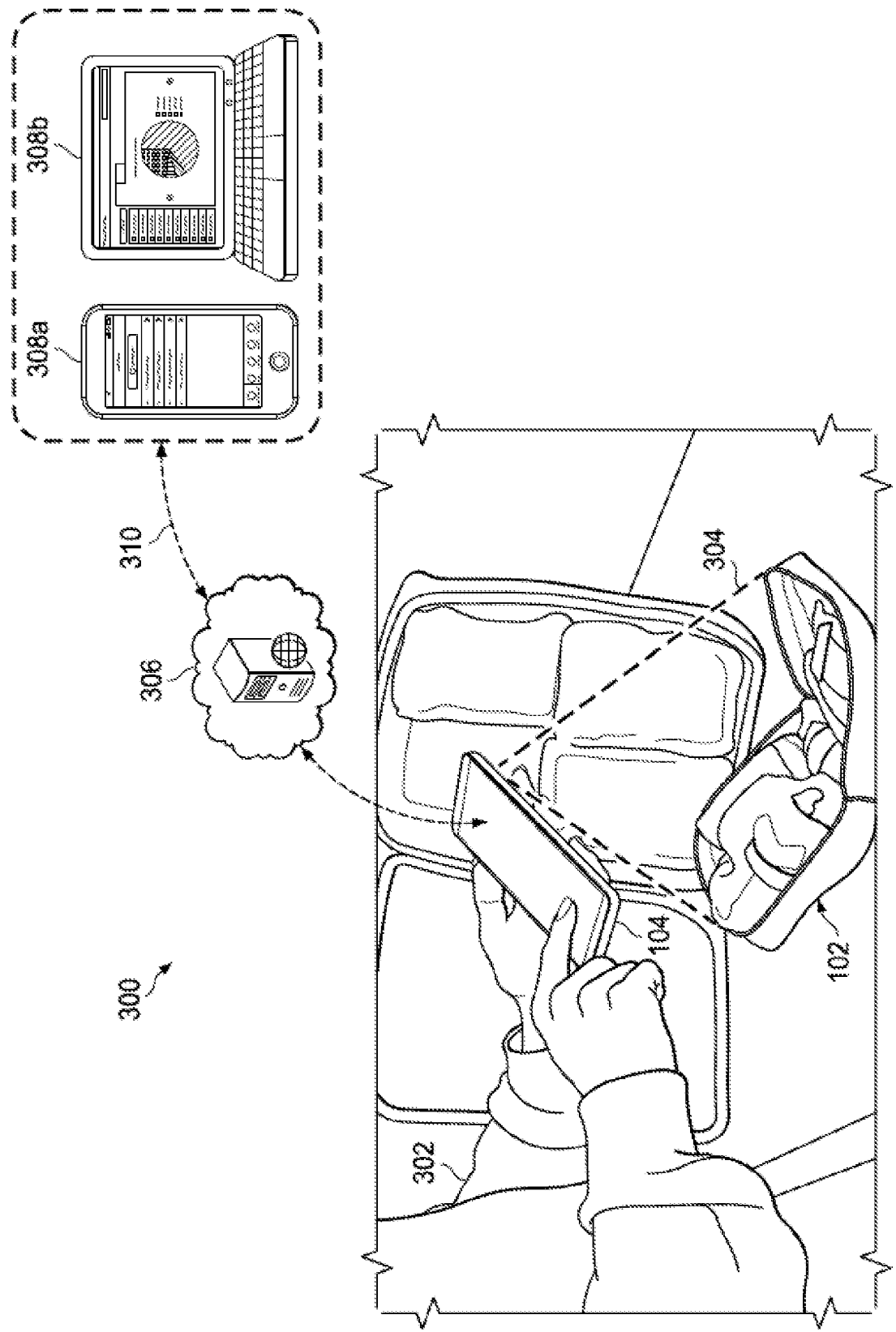
Figure 7:
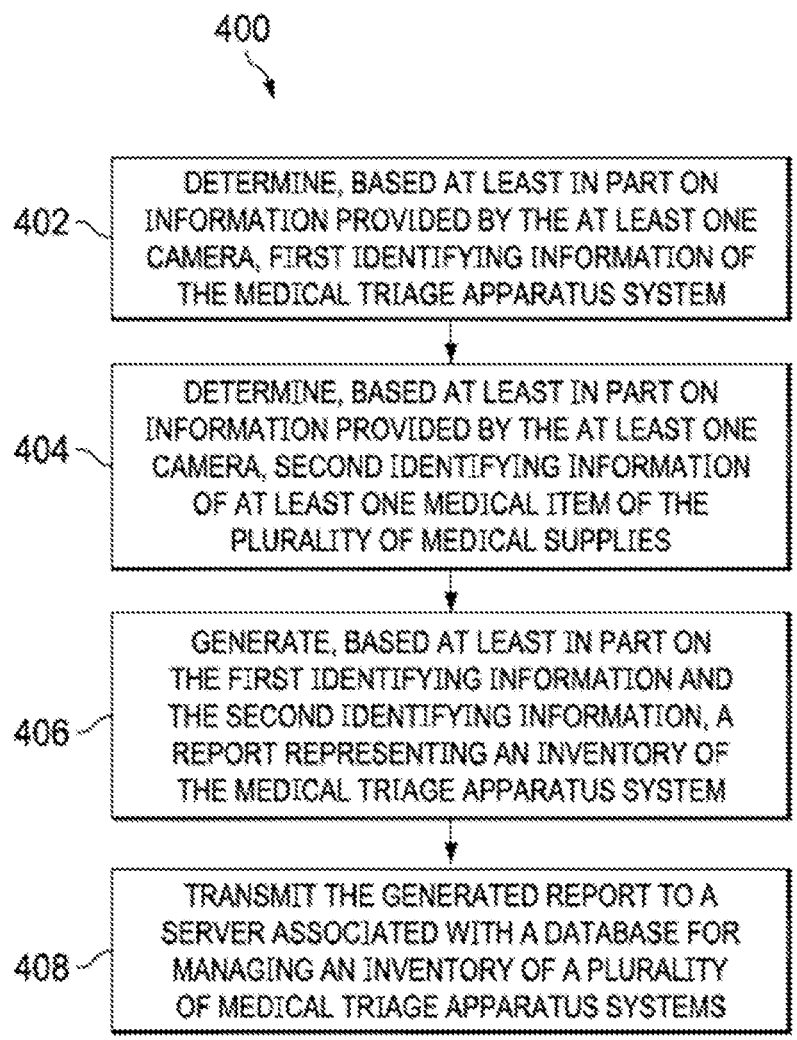
Figure 11:
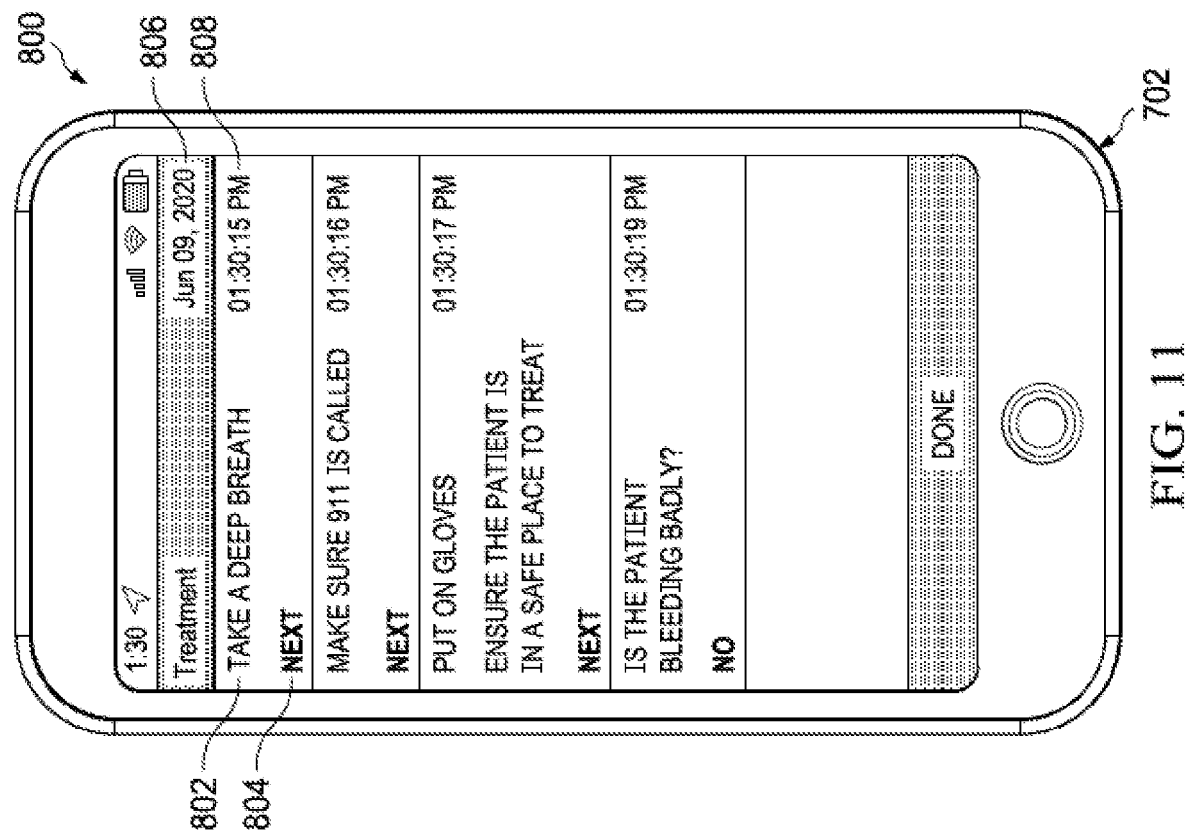
Figure 10:
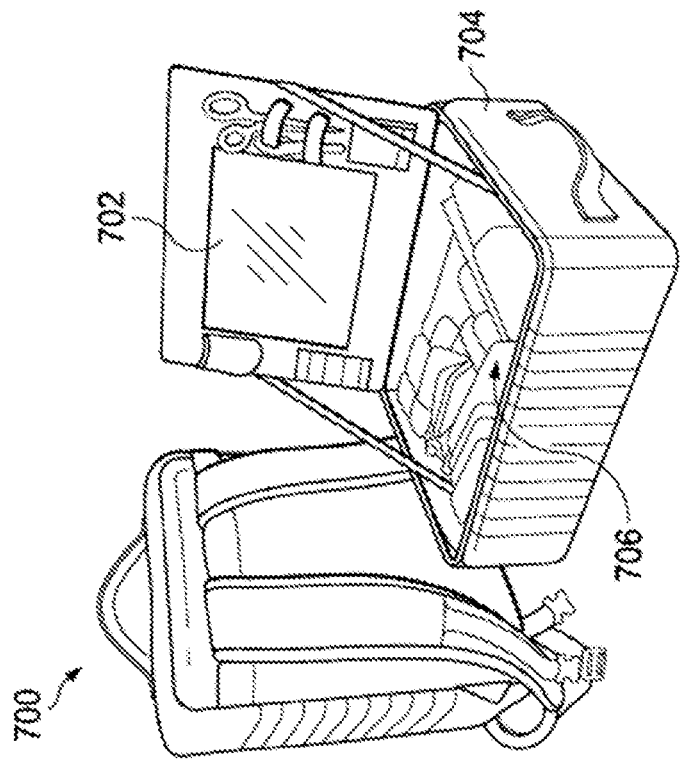
Figure 12:
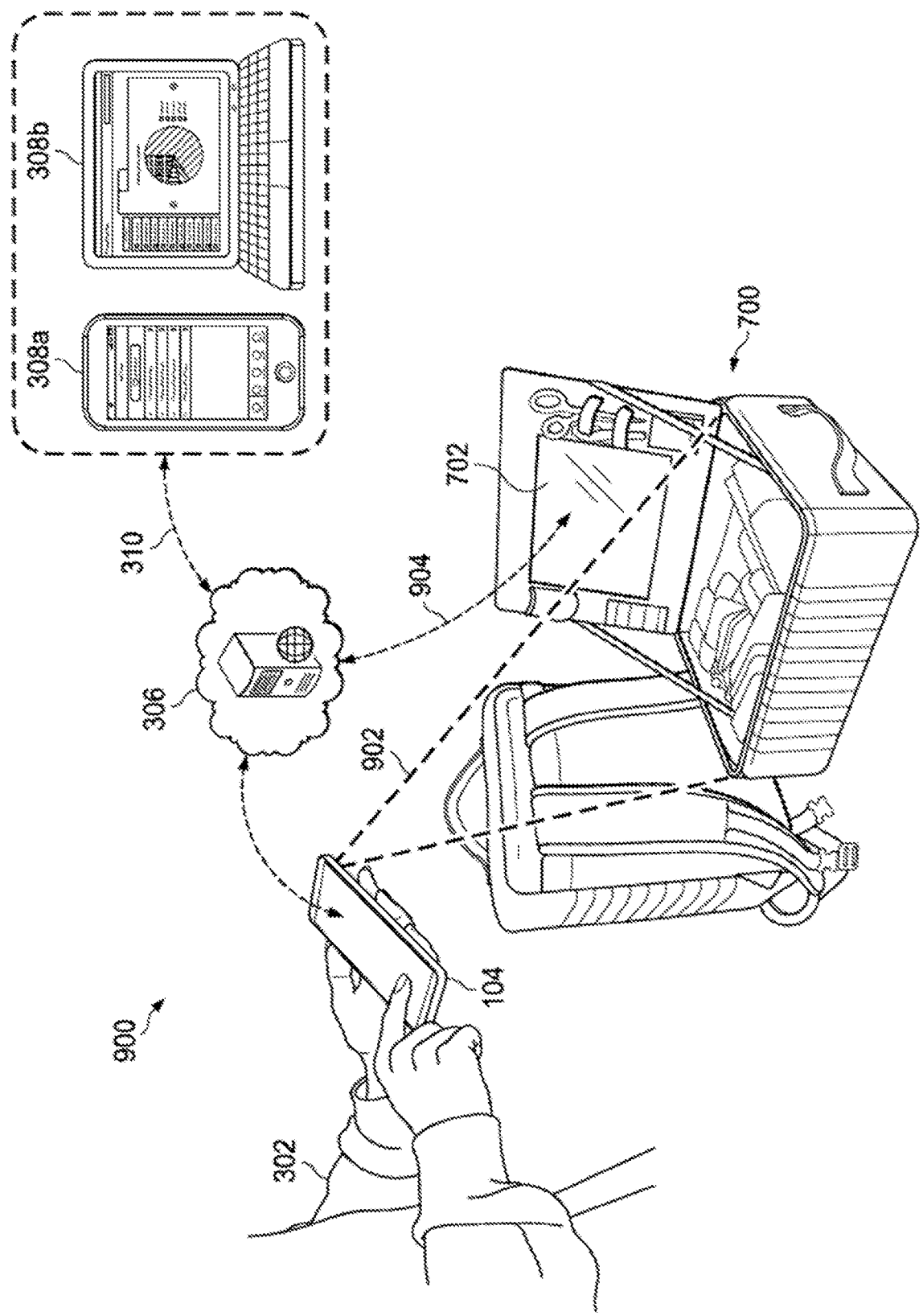
Figure 13:
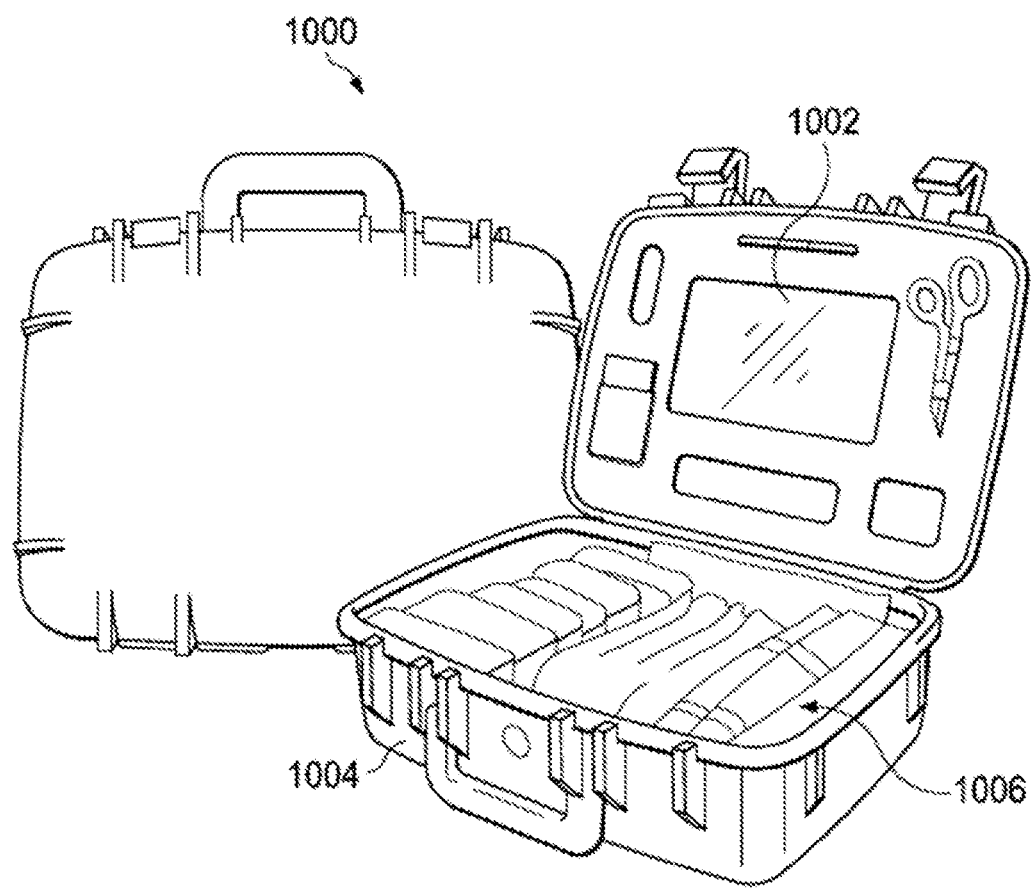
Figure 14:
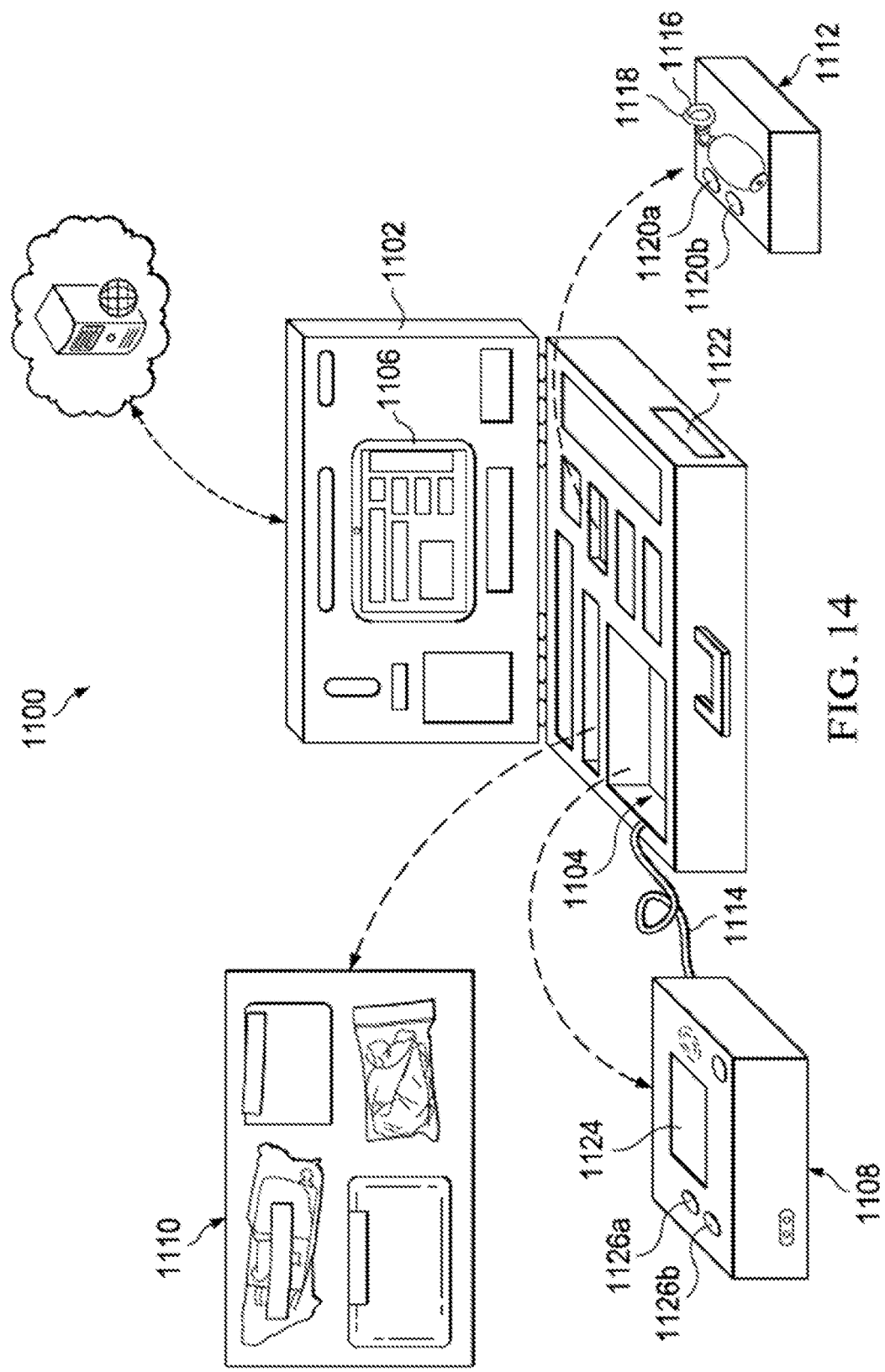
Figure 15A:
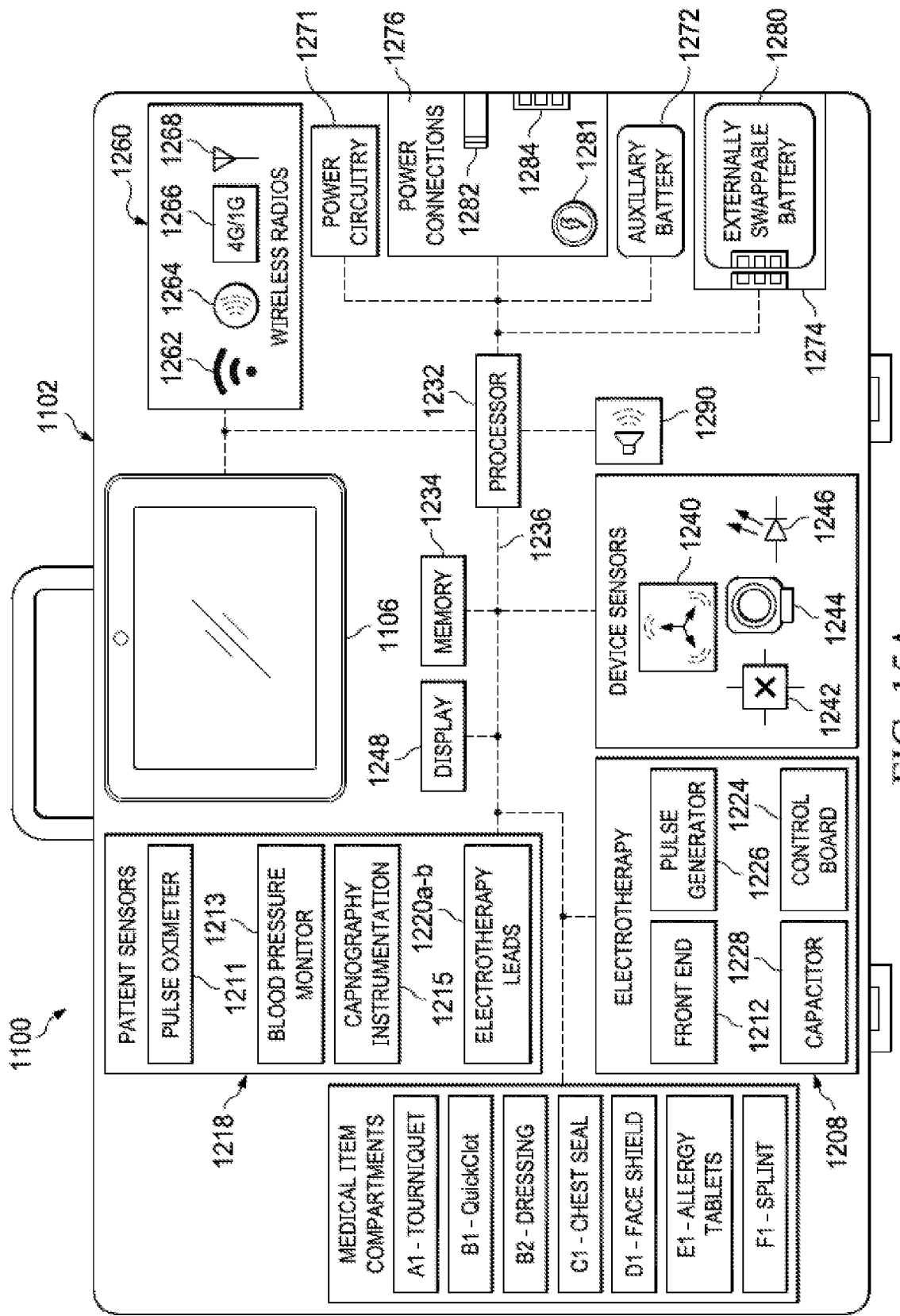
Figure 15B:
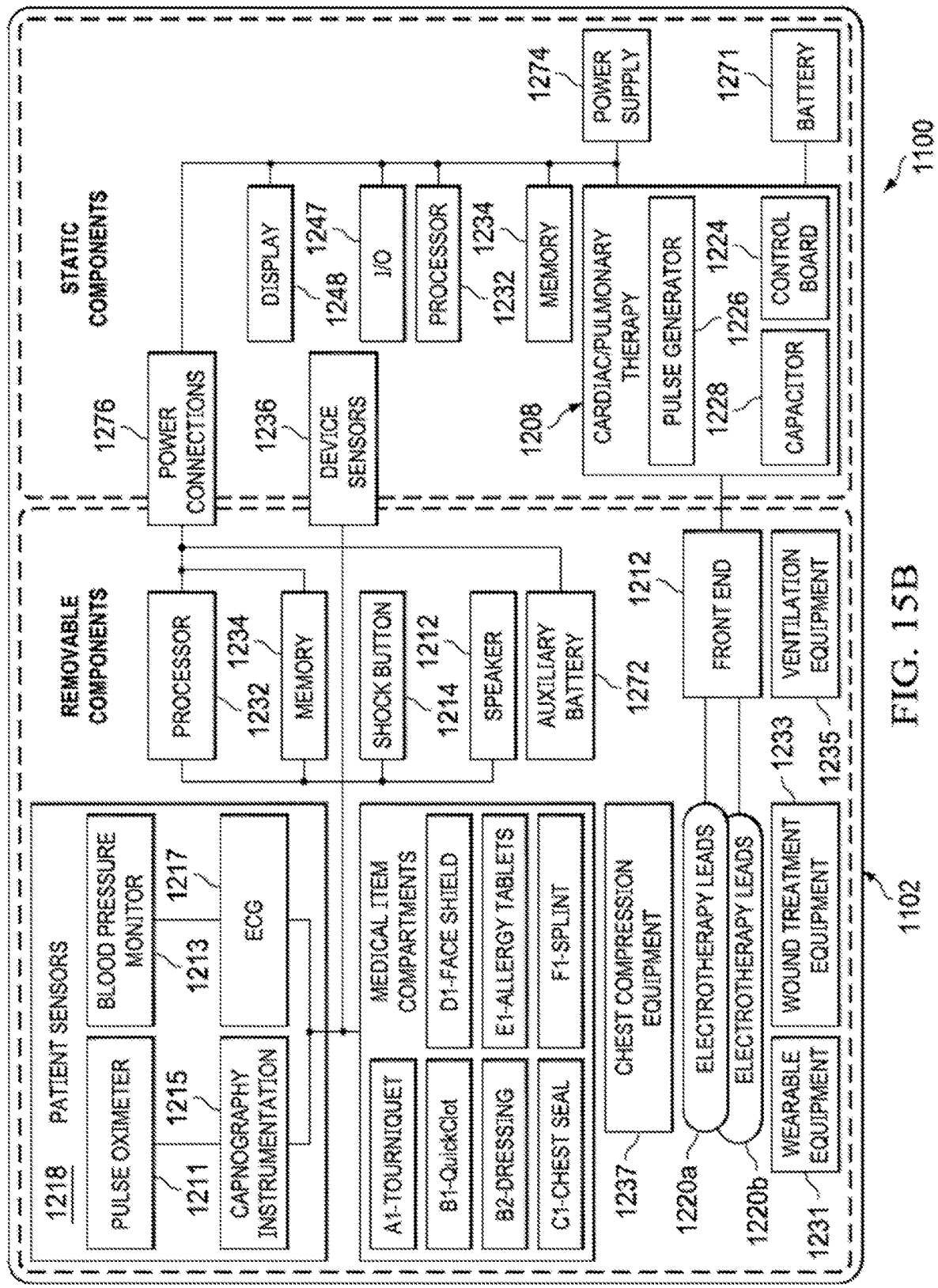
Figure 16:
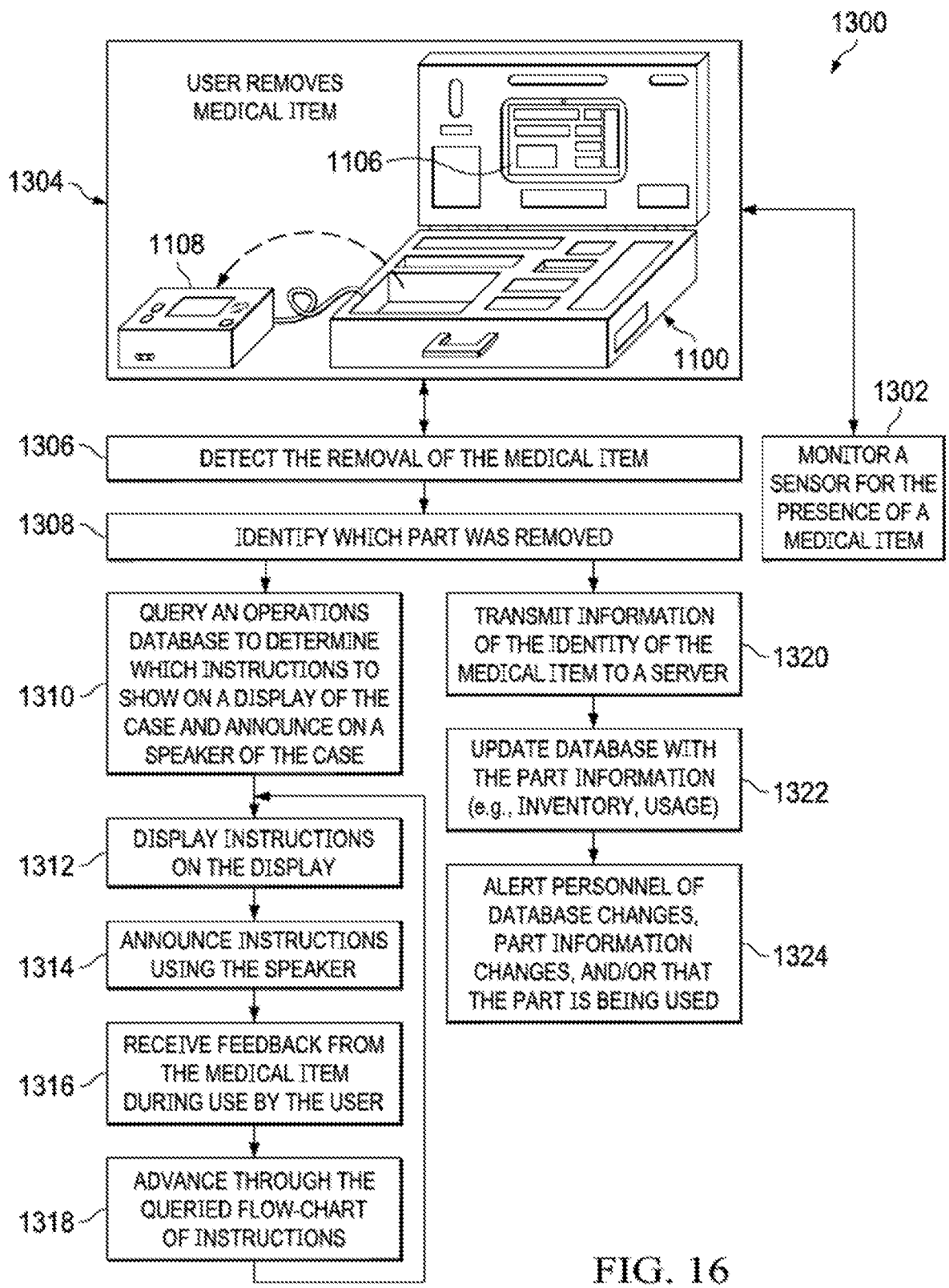
Figure 17:
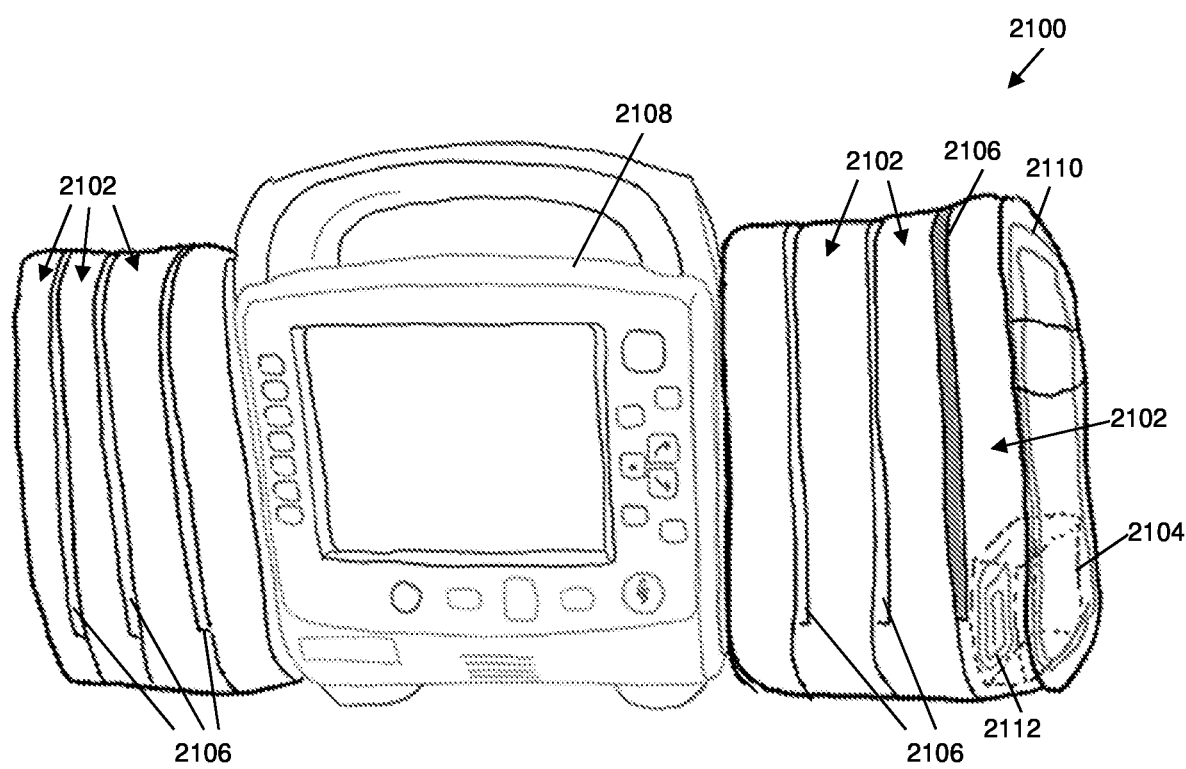
Figure 20B:
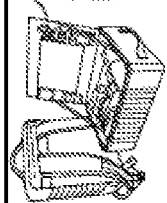
Figure 21A:
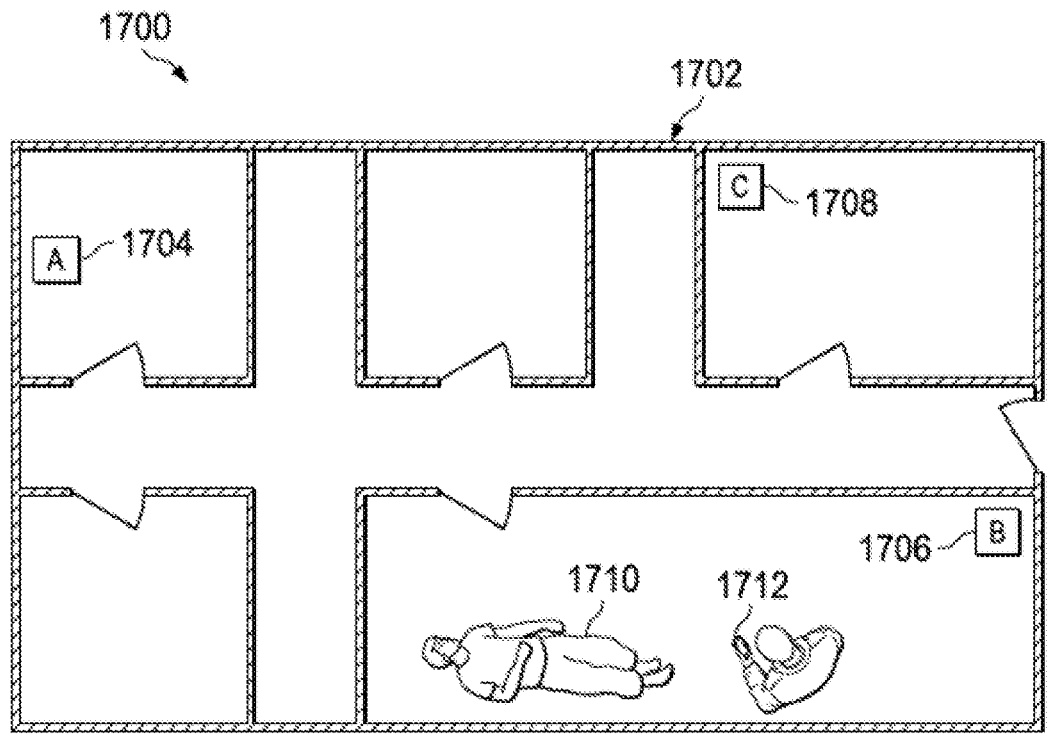
Figure 21B:
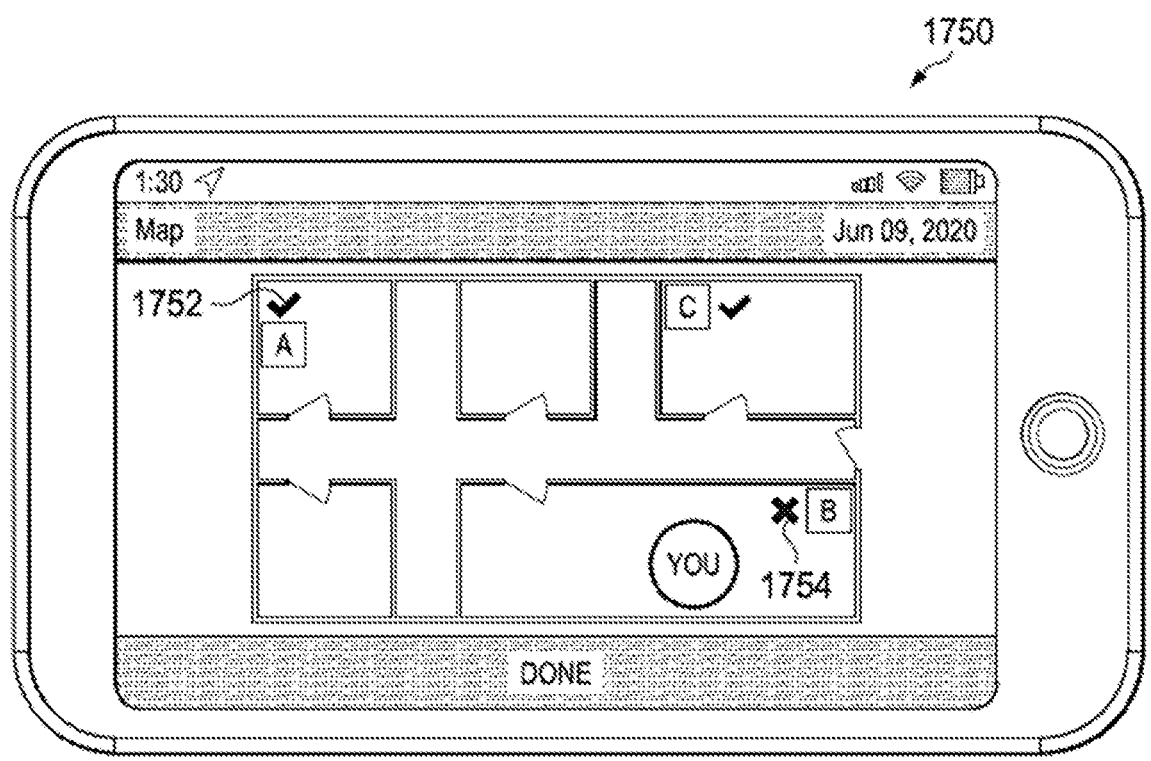
Figure 22:
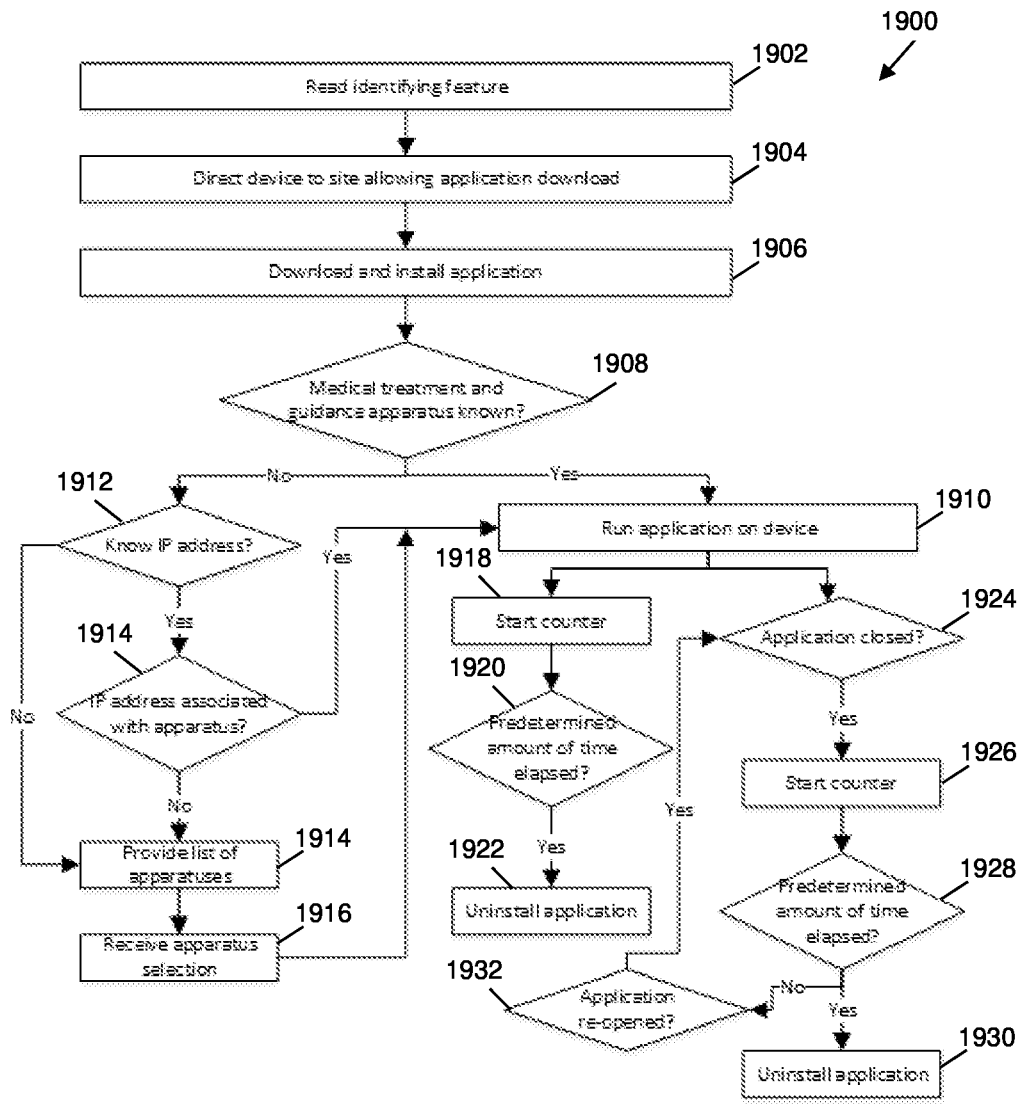
Figure 23:
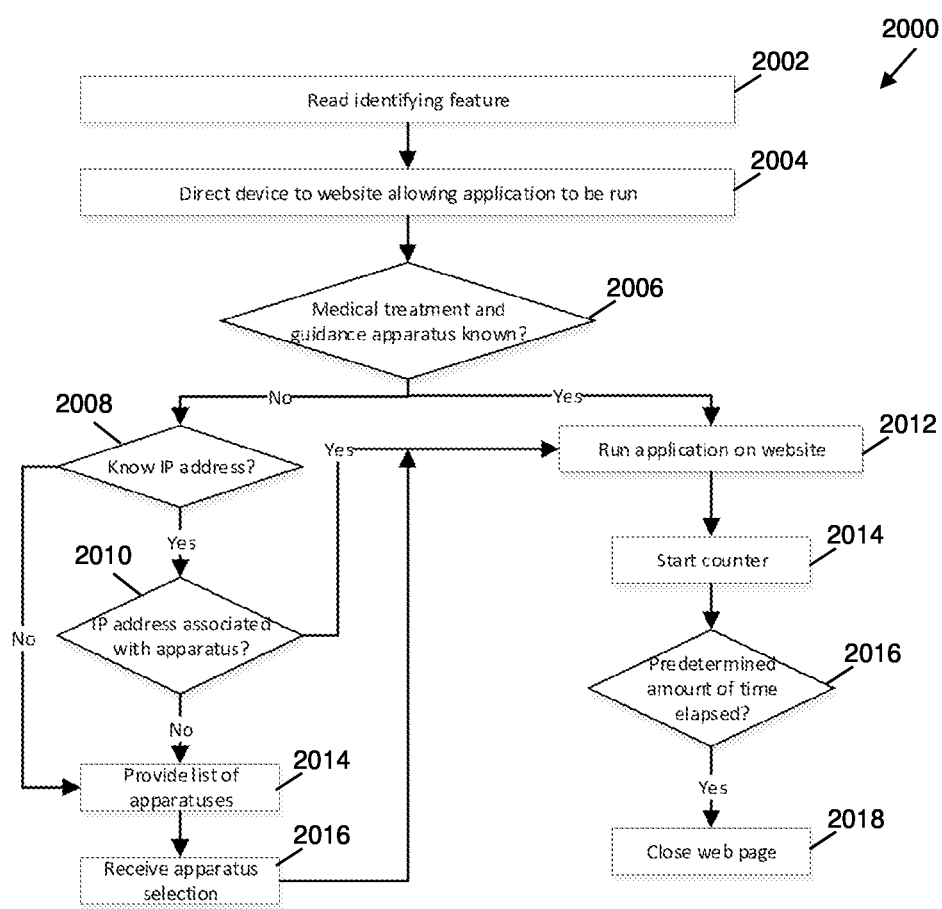
Figure 24:
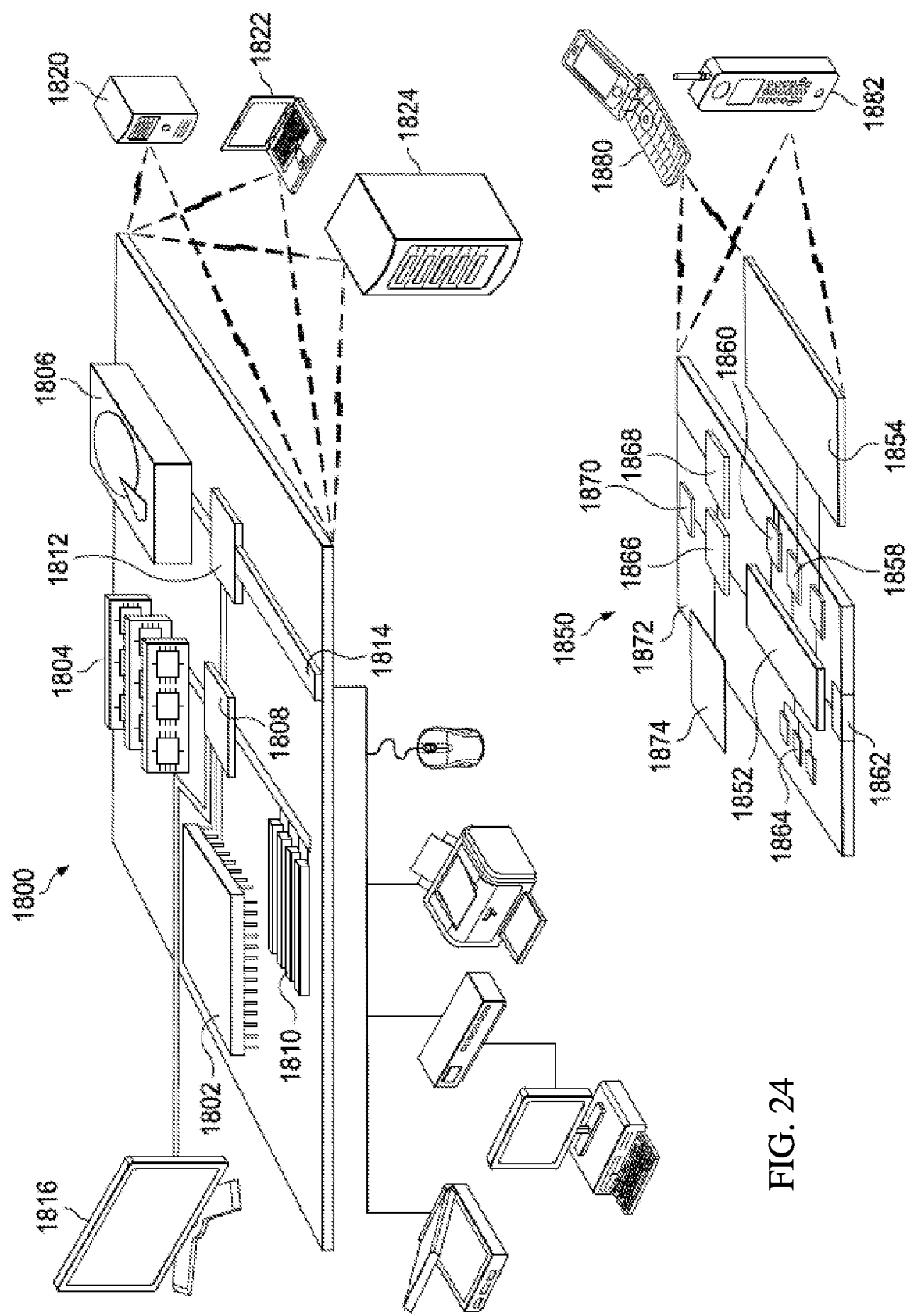

FIGS. 4A, 4B, and 4C show an interactive query of instructions presented on a mobile device or tablet of a portable medical treatment and guidance apparatus;

FIG. 5 shows a record of instructions and associated keystrokes entered by a user on a mobile device when administering treatment using a portable medical treatment and guidance apparatus;

FIG. 6 shows a mobile device capturing an image of a portable medical treatment and guidance apparatus, transmitting this information to a database, and one or more devices querying the database for inventory management of the portable medical treatment and guidance apparatus;

FIG. 7 is a flowchart of a process in which a mobile device captures an image of the portable medical treatment and guidance apparatus, determines missing medical items, and communicates this information to a database for inventory management;

FIG. 8 shows a record of instructions and associated keystrokes entered by a user on a mobile device when administering treatment using a portable medical treatment and guidance apparatus;

FIG. 9 shows a record of instructions and associated keystrokes entered by a user on a mobile device when inventory management of a portable medical treatment and guidance apparatus;

FIG. 10 shows a portable medical treatment and guidance apparatus for treating medical emergencies with a removable tablet device in accordance with some embodiments;

FIG. 11 shows a record of instructions and associated keystrokes entered by a user on the removable tablet device of FIG. 10 when administering treatment using a portable medical treatment and guidance apparatus;

FIG. 12 shows a mobile device capturing an image of a portable medical treatment and guidance apparatus that includes a removable tablet device, transmitting this information to a database, and one or more devices querying the database for inventory management of the portable medical treatment and guidance apparatus;

FIG. 13 shows a portable medical treatment and guidance apparatus for treating medical emergencies with a built-in tablet device in accordance with some embodiments;

FIG. 14 shows a portable medical treatment and guidance apparatus for treating medical emergencies with sensors to detect when one or more medical items have been removed from a case of the portable medical treatment and guidance apparatus;

FIGS. 15A and 15B show a diagram and some internal components of the portable medical treatment and guidance apparatus in accordance with some embodiments;

FIG. 16 shows a flowchart of a process in which a portable medical treatment and guidance apparatus detects removal of one or more medical items in accordance with some embodiments;

FIG. 17 shows a portable medical treatment and guidance apparatus in accordance with some embodiments;

FIG. 18 shows a system where the portable medical treatment and guidance apparatuses of FIG. 2A, FIG. 10, FIG. 13, and FIG. 14 communicate with a database for inventory management and other devices query the database for inventory management status;

FIGS. 19A, 19B, 19C, and 19D show information displayed on a mobile device when querying the database for inventory management status of one of more portable medical treatment and guidance apparatuses in accordance with some embodiments;

FIGS. 20A and 20B show information displayed on a computational device for inventory management of one of more portable medical treatment and guidance apparatuses in accordance with some embodiments;

FIGS. 21A and 21B show a map of a building with multiple portable medical treatment and guidance apparatuses in proximity to a patient and a mobile device determining the closest portable medical treatment and guidance apparatus that has the required medical items for treating the medical emergencies of the patient;

FIG. 22 shows a flowchart of a process for downloading an app to a device using an identifying feature associated with a medical treatment and guidance apparatus in accordance with some embodiments;

FIG. 23 shows a flowchart of a process providing online functionality of an app using an identifying feature associated with a medical treatment and guidance apparatus in accordance with some embodiments; and FIG. 24 is a block diagram of computer systems forming part of the portable medical treatment and guidance apparatuses in according to some embodiments.

DETAILED DESCRIPTION

Embodiments of the present disclosure relate to systems and methods for ensuring that publicly accessible emergency medical equipment are fully functional and ready for use at all times in situations when they are called upon for use. Such emergency medical equipment may include, for example, not only automated external defibrillators (AEDs) which are useful for lay rescuers to treat cardiac arrest victims, but also portable medical treatment and guidance apparatuses designed for use with electronic interactive guidance that enables a user with little to no medical experience to administer urgent medical treatment. In the case of portable medical treatment and guidance apparatuses described herein, it is desirable that such equipment be ready at all times for use. This includes ensuring that the interface that provides the electronic interactive guidance (e.g., tablet, mobile device, built-in display and/or touchscreen) is sufficiently powered, and that the inventory of the treatment and guidance apparatus is stocked so that required medical item(s) for administering the medical treatment are available and accounted for, not missing. Otherwise, in the unpredictable event when an emergency medical situation arises, it can be tragic when the equipment used to treat the medical condition is not sufficiently functional, or otherwise ready and stocked. Accordingly, embodiments described herein include tools for effectively and efficiently managing such equipment.

In accordance with embodiments of the present disclosure, the inventory of portable medical treatment and guidance apparatuses can be effectively managed to ensure that supplies and equipment are reliably available in emergency situations. For example, a portable medical treatment and guidance apparatus can detect the removal of medical items (e.g., tourniquets, medicine, gauze, etc.) and equipment (respiratory devices, CPR equipment, etc.) and update a database to reflect current, up-to-date, inventory status. Further, the database can receive information from multiple apparatuses and maintain a total inventory across the entire network. For example, an inspector checking the database can see a holistic view of the inventory of all the portable medical treatment and guidance apparatuses, as well as receive notifications and updates as to whether one or more portable medical treatment and guidance apparatuses within a fleet require attention.

Mobile devices (also referred to herein as "mobile computing devices" and "mobile computer devices") can also be used in the management of the portable medical treatment and guidance apparatuses. In some implementations, a mobile device can be configured to capture images of the contents of portable medical treatment and guidance apparatuses and communicate this data and/or related information to the database. For example, a smartphone can not only provide medical instructions for administering aid to a patient, but also capture images of the inventory of the portable medical treatment and guidance apparatus. Such images may be analyzed in a manner using image recognition so that it is evident which items of inventory are present or absent from the treatment and guidance apparatus, which then results in a signal being sent to the database for updating of the device identification (ID) for that particular apparatus. As a result, appropriate notifications and/or reports may be provided to other devices indicating the status of the treatment and guidance apparatus. In some examples, the smartphone can also communicate with the database, so that the medical instructions are updated depending on the medical items on-hand. For example, if the smartphone determines a small gauze is missing from the portable medical treatment and guidance apparatus, the medical instructions can be updated to instruct the user to use a larger gauze (that is present) instead of the smaller gauze that is missing.

In some embodiments, the medical instructions, and/or the response keystrokes from the user, can be used to infer the quantity of the medical items within the portable medical treatment and guidance apparatus. In some examples, when the user acknowledges that certain steps of administering aid were conducted (e.g., in response to a query acknowledging that the user had given insulin to a patient, if the user selects "YES" then the inventory system updates the inventory to reflect that insulin has been used and needs to be replenished). In some examples, the management system infers which medical items have been used based on a case report. In this scenario, if the case report indicates that insulin, gauze, and a tourniquet may have been used in administering aid to the patient, the inventory system may assume or otherwise record that the insulin, gauze, and the tourniquet are no longer available and proceed to generate a record that the insulin, gauze, and the tourniquet should be replenished. In some examples, when the management system processes the case report and determines a medical item may have been used (e.g., if the medical item is listed on the case report, the management system may infer that the medical item has been used), the management system triggers a reminder/notification to an inspector to check to see if the medical items need replenishment (i.e., the inspector can confirm the inferred use represented by the case report).

In some embodiments, inventory status within the database can be processed to automatically reorder medical items, flag issues that the inspector should be aware of (e.g., treatment and guidance apparatus has been used and needs servicing, low battery issues, not setup properly, tampering, theft, etc.) or other unexpected scenarios (e.g., the case was opened but no medical emergency was noted, etc.), or redirect caregivers to properly stocked portable medical treatment and guidance apparatuses when in need. In addition to inventory status, the database can include information on expiration dates, dates and information associated with self-evaluations of medical equipment within the portable medical treatment and guidance apparatuses (e.g., defibrillating or other medical equipment may frequently power on to perform a self-evaluation and the data and results from this process can be sent back to the database and stored), and case reports that include medical instructions and caregiver responses that were presented to the caregiver.

Figure 1:
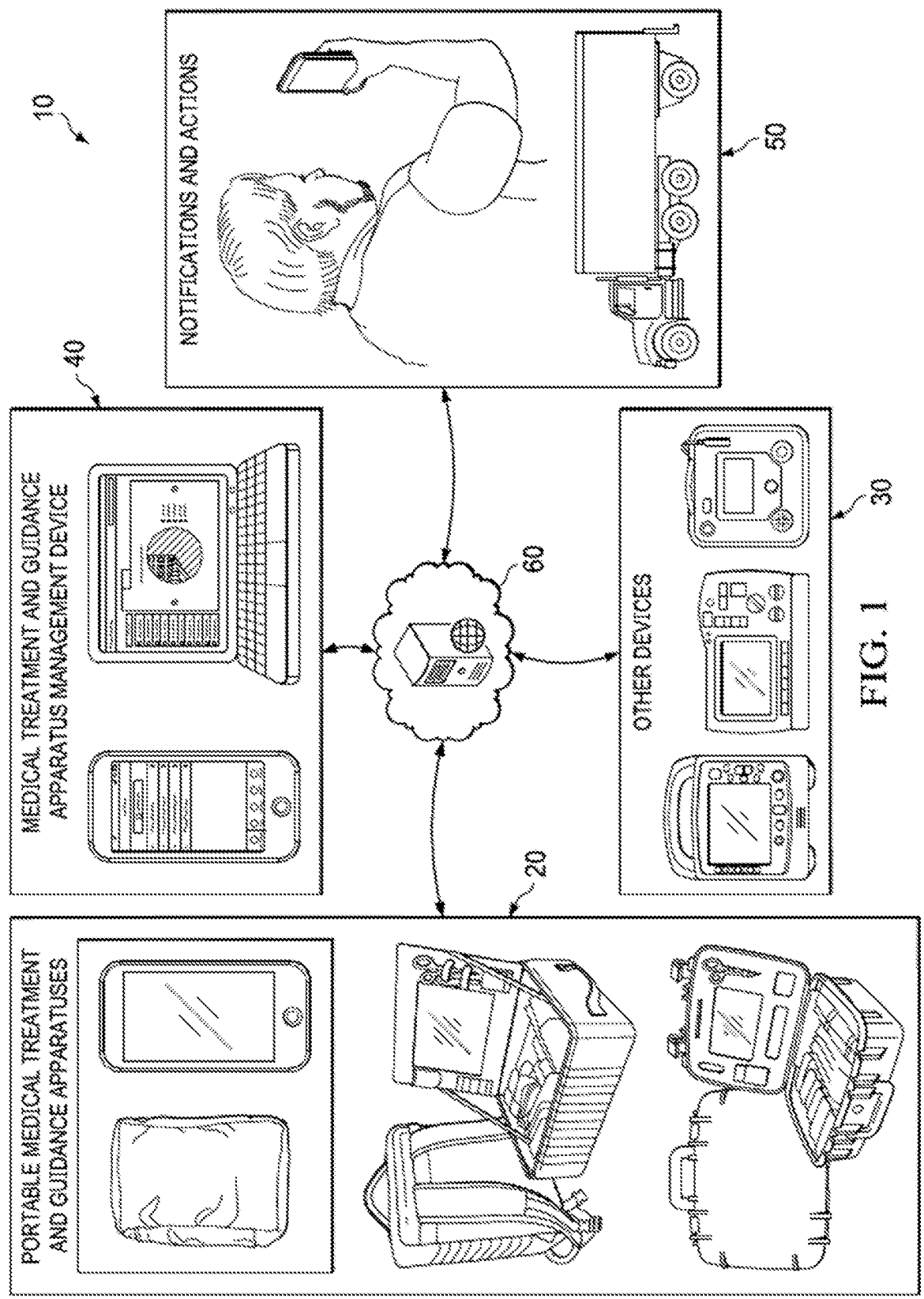
FIG. 1 shows a system where a database is updated and queried to obtain inventory information and provide notifications to allow for replenishment of medical items.

FIG. 1 shows a medical treatment and guidance apparatus management system 10. The management system 10 includes portable medical treatment and guidance apparatuses 20 that contain medical items (e.g., medical equipment and medical supplies) for administering medical aid. The portable medical treatment and guidance apparatuses 20 include an electronic device (e.g., a tablet, smartphone) that communicates with a server 60 that stores a database of inventory for each portable medical treatment and guidance apparatuses 20 within the management system 10. Some portable medical treatment and guidance apparatuses 20 include the electronic device directly (e.g., a built-in tablet) and others are intended to be used with a mobile device of a user (e.g., a smartphone). In most scenarios, the portable medical treatment and guidance apparatuses 20 are usable with a mobile device regardless of whether a built-in electronic device is provided.

In some embodiments, the management system 10 includes devices 30 other than the portable medical treatment and guidance apparatuses 20. The other devices 30 include any network enabled electronic medical device such a defibrillator. Inclusion of the other devices 30 in the management system 10 enables inventory tracking and use of all medical devices within a fleet of medical devices (i.e., not only just portable medical treatment and guidance apparatuses 20).

The management system 10 includes medical treatment and guidance apparatus management devices 40 (e.g., mobile devices [tablets, smart phones, etc.], laptops, desktops, etc.) that query the database hosted by the server 60 and determine when each of the portable medical treatment and guidance apparatuses 20 require attention by the inspector or need medical items replenished (e.g., by displaying a notification to replenish the medical item). Functions of the medical treatment and guidance apparatus management devices 40 may also be executed by the server 60 itself via software.

In some embodiments, the management system 10 (e.g., via the server 60) transmits notifications/alerts and/or takes action 50 in response to an inventory level of the portable medical treatment and guidance apparatuses 20. For example, in some cases, the server 60 transmits a notification to a smartphone associated with inspectors informing the inspector that a certain portable medical treatment and guidance apparatus 20 needs attention. In some examples, the management system 10 determines that a battery of a certain portable medical treatment and guidance apparatus 20 is low and transmits a notification to the inspector to recharge the battery. In some examples, the management system 10 determines that a certain medical item has been used (e.g., by inferring use from the case report) and initiates an order to purchase more of the used medical items (e.g., by generating a record that may then be used to notify a manager to order or otherwise check to see if the item(s) need replacement, by placing the item(s) on a list for future ordering, amongst other methods).

Figure 2A:
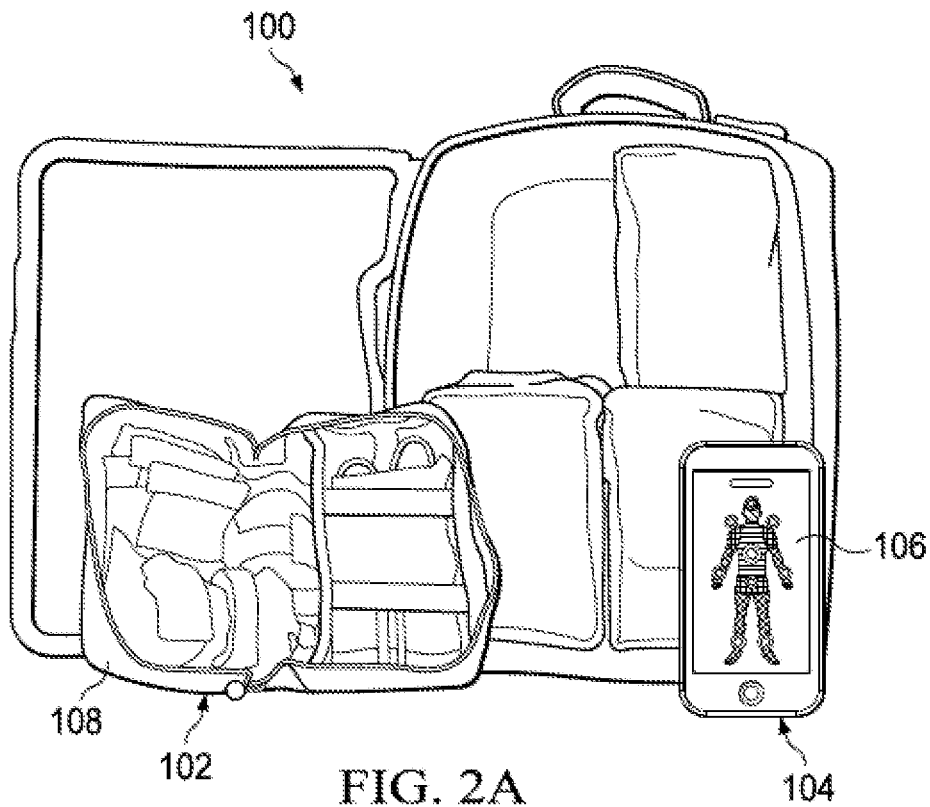
FIGS. 2A and 2B show a portable medical treatment and guidance apparatus for treating medical emergencies in accordance with some embodiments.

FIG. 2A shows a multi-pack system 100 that includes four portable medical treatment and guidance apparatuses 102 for treating medical emergencies. Examples of such multi-pack systems 100 are the Mobilize Public Access Rescue System of ZOLL Medical Corporation of Chelmsford, Massachusetts.

In certain embodiments, each portable medical treatment and guidance apparatus 102 includes a case 108 (i.e., a housing) with a plurality of medical supplies (or medical items) for administering medical treatment (e.g., but not limited to, a SOF-T Wide tourniquet, a 4" emergency trauma dressing, a QuikClot bleeding control dressing, a Hyfin chest seal, a CPR face shield with bite block, an emergency space Mylar blanket, a trauma shears, and 8× nitrile gloves). Examples of such portable medical treatment and guidance apparatuses 102 are the ZOLL Mobilize Public Access Utility Kit and the ZOLL Mobilize Public Access Compact Rescue System. The housing 108 is a soft fabric material and includes a zipper to seal the contents of the housing 108.

Figure 3:
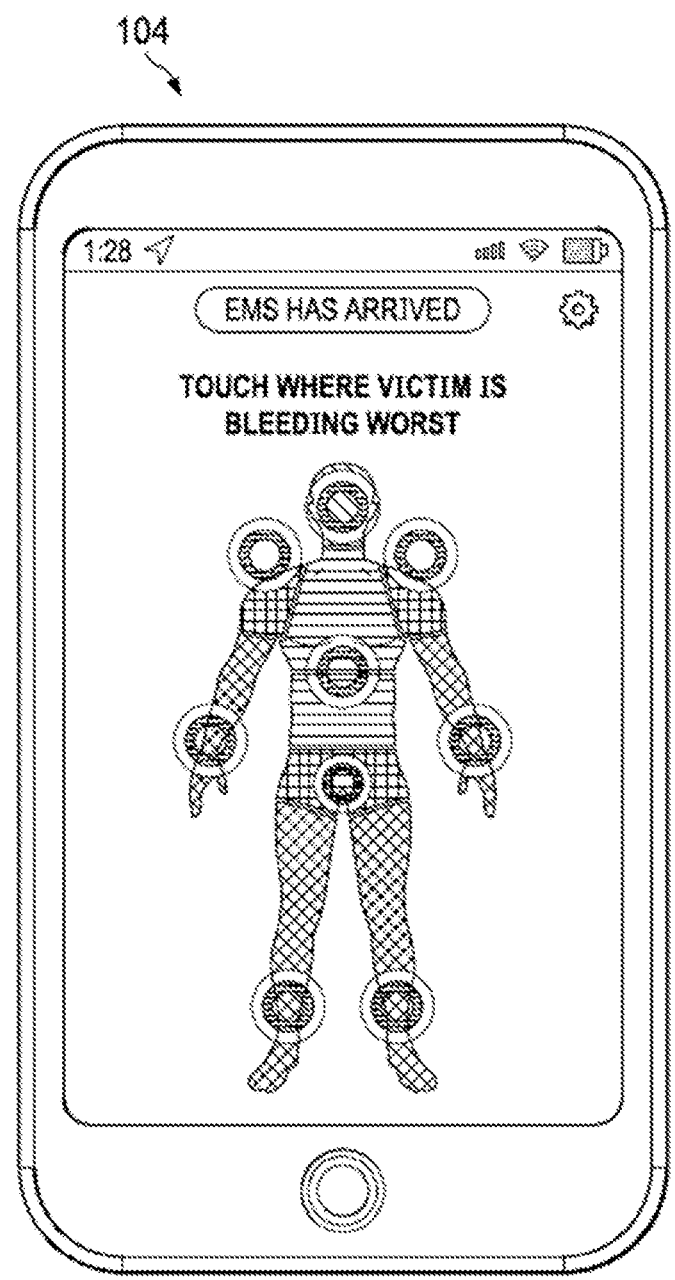
FIG. 3 shows a screenshot of an interactive query on a mobile device or tablet of a portable medical treatment and guidance apparatus.

Inventory of the portable medical treatment and guidance apparatus 102 may be managed in various ways. FIG. 3 shows a record (or case report) of medical instructions that had been presented on a mobile device during use for administering medical treatment. This information may be communicated to a database (e.g., via the server 60) and used by the management system 10 for updating inventory status of the portable medical treatment and guidance apparatus and taking action (e.g., reordering medical items, notifying inspectors to confirm usage, etc. as described with reference to FIG. 1 above).

Figure 2B:
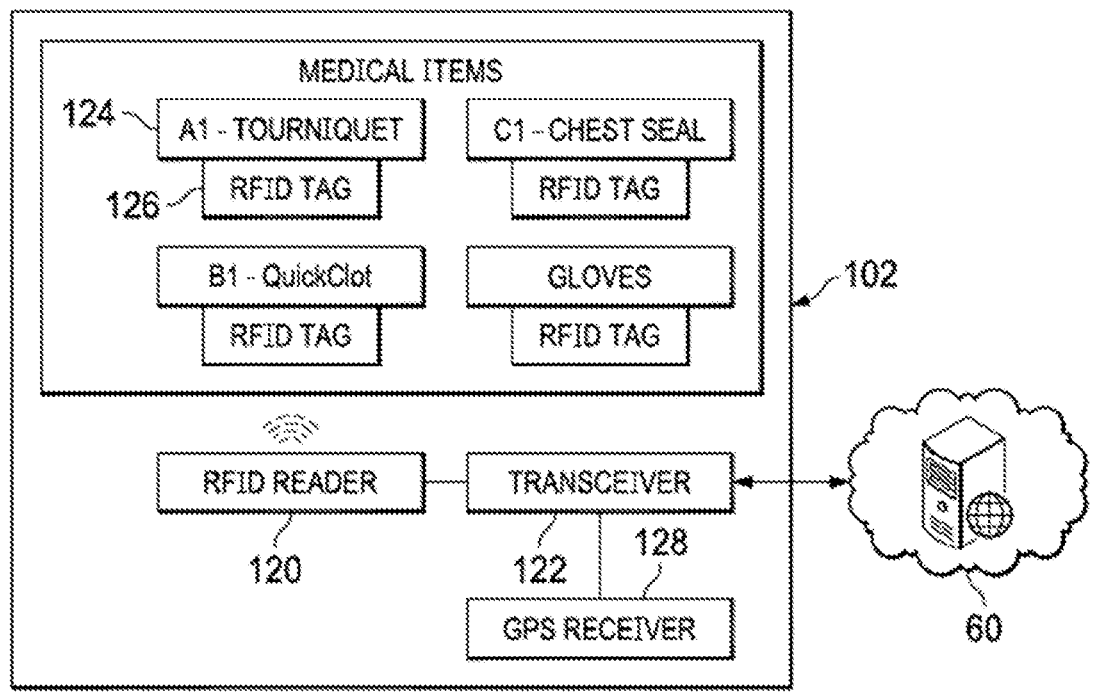

In some implementations, as shown in FIG. 2B, the portable medical treatment and guidance apparatuses 102 itself may include radio frequency (RFID) readers 120 to detect when a medical item is removed from the treatment and guidance apparatuses 102 and communicate this information with the database (e.g., via the server 60) using a transceiver 122. For example, each medical item 124 within the treatment and guidance apparatus 102 may include an RFID tag 126 on the packaging of the medical item.

In some examples, when the medical item 124 is inside the treatment and guidance apparatus 102 (or within a radius to the treatment and guidance apparatus 102 as defined by a range capability of the RFID reader 120), the RFID reader 120 transmits a "present" indication to the transceiver 122 for transmitting to the database that the medical item 124 is present in the treatment and guidance apparatus 102. In some examples, when the medical item 124 (and RFID tag 126) is moved outside of the RFID radius, the RFID reader 120 transmits a "not present" indication to the transceiver 122 for transmitting to the database that the medical item 124 is not present in the treatment and guidance apparatus 102. The information transmitted to the database may also include identification information of the medical device (e.g., serial numbers of the medical item, expiration dates of the medical item, etc.) and identification information of the treatment and guidance apparatus 102 (e.g., serial number, GPS location, etc.). For example, GPS location may be determined by the GPS receiver 128, encoded into a signal, and transmitted to the database via the transceiver 122. In some cases, cellular or network triangulation is used by the GPS receiver in GPS-denied communication areas.

The inventory status is then managed by the database as described above. For example, upon receiving an indication that the medical item 124 is not present in the treatment and guidance apparatus 102, the management system 10 may transmit a notification to one or more inspectors within a radius of the treatment and guidance apparatus 102 (e.g., all inspectors within 200 feet of the treatment and guidance apparatus 102 as determined by the GPS receiver 128). In some examples, the database stores a record of whether the medical item 124 is "present" or "not present."

FIGS. 2A and 3 show a mobile device 104 (e.g., a smartphone) configured to execute/run an application (also referred to herein as an "app") for providing instructions to a caregiver for administering medical treatment using the portable medical treatment and guidance apparatus 102. For example, the mobile device 104 can run an application (e.g., ZOLL Mobilize Rescue App) to provide real-time instructions (i.e., during the medical treatment) to help caregivers assess, manage, and treat victims/patients in emergency situations.

In the example shown, the application presents an image of a human body on a user interface 106 and waits for a response from a caregiver. The instructions are provided visually via the display or user interface 106 of the mobile device 104 and/or, in some instances, audibly via one or more speakers of the mobile device 104. The user interface 106 is part of a user interface of the mobile device 104 for presenting information and receiving input. The instructions include one or more questions (or queries) 152 (see FIGS. 4A-4C) so the real-time instructions can be determined based on the caregiver's response to the query. Goals of the queries include (i) assessing a medical need of the patient, (ii) guiding the caregiver to retrieve the appropriate medical items from the portable medical treatment and guidance apparatus 102, and (iii) instructing or guiding the caregiver to perform medical treatment using the medical items.

Components of the mobile device 104 include the components of the example mobile computer device 1850 described in context of FIG. 24. Accordingly, the caregiver subsequently presses on the user interface 106 (i.e., provides an input to the mobile device 104 via a user interface) in a region of the human body that represents where the patient is bleeding. Once the location is determined, the mobile device 104 is configured to present instructions for administering the medical treatment appropriate for the selected location.

FIGS. 4A-4D show an example sequence of real-time instructions presented to the caregiver using the mobile device 104. The sequence is shown when it has been determined that the victim is suffering from substantial bleeding. For example, FIG. 4A shows the user interface 106 of the mobile device 104 presenting a single query 152 to the caregiver after it has been determined that the victim is suffering from substantial bleeding (e.g., from a previous query). The query 152 displays the query: "Is the victim bleeding badly." In some embodiments, the query is presented in other languages (e.g., French, Spanish, etc.). In some cases, the language depends on a location of the mobile device 104, settings of the mobile device 104, or a previous query indicating a language preference. In some embodiments, the speaker of the mobile device 104 announces the query 152 in addition to, or instead of, the displayed query 152.

Figure 4D:
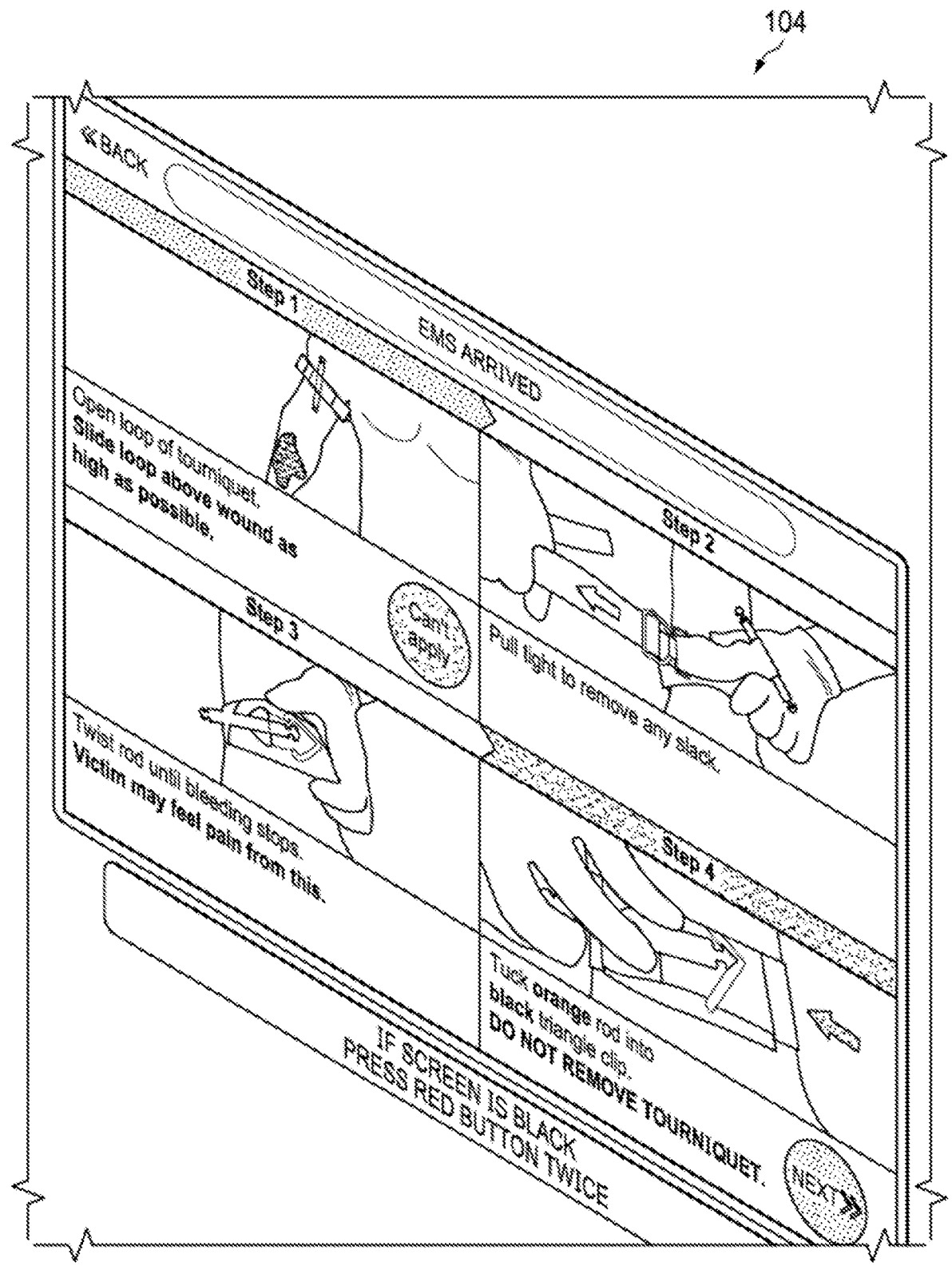

The display also shows a color illustration of a bleeding human body 154. A goal of the illustration is to aid the caregiver in understanding the query. This benefits caregivers who do not understand the displayed and/or audible queries. The display includes a set of responses 156. In the case shown in FIG. 4A, the set of responses 156 include "YES" and "NO." When the caregiver presses "YES" on the display, the question 152 changes to "Touch where victim is bleeding worst," as shown in FIG. 4B. The illustration 154 also changes to a front and back view of a human body. The caregiver presses a region 158 where the victim appears to be bleeding the worst. In response, the question 152 changes to an instruction asking the caregiver to "Locate tourniquet labeled 'Tourniquet A1,'" as shown in FIG. 4C. The caregiver would then open the portable medical treatment and guidance apparatus 102 and locate the Tourniquet A1. Once the caregiver has found the Tourniquet A1, the caregiver would press "Next" 160. In response, the display would change to detailed guidance and instructions on administering the medical aid to the patient, as shown in FIG. 4D. During use, the caregiver would follow the guidance and instructions to administer the medical aid to the patient. In the event that another medical item is needed, the display would change to instruct the caregiver to locate the medical item within the portable medical treatment and guidance apparatus 102.

FIG. 5 shows a screenshot 200 of a summary record of the selections that were made while the application was running on the mobile device 104. As discussed herein, the mobile device 104 is configured to present instructions 202 for administering treatment to the patient. The mobile device 104 is also configured to wait for user input and display received input 204 in response to each presented instruction 202. In some implementations, the screenshot 200 represents a time after the treatment has occurred. For example, the application can present a case report or summary of the administered medical treatment. The mobile device 104 is also configured display the time 208 associated with each medical instruction on the user interface 106. Such information is helpful for assessing the sequence of events that took place during a prior emergency situation. The user input included in the case report can be inferred from user input (e.g., touch points, keystrokes, gestures, etc.) via the mobile device 104. For example, as discussed herein, when the app provides an instruction for the user to remove and use a medical item from the portable treatment and guidance apparatus 102, then the app may generate a record that the item was removed. This record may be used by a manager to confirm that the item was indeed removed and needs to be replaced, and/or may automatically trigger the management system to note in the database that the particular treatment and guidance apparatus is in need of servicing. This servicing-needed note may further trigger the management system to pre-order the item, without need for actual user intervention.

In some implementations, the case report includes information on the usage of medical items/equipment. For example, in the situation shown in FIG. 5, the caregiver was instructed 206 to "put on gloves." The case report maintains a record of this instruction and can be used to infer which medical items/equipment need to be replaced or restocked. The case report can be transmitted to a database for inventory management via communication capabilities (e.g., Wi-Fi, 3G/4G/5G, etc.) of the mobile device 104. Aspects of the inventory management system include automatic re-ordering of the used inventory. Functionality of the inventory management will be described in further detail below.

In some implementations, the case report is automatically sent to a database when the medical treatment is complete. In some implementations, the case report is sent to the database immediately upon receiving a first instruction to administer medical treatment. When the mobile device 104 is in communication with the database, such a transmission may occur during the medical event (i.e., during usage of the app). In some implementations, the case report is sent to the database in periodic intervals of time (e.g., every 5 seconds, every 30 seconds, etc.). In some implementations, the case report is sent to the database after a period of inactivity such as when the user has not responded to a medical instruction by providing input within a certain amount of time (e.g., within 1 minute). In some implementations, the case report is triggered to be sent to the database by one or more actions (e.g., immediately after each touch input is received or keystroke is received by the mobile device 104).

In some implementations, the application receives via the user interface 106 a confirmation that a particular medical item was used as part of providing the medical treatment. For example, in the above-noted case, the application could prompt the user to confirm that gloves were in fact used. This confirmation can then be included in the generated case report. This way, inclusion of such a confirmation may relieve a manager of the treatment and guidance apparatus from actually having to check the physical apparatus to see whether the item indeed needs to be replaced.

In some implementations, the mobile device 104 runs an application in a management mode that prompts a user (or inspector) to indicate which portable medical treatment and guidance apparatus is being managed. For example, the application can associate the specific portable medical treatment and guidance apparatus with a database of inventory information. Furthermore, knowledge of missing medical items within a portable medical treatment and guidance apparatus can be transmitted to the database for indicating that the missing medical items needs to be replenished. For example, if the application determines that nitrile gloves should be present but are not, the application may prompt the user to replenish nitrile gloves (e.g., from a stock room), may automatically purchase nitrile gloves from a medical device supplier, or may transmit this information to the database or a remote computational device for further processing. Such functionality aids the inspector in determining which medical items have been used, especially when it may not be apparent to the inspector which medical items are missing.

In some implementations, the mobile device 104 runs an application that prompts a user to indicate which portable medical treatment and guidance apparatus is being used to provide medical treatment. Such information is used by the application to determine which medical treatment can be provided using the particular portable medical treatment and guidance apparatus. For example, if the application knows that the portable medical treatment and guidance apparatus specifically being used is the portable medical treatment and guidance apparatus 102, that the application will know that a 15 mg dose of Insta-Glucose is not readily available and that a user may need to seek a different nearby portable medical treatment and guidance apparatus if Insta-Glucose is required for the medical treatment. This saves precious time during medical treatment if this is known in advance since the application can assist in directing the user to a nearby portable medical treatment and guidance apparatus containing all the necessary medical items/equipment.

In some implementations, the application identifies the type of portable medical treatment and guidance apparatus is being used by prompting a user 302 (see FIG. 6) of the mobile device 104 to capture an image of the portable medical treatment and guidance apparatus or an identifying feature (e.g., QR code) associated with the portable medical treatment and guidance apparatus using at least one camera of the mobile device 104. The user interface 106 of the mobile device 104 may provide instructions on how to use the camera of the mobile computing device 104 for capture an image of the at least one medical item. For example, the user interface 106 may instruct the user to take an image of the outside packaging, identifying feature (e.g., QR code, UPC barcode, etc.) or logo of the portable medical treatment and guidance apparatus, then take a second image of the contents within the portable medical treatment and guidance apparatus. In some implementations, the instructions include instructing a user to take an image of one or more medical items and/or barcodes (e.g., QR codes, UPC barcodes, etc.) associated with one or more medical items within the portable medical treatment and guidance apparatus.

Apart from using the mobile device 104 to present medical instructions and receive input as described in relation to FIGS. 4A-4D and FIG. 5, the mobile device 104 may also be configured to capture images of medical items within the portable medical treatment and guidance apparatuses 102 and analyze or otherwise communicate inventory information of the treatment and guidance apparatus 102 to the database (e.g., if a medical item missing from the treatment and guidance apparatus 102 based on an analysis of the image that identifies what medical items are present or absent from the treatment and guidance apparatus 102, the database should be updated to indicate that the portable medical treatment and guidance apparatuses 102 does not have the medical item). For example, in some cases, feature recognition is used (e.g., by the mobile device 104 or by a remote server) to identify the medical items within the portable medical treatment and guidance apparatus 102 (e.g., using edge detection algorithms on the image acquired using the mobile device 104) and matching all identified medical items to a template (e.g., a known database of shapes, sizes, colors, recognized text, etc.) to determine which medical items that are present. If it is known that a particular medical item should be present (e.g., from the inventory database) but is not detected in the image, the system may determine that the medical item may be missing, and in some cases, may optionally generate a record or notification for an inspector to confirm that the item is missing. Further details of this image recognition process are described in an example with respect to FIGS. 6 and 7.

FIG. 6 shows a network 300 where the user 302 is capturing and transmitting an image taken of the medical items within the portable medical treatment and guidance apparatus 102. In some implementations, the camera instructions include positioning the camera of the mobile device 104 such that all medical items within the portable medical treatment and guidance apparatus 102 are located within a field of view 304 of the camera. The image is then processed by one or more processors of the mobile device 104 or a server 306 to determine the specific portable medical treatment and guidance apparatus and/or the medical items present or absent from the treatment and guidance apparatus in the image.

The server 306 includes one or more computational devices configured with one or more processors to execute computer instructions. The server 306 includes the components of the computer device 1800 described with reference to FIG. 24. The server 306 is communicatively coupled to a database that stores identifying status information and inventory information for one or more portable medical treatment and guidance apparatuses. The server 306 is part of a medical treatment and guidance apparatus management system that also includes a user interface configured to provide a status indication of the plurality of portable medical treatment and guidance apparatuses based on the status information.

Computational devices (e.g., a second mobile device 308a, a laptop computer 308b, etc.) other than the mobile device 104 may be used to manage, via a communication link 310, the database of inventory information. For example, the laptop computer 308b may be in communication with the server 306 via the Internet, and database information associated with the server 306 can be queried and/or updated by the laptop computer 308b.

In some implementations, the user 302 is prompted to take an image of the outside packaging, identifying feature (e.g., QR code), or logo of the portable medical treatment and guidance apparatus, so as to collect identification information of the treatment and guidance apparatus. When the server 306 is used to perform the processing, the mobile device 104 transmits this image and/or other identification information to the server 306, where the server 306 searches the database for a closest match between the identification information (e.g., captured image, device ID) and known identification information (e.g., known images, existing device ID) of portable medical treatment and guidance apparatuses. Alternatively, or in addition, the closest match can be inferred from image processing such as using information of detected edges in the image, color information, and contrast information. For example, the processor(s) can perform letter or word recognition by using the detected edges of a logo to convert pixel information of the image into a letter or word that can be compared with known letters or words associated with known portable medical treatment and guidance apparatuses. Or, as discussed herein, the mobile device 104 may capture identification information in addition to and/or other than images to accurately identify the particular treatment and guidance apparatus.

In the implementation described above and shown in FIG. 6, the user or inspector 302 is prompted to take an image of the inside contents of the portable medical treatment and guidance apparatus 102. The mobile device 104 transmits this image information to the server 306, where the server 306 searches the database for a closest match between the captured image and known images of portable medical treatment and guidance apparatuses. The closest match can be inferred from image processing (or image recognition) such as using information of detected edges in the image, color information, and contrast information. The closest match is then sent back to the mobile device 104 for further processing.

these are configured to execute these actions and communicate directly with the database. For example, in some situations, information is described as being transferred from the mobile device 104, to the server 306, back to the mobile device 104, and then sent to the database. But in general, this information can flow in various directions. And the user or inspector 302 is able to interfere and override the information being retrieved and updated in the database at any time.

Regarding the image processing, the processor(s) can perform letter or word recognition to determine which groups of medical items are present. The group determination can be confirmed or corrected using color information. A database maintains information on which group (and associated color) is present (or should be present) within each portable medical treatment and guidance apparatus. A listing of medical item identifying information including, but not limited to, with part names, part numbers, group and label identifiers, color information, and expected quantity within a certain portable medical treatment and guidance apparatus maintained by the database is shown in Table 1 below. But as will be described in further detail later, the database may also maintain a record of expiration information, usage information, readiness information, and location information.

TABLE 1

| Part No. | Part Name | Group/Label | Color | Quantity |
|---|---|---|---|---|
| P001 | SOF Tactical Tourniquet-Wide, Orange | A1 | Red | 4 |
| P002 | QuickClot Bleeding Control Dressing (3" × 4") | B1 | Yellow | 2 |
| P003 | 6" Flat Emergency Trauma Dressing (ETD) | B2 | Yellow | 2 |
| P004 | HyFin Chest Seal | C1 | Green | 2 |
| P005 | CPR Face Shield with Bite Block | D1 | Blue | 1 |
| P006 | 12 mg Dissolvable Allergy Tablets (Box) | E1 | Pink | 1 |
| P007 | 81 mg Chewable Aspirin (Bottle) | E2 | Pink | 1 |
| P008 | 15 mg Tube of Insta-Glucose | E3 | Pink | 1 |
| P009 | 36" SAM Emergency Splint | F1 | Gray | 1 |
| P010 | Sterile Multi-trauma Gauze Dressing (10" × 30") | F2 | Gray | 2 |
| P011 | 5" × 9" Sterile Gauze (Combine ABD pads) | F3 | Gray | 4 |
| P012 | Sterile Conforming Stretch Gauze (4.5" × 4 yd) | F4 | Gray | 2 |
| P013 | Biohazard Bag | F5 | Gray | 2 |
| P014 | Antiseptic Sanitizing Hand Wipes (Antiseptic Toilettes) | F6 | Gray | 2 |
| P015 | Emergency Space Mylar Blanket | F7 | Gray | 2 |
| P016 | 4" × 5" Cold Compress (Ice Pack) | F8 | Gray | 1 |

For example, in the context of administering medical treatment, this information may be used to tailor the instructions for providing medical treatment for the specific portable medical treatment and guidance apparatus being used. For example, the medical instructions may be adjusted to reflect the current inventory of available items of the portable medical treatment and guidance apparatus, so that certain instructions would be presented and/or modified when the appropriate inventory is available. In the context of inventory management, this information is used to update a database of inventory information, as noted herein. In some implementations, both medical treatment and inventory management functions are performed substantially concurrently.

The case report may also include identifying information of the specific portable medical treatment and guidance apparatus is being used and also information related to the one or more images captured by the camera.

While this specification refers to specific actions being taken by the mobile device 104 and the server 306, either of For example, if the server 306 determines that Group A1 is present (by using character recognition and color information), the server 306 can filter out portable medical treatment and guidance apparatuses that do not include Group A1. This process can continue until the server 306 uniquely identifies the type of portable medical treatment and guidance apparatus that the image represents (e.g., portable medical treatment and guidance apparatus 102).

In some implementations, once the server 306 determines the type of portable medical treatment and guidance apparatus, the server 306 determines which medical items are missing. For example, in the context of Table 1 above, if the server 306 determines that medical items associated with Groups A1, B1, B2, D1, E1, E2, E3, F1, F2, F3, F4, F5, F6, F7, and F8 are present but it cannot identify Group C1 in the image, it may assume that Group C1 is missing and may request that the medical items associated with Group C1 be replenished. In this situation, the server 306 transmits a request back to the particular mobile device 104 that is used for managing the treatment and guidance apparatus (could be different than the mobile device that is used during the actual medical emergency event) to prompt the inspector 302 to replenish the missing medical items. In some implementations, the mobile device 104 transmits this information to the database for restocking.

In some implementations, an identification marking associated with each medical item may be used to determine the medical items present or missing within a portable medical treatment and guidance apparatus. The identification marking associated with the portable medical treatment and guidance apparatus or the medical items may include a text serial number, or graphical encoding scheme such as a bar code, or a QR code. For example, some implementations include a QR code identifying the medical item positioned underneath each medical item. When the medical item is removed from the portable medical treatment and guidance apparatus, the QR code becomes visible. When the camera instructs the image to be taken, the application identifies all barcodes visible within the field of view 304 of the camera and transmits this information to the database. In another example, the QR code is located on a spring-loaded hinged flap at the top of the storage well holding the particular medical item. The medical item maintains the spring load resulting in the QR code being hidden from view. When the medical item is removed, the flap extends upward towards the top surface of the storage container, thus causing the QR code to become visible and presented in a manner more suitable for scanning thereof.

In this way, identifying information of a first graphical encoding scheme marking (obtained by the at least one camera of the mobile device 104) of the housing of the portable medical treatment and guidance apparatus is transmitted to the server 306. The mobile device 104 instructs the server 306 to perform a query of the database for a match between the identifying information contained in a first bar code marking and a list of identifying information associated with respective portable medical treatment and guidance apparatuses. Once a match is found, the identifying information associated with the match is retrieved from the database and transmitted back to the mobile device 104 for further processing. The identifying information identifies the portable medical treatment and guidance apparatus by type or uniquely by serial, inventory, or part number.

Similarly, identifying information of a second graphical encoding scheme marking (obtained by the at least one camera of the mobile device 104) associated with a medical item of the portable medical treatment and guidance apparatus is transmitted to the server 306. The mobile device 104 instructs the server 306 to perform a query of the database for a match between the identifying information of a second graphical encoding scheme marking and a list of identifying information associated with respective medical items. Once a match is found, the identifying information associated with the match is retrieved from the database and transmitted back to the mobile device 104 for further processing. The identifying information identifies the medical item by type or uniquely by serial, inventory, or part number.

FIG. 7 shows a flowchart 400 of the steps performed by the mobile device 104 or the server 306. In some implementations, an image of the camera is used by the server 306 or mobile device 104 to determine 402 first identifying information of the portable medical treatment and guidance apparatus (e.g., the type of the portable medical treatment and guidance apparatus), which is identified in FIG. 7 as the "medical triage apparatus system." The camera is also used for the server 306 or mobile device 104 to determine 404 second identifying information of at least one medical item of the plurality of medical supplies within the portable medical treatment and guidance apparatus (e.g., identifying that a specific medical item is missing). An inventory report can be generated 406 representing an inventory of the medical treatment and guidance apparatus system and this inventory report can be transmitted 408 to the server 306 associated with the database (if the server 306 itself did not generate 406 the inventory report). In this way, the inventory report can be based on the first identifying information and the second identifying information.

In some implementations, the application may prompt the user or inspector 302 to take subsequent images of specific areas within the field of view 304. The subsequent images can be used to confirm medical items or visible barcodes.

Transmitting the inventory report can be triggered when the user or inspector 302 requests the transfer of the inventory report via the user interface 106 of the mobile device 104, or automatically after the mobile device 104 (or the server 306) determines which medical items are present and which medical items are missing from the portable medical treatment and guidance apparatus.

In some implementations, the first identifying information includes expiration information of the portable medical treatment and guidance apparatus. In some implementations, the second identifying information includes expiration information of the at least one medical item of the portable medical treatment and guidance apparatus.

In some implementations, a first bar code marking is attached to the housing of the portable medical treatment and guidance apparatus and the first identifying information is associated with the first bar code. In some implementations, a second bar code marking is located within at least one compartment of the medical treatment and guidance apparatus system and the second identifying information is associated with the second bar code.

In some implementations, the user or inspector 302 may manually override the results of the server 306 or database. For example, the inspector 302 may notice that nitrile gloves are present but blocking a group identifier despite the application determining that they are missing. In this situation, the inspector 302 can specify that the nitrile gloves are in fact present. In a broader context, the application may present the results of the inventory to the inspector 302 for confirmation before transmitting the inventory information to the database. Upon review, the inspector 302 may override the inventory information of one or more medical items so the inventory report transmitted to the database is accurate of the current inventory of the portable medical treatment and guidance apparatus 102.

The mobile device 104 is also configured to retrieve current inventory status from the database for cross-checking against actual inventory of the portable medical treatment and guidance apparatus as confirmed by the inspector 302. For example, once the application knows the identity of the portable medical treatment and guidance apparatus, it can retrieve inventory information associated with the specific portable medical treatment and guidance apparatus. This is useful when hundreds of portable medical treatment and guidance apparatuses may exist within a building. A unique barcode or other identifier associated with each portable medical treatment and guidance apparatus can be transmitted to the server 306 for querying the database to determine the inventory for the particular portable medical treatment and guidance apparatus.

FIG. 8 shows instructions and associated user input options on a mobile device for administering treatment using a portable medical treatment and guidance apparatus. In the implementation shown in FIG. 8, the user interface 106 of the mobile device 104 presents a series of medical instructions 502 to a caregiver during medical treatment using the mobile device 104. In response, the caregiver is given the choice to either respond "OK" 504 or "SKIP" 506. The response of the caregiver is used to infer inventory information. For example, in the example shown in FIG. 8, if the caregiver responds "SKIP" 506, it is assumed that Aspirin was not administered. In other words, the mobile device 104 is configured to present via the user interface 106 instructions for administering a dosage quantity as part of the medical treatment, and receive via the user interface 104 an administered dosage quantity. The response of the caregiver is recorded and included in the case report that is generated and transmitted to the database.

FIG. 9 shows instructions and associated user input options on a mobile device for managing inventory using a portable medical treatment and guidance apparatus. In the implementation shown in FIG. 9, the user interface 106 of the mobile device 104 presents a series of inventory questions 602 to an inspector using the mobile device 104. In response, the inspector is given the choice to either respond "FULL" 604, "HALF" 606, or "EMPTY" 608. The response of the inspector is used to confirm and/or update inventory information. For example, in the example shown in FIG. 9, if the inspector responds "HALF" 606, it is assumed that approximately half a supply (e.g., half a bottle of 50 tablets when full) of Aspirin is present in the portable medical treatment and guidance apparatus. If the inspector responds "FULL" 604, this is confirmation that the supply of Aspirin is approximately full. If the inspector responds "EMPTY" 608, this is confirmation that the supply of Aspirin is approximately empty. However, three levels of granularity is purely an example. In some implementations, five levels of granularity is provided (e.g., full, ¾ full, ½ full, ¼ full, and empty). In some implementations, 20 levels of granularity is provided in the form of a progress bar or pie chart. In these situations, the inspector swipes their finger to denote an approximate level of supply.

The response of the inspector is recorded and included in the inventory report that is generated and transmitted to the database. When this confirmation contradicts the information present in the database, the database is updated with the inspector's confirmation. For example, the database may indicate that the Aspirin is "HALF," but the inspector responds that the Aspirin is "EMPTY." In this situation, the database is updated to reflect that the Aspirin is "EMPTY."

In some implementations, an automatic reordering of supply is triggered by the server 306 when any entry of the database is changed to "EMPTY." In other words, in some cases, the server 306 is configured to initiate a replenishment of at least one medical item associated with the medical treatment and guidance apparatus system when an inventory report is received and a quantity of the at least one medical item is below a replenishment threshold. In some implementations, the replenishment threshold is "HALF", meaning that when a quantity less than "HALF" exists a replenishment is triggered.

In some implementations, it is helpful to denote an actual quantity of supply. As shown in FIG. 9, the user interface 106 of the mobile device 104 presents an inventory question 610 asking the inspector to confirm the glove quantity. In response, the inspector is given the choice to either respond "4" 612, "2" 614, or "0" 616. The response of the inspector is used to confirm and/or update inventory information. The response of the inspector is recorded and included in the inventory report that is generated and transmitted to the database. When this confirmation contradicts the information present in the database, the database is updated with the inspector's confirmation. In some implementations, the replenishment threshold is a quantity of two, meaning that when one exists a replenishment is triggered.

In some implementations, it is helpful to include battery charge levels of the portable medical treatment and guidance apparatus itself, or one or more medical items within the portable medical treatment and guidance apparatus. For example, in some implementations a battery associated with the portable medical treatment and guidance apparatus can die and limit the functionality of the portable medical treatment and guidance apparatus. In cases where a battery is known to be present in the portable medical treatment and guidance apparatus, the user interface 106 can ask the inspector a question 618 regarding the remaining battery charge. In response, the inspector is given the choice to either respond "100%" 620, "50%" 622, or "0%" 624. The response of the inspector is used to confirm and/or update battery charge information. The response of the inspector is recorded and included in the inventory report that is generated and transmitted to the database. For example, if the battery is below a charge threshold (e.g., 50%), the database may indicate that a charge is necessary.

FIG. 10 shows a portable medical treatment and guidance apparatus 700 for treating medical emergencies with a removable tablet device 702. Examples of such portable medical treatment and guidance apparatuses 700 are the Mobilize Mobile Rescue System developed by ZOLL Medical Corporation of Chelmsford, Massachusetts. Each portable medical treatment and guidance apparatus 700 includes a case 704 (i.e., a housing) with a plurality of medical supplies 706 (or medical items) for administering medical treatment (e.g., but not limited to, 4×SOF-T Wide tourniquet, 2× QuikClot bleeding control dressing, 2×6" flat emergency trauma dressing, 2× Hyfin chest seal, 2× Water-Jel universal burn dressing, 2× triangular bandage, 2×4.5" sterile conforming stretch gauze, 4×5"×9" sterile combine ABD pads, 2×10"×30" sterile multi-trauma dressing, a 36" SAM emergency splint, 2×4" elastic wrap bandage, a 4"×5" cold compress, an adhesive tape 2.5 yd, a CPR face shield with bite block, a 81 mg chewable aspirin (bottle), a 12 mg dissolvable allergy tablets (box), a 15 mg Insta-Glucose, 2× emergency space Mylar blanket, a portable charger and charging cord, a USB charging cube, an inspection card, 12× proof seals, 2× bag with biohazard markings, a pair of trauma shears, 10× nitrile gloves, a user manual and inventory card, 2 eye pads, 16× adhesive bandages (assorted sizes), 10× burn cream packets, 10× triple antibiotic ointment packets, 10× antiseptic wipes, a pair of tweezers, 10× hand sanitizer packets, an eye wash, and a first aid guide). As with the portable medical treatment and guidance apparatus 100, the case 704 is a soft fabric material that includes a zipper to seal the portable medical treatment and guidance apparatus.

In some implementations, the portable medical treatment and guidance apparatus 700 includes one or more RFID readers similar to, or the same as, the RFID readers 120 of the portable medical treatment and guidance apparatus 102 described with reference to FIG. 2B. Similarly, each of the medical items may include an RFID tag readable by the RFID readers of the portable medical treatment and guidance apparatus 700.

The removable tablet device 702 is a computer device that includes the components of the computer device 1850 as described with reference to FIG. 24. The tablet device 702 is housed within the case 704 of the portable medical treatment and guidance apparatus 700. The tablet device 702 is essentially the mobile device 104 with a larger display or user interface for user input. The same functionality of the mobile device 104 is included in the tablet device 702 (e.g., touch inputs, user interface, audio capabilities, etc.). A difference is that the portable medical treatment and guidance apparatus 700 includes the tablet device 702 while the portable medical treatment and guidance apparatus 100 uses a separate mobile device 104. The tablet device 702 is configured to run a version of the application previously described (e.g., the ZOLL Mobile Rescue App) to provide real-time instructions (i.e., during the medical treatment) to help caregivers assess, manage, and treat victims/patients in emergency situations. In some implementations, the tablet device 702 can be detached, removed, and replaced with an alternate tablet device that is configured to run the application.

FIG. 11 shows a screen shot 800 of the application running on the display or user interface of the tablet device 702. The screen shot 800 includes a summary record of medical instructions 802, user input in response to the medical instructions 804, and associated date stamp 806 and time stamp 808.

In an implementation where the tablet device 702 is included and provided with the portable medical treatment and guidance apparatus 700, a battery level of the battery of the tablet device 702 needs to be monitored. As an extreme example, the energy level of a battery of the portable medical treatment and guidance apparatus 700 may be substantially depleted over time while in storage. Then when needed in a medical emergency, due to the depleted battery, the tablet device 702 might not be able to turn on, essentially leaving the caregiver to determine the next steps on their own. Two solutions are implemented to cure this problem. The first solution is to monitor the battery level of the battery via the database and instruct an inspector or user to manually charge the portable medical treatment and guidance apparatus 700. The second solution is to allow caregivers to use their own mobile device (e.g., mobile device 104) to provide instructions for administered medical treatment with the portable medical treatment and guidance apparatus 700.

In certain embodiments, the battery level of the tablet device 702 can be monitored as follows. The portable medical treatment and guidance apparatus 700 is opened and the tablet device 702 is turned on to perform an initial setup. The initial setup includes connecting the tablet device 702 to a wireless network (e.g., the local area network of a building using Wi-Fi, a cellular network using 3G/4G/5G LTE, etc.). The tablet device 702 is setup to communicate with the database (e.g., by entering credentials to access the server 306 which may be secured). The tablet device 702 is charged to ensure the battery is approximately 100% full. The tablet device 702 is then ready for use and the case 704 of the portable medical treatment and guidance apparatus 700 is closed and stored for use by caregivers.

The tablet device 702 is configured to periodically self-report or transmit battery level information of the battery of the tablet device 702 to the database over the network. For example, self-reporting can occur once per day, once per hour, or any other suitable time interval. Some implementations include locational information (e.g., the current global positioning system (GPS) position of the portable medical treatment and guidance apparatus) along with the battery level information to the database. The database includes a record of the battery level history and current battery level, as well as location history and current location of the portable medical treatment and guidance apparatus 700. When the battery level is below a threshold (e.g., below 20%), the server 306 is configured to provide an alert to charge the battery of the respective portable medical treatment and guidance apparatus. For example, in some implementations, the server 306 pushes an alert to mobile phones of inspectors in the area and provides charging instructions and location information about the portable medical treatment and guidance apparatus that needs to be charged. In the event that the battery dies, self-reporting will cease. The server 306 is configured to provide an alert that self-reporting has ceased and the battery is most likely dead or the portable medical treatment and guidance apparatus has been disconnected from the network. This prompt will request the immediate attention of inspectors. Last known location information of the portable medical treatment and guidance apparatus is provided with this alert.

As mentioned above, the case 704 includes a zipper to seal the portable medical treatment and guidance apparatus. In some implementations, the seal is a tamper seal that is broken the first time the portable medical treatment and guidance apparatus 700 is opened. In some implementations, the tamper seal is a physical component, such as a paper tag that is irreversibly broken when the seal is first broken. An inspector viewing the portable medical treatment and guidance apparatus 700 would be able to see the tamper seal has been broken and that the portable medical treatment and guidance apparatus has been tampered with or otherwise accessed. When such a situation occurs, the inspector may be motivated to check on the contents of the treatment and guidance apparatus 700 to see whether it needs servicing (e.g., inventory replenishment for particular items that are missing). Or, when it is desired that the treatment and guidance apparatus be accessed, for example, for the battery to be charged, then the inspector could check to see that the tamper seal has not been broken and would be able to infer that the tablet has likely not been properly charged. The inspector can note this in the database and/or perform the necessary servicing steps. In various embodiments, the portable medical treatment and guidance apparatus 700 will periodically self-report the battery level of the tablet device 702 as previously described.

In some implementations, the tamper seal is electronic and monitored by a sensor built-in to the case 704 that senses when the seal is broken. A processor connected to the sensor records the signals from the sensor and stores a record when the seal is broken. If the processor determines that the seal has been broken at a time when the treatment and guidance apparatus was not expected to be accessed, then a notification may be sent so for an inspector to check on the contents of the treatment and guidance apparatus to see whether it needs servicing (e.g., inventory replenishment for particular items that are missing). Or, when it is desired that the treatment and guidance apparatus be accessed, for example, for the battery to be charged, then the processor may determine that the tamper seal has not been previously broken, and it is assumed that the portable medical treatment and guidance apparatus has not been opened or otherwise accessed. This information may be used to infer that the tablet has likely not been accessed; in some cases, such access is desirable for the battery of the tablet to be properly charged. In some implementations the processor can communicate with the server 306 to indicate that the tamper seal has not been broken and that a charge is needed. The device has a WiFi communications circuit that is powered on when the unit is plugged in for charging, as discussed further below.

In some implementations, a charging cable for the tablet device 702 is provided external to the zipper seal that seals the components the portable medical treatment and guidance apparatus 700, but within a tamper seal. For example the charging cable may be located within a pocket defined by the zipper seal and a tamper seal. In this situation, the zipper seal functions to seal the portable medical treatment and guidance apparatus 700, and the tamper seal functions to determine if the charging cable was used. In some implementations, the tamper seal is a physical tag, so it is an inspector viewing the portable medical treatment and guidance apparatus 700 who would be able to see the tamper seal has not been broken and would be able to infer that the tablet device 702 has likely not been properly serviced and that the battery of the tablet device 702 is in need of a charge. The inspector can break the tamper seal to charge the battery of the tablet device 702 without having to open the seal to the portable medical treatment and guidance apparatus 700. In some implementations the tamper seal is electronic as noted above and the processor of the tamper seal can communicate with the server 306 to indicate that the tamper seal has not been broken and that a charge is needed.

In some implementations, the tamper seal is communicatively coupled to the tablet device 702. This communication setup can be setup at the factory when the portable medical treatment and guidance apparatus 700 is assembled. For example, tamper seal information (i.e., untampered or tampered), can be included in the information sent by the tablet device 702 to the database such as the case report and inventory report.

In some implementations, current tamper seal information along with the current GPS location of the portable medical treatment and guidance apparatus 700 is transmitted to the database periodically. In some implementations, the server 306 analyzes this information along with the case report to determine a status of the portable medical treatment and guidance apparatus 700. For example, location information may be helpful to determine whether the treatment and guidance apparatus 700 has moved from its storage location, such as due to usage in a medical emergency or if it has been stolen or otherwise improperly accessed.

For example, the server 306 can determine if the portable medical treatment and guidance apparatus 700 moves based on the current location and location history of the portable medical treatment and guidance apparatus 700. If the server 306 determines that the portable medical treatment and guidance apparatus 700 has moved, an alert is sent to an inspector to check on the status of the portable medical treatment and guidance apparatus 700. The current location of the portable medical treatment and guidance apparatus 700 is included in this alert information so the inspector knows where to check.

In some implementations, the server 306 can determine if the portable medical treatment and guidance apparatus 700 moves and based on whether or not the tamper seal has been broken, alert the inspector accordingly. If the portable medical treatment and guidance apparatus 700 is moved but the tamper seal has not been broken, this may indicate the portable medical treatment and guidance apparatus 700 is being stolen and an alert may be sent to an inspector in the area to check on the status of the portable medical treatment and guidance apparatus 700.

The portable medical treatment and guidance apparatus 700 may be moved to perform a medical treatment. In this situation, the tamper seal may be broken (if not already) and a case report may be received by the server 306 to indicate that a medical treatment is occurring. Such information can be used to alert first responders in the area (or vicinity) of the portable medical treatment and guidance apparatus 700 that a medical event is taking place.

In another example, if the portable medical treatment and guidance apparatus 700 is reported to be opened (i.e., the tamper seal is broken), but no medical event is indicated (i.e., a case report is not received or is received but not indicative of a medical event occurring), the inspector can be alerted to check on status of the portable medical treatment and guidance apparatus 700 since it was opened but there was no medical event. This may indicate that someone is stealing medical items from the portable medical treatment and guidance apparatus 700 or that someone needs help. The current location of the portable medical treatment and guidance apparatus 700 may be included in this alert.

In some implementations, more than one tamper seal is used. For example, a first tamper seal indicates whether the battery charger has been used, while a second tamper seal indicates whether the portable medical treatment and guidance apparatus 700 itself has been opened. For example, if the first tamper seal is reported to be broken and the second tamper seal is reported to be not broken, a medical event is likely not occurring. However, if both seals are broken, then a medical event may be occurring. An alert to an inspector may be sent from the server 306 indicative of these events. The current location of the portable medical treatment and guidance apparatus 700 may be included in this alert.

However, despite the battery of the tablet device 702 being dead, the portable medical treatment and guidance apparatus 700 can still be used with another mobile device. For example, a caregiver can use his/her mobile phone to administer instructions as previously described with reference to the portable medical treatment and guidance apparatus 100. The functionality previously described regarding imaging recognition using the mobile device 104 is also applicable to the portable medical treatment and guidance apparatus 700.

FIG. 12 shows a network 900 where the user 302 is capturing and transmitting image information, identification information and/or inventory information of the medical items within the portable medical treatment and guidance apparatus 700 using the mobile device 104. As previously mentioned, this can be performed during a medical treatment (i.e., to provide instructions to the user 302 in the event that the tablet device 702 is not functioning properly, is in need of servicing or has died) or during inventory management (i.e., an inspector is confirming the quantity and status of the medical items within the portable medical treatment and guidance apparatus 700). A difference between the network 900 shown in FIG. 12 and the network 300 shown in FIG. 6 is that the tablet device 702 of the portable medical treatment and guidance apparatus 700 is included in the network 900.

Communication link 904 allows the tablet device 702 to communicate directly with the server 306 and database. This may be configured during setup of the tablet device 702. This functionality allows the tablet device 702 to be aware of the currently known inventory status of the portable medical treatment and guidance apparatus 700. This information allows the tablet device 702 to tailor medical instructions according to the inventory present and if needed, direct a caregiver to a nearby portable medical treatment and guidance apparatus that has a necessary medical item.

In some implementations, an application running on the mobile device 104 provides instructions for taking one or more images of the portable medical treatment and guidance apparatus 700 itself and the medical items within the portable medical treatment and guidance apparatus 700. This is substantially similar to the functionality described for portable medical treatment and guidance apparatus 100. In some implementations, the camera instructions tell the user to position the camera of the mobile device 104 such that all medical items within the portable medical treatment and guidance apparatus 700 are located within a field of view 902 of the camera. The image is then processed by one or more processors of the mobile device 104 or a server 306 to determine the specific portable medical treatment and guidance apparatus in the image and the specific medical items missing or present as previously described.

Where the portable medical treatment and guidance apparatus 700 includes one or more tamper seals, identifying information from the server 306 can indicate whether the tamper seal has been broken or has not broken (i.e., has it been previously opened). This information can be useful to confirm the functionality of the tamper seal. For example, a situation could arise where the tamper seal is not functioning properly and has not transmitted information to the database that the tamper seal has in fact been broken. An inspector checking the status of the portable medical treatment and guidance apparatus 700 would receive an indication that the tamper seal is supposedly untampered and would become aware of this and may resolve the issue by replacing the tamper seal or by manually overriding the database. In this situation, the first identifying information received by the server 306 can include information on whether a first seal is broken.

Computational devices (e.g., a second mobile device 308*a*, a laptop computer 308*b*, etc.) other than the mobile device 104 or tablet device 702 may be used to manage, via the communication link 310, the database of inventory information. For example, the laptop computer 308*b* may be in communication with the server 306 via the Internet, and database information associated with the server 306 can be queried and/or updated by the laptop computer 308*b*.

Regarding the battery level information, in some implementations, the identifying information received from the server 306 includes information on whether the battery within the portable medical treatment and guidance apparatus system needs replacement. For example, the battery may not be holding charge sufficiently or the battery has reached the end of its service life. The database may also indicate an expiration date for the battery and provide an alert for battery replacement when the battery has expired. In addition, as previously described, the first identifying information received includes information on whether the battery is charged.

FIG. 13 shows a portable medical treatment and guidance apparatus 1000 for treating medical emergencies with a built-in tablet device 1002. Examples of such portable medical treatment and guidance apparatuses 1000 are the Mobilize Comprehensive Rescue System developed by ZOLL Medical Corporation of Chelmsford, Massachusetts. Each portable medical treatment and guidance apparatus 1000 includes a case 1004 (i.e., a housing) with a plurality of medical supplies 1006 (or medical items) for administering medical treatment (e.g., but not limited to, 4×SOF-T Wide tourniquet, 2×QuikClot bleeding control dressing, 2×6" flat emergency trauma dressing, 2×Hyfin chest seal, 2× Water-Jel universal burn dressing, 2× triangular bandage, 2×4.5" sterile conforming stretch gauze, 4×5"×9" sterile combine ABD pads, 2×10"×30" sterile multi-trauma dressing, a 36" SAM emergency splint, 2×4" elastic wrap bandage, a 4"×5" cold compress, an adhesive tape 2.5 yd, a CPR face shield with bite block, a 81 mg chewable aspirin (bottle), a 12 mg dissolvable allergy tablets (box), a 15 mg Insta-Glucose, 2× emergency space Mylar blanket, a portable charger and charging cord, a USB charging cube, an inspection card, 12× proof seals, 2× bag with biohazard markings, a pair of trauma shears, 10× nitrile gloves, a user manual and inventory card, 2 eye pads, 16× adhesive bandages (assorted sizes), 10× burn cream packets, 10× triple antibiotic ointment packets, 10× antiseptic wipes, a pair of tweezers, 10× hand sanitizer packets, an eye wash, and a first aid guide).

In some implementations, the portable medical treatment and guidance apparatus 1000 includes one or more RFID readers similar to, or the same as, the RFID readers 120 of the portable medical treatment and guidance apparatus 102 described with reference to FIG. 2B. Similarly, each of the medical items may include an RFID tag readable by the RFID readers of the portable medical treatment and guidance apparatus 1000.

A difference between the portable medical treatment and guidance apparatus 1000 and the portable medical treatment and guidance apparatus 700 is that the case 1004 is rigid and that the tablet device 1002 is built-into the case 1004 (i.e., it is not removable). The functionality described with reference to the portable medical treatment and guidance apparatus 700 is applicable to the portable medical treatment and guidance apparatus 1000. For brevity, this functionality will not be repeated.

FIG. 14 shows a portable medical treatment and guidance apparatus 1100 for treating medical emergencies with sensors for detecting when one or more medical items have been removed. The sensors are implemented into various compartments 1104 within the medical treatment and guidance apparatus's case 1102 (or housing). When a person removes a medical item from within a compartment 1104, the sensor transmits a signal to a processor of the case 1102, and that removal of the item is then reflected in the touchscreen display (e.g., of a tablet device 1106). One of more of the electronic components of the display may be built into the case 1102. This will be further described with reference to FIG. 15A.

In some implementations, the display is part of the tablet device 1106 and the processor of the case 1102 is implemented inside the tablet device 1106. In some implementations, the tablet device 1106 is removable in similarity to portable medical treatment and guidance apparatus 700.

The portable medical treatment and guidance apparatus 1100 is substantially similar to the portable medical treatment and guidance apparatuses 700, 1000, but includes sensors for detecting when one or more medical items have been removed.

FIG. 14 shows three medical items 1108, 1110, 1112 removed from respective compartments 1104 of the portable medical treatment and guidance apparatus 1100. In the implementation shown, medical items 1110 includes a tourniquet (A1), a dressing (B1), a chest seal (C1), and a pair of gloves. In the implementation shown, medical item 1108 is a removable cardiac/pulmonary resuscitative subsystem 1108 that may be used in combination (i.e., in communication via cable 1114) with a static cardiac/pulmonary resuscitative subsystem that is implemented within the case 1102 of the portable medical treatment and guidance apparatus 1100. A modular configuration of the cardiac/pulmonary subsystem allows for the larger removable cardiac/pulmonary resuscitative subsystem 1108 to be placed outside of the portable medical treatment and guidance apparatus 1100 in the immediate vicinity of the patient's side with key components of the cardiac/pulmonary resuscitative subsystem being optimally located immediately adjacent or in contact with the patient. For example defibrillation electrodes or shock delivery control or other AED controls are detached from the carrying case of the portable medical treatment and guidance apparatus and located immediately adjacent or in contact with the patient. This provides the rescuer unimpeded physical access to the patient while at the same time conveniently locating at their side only the components needed for the task at hand.

In the present implementation, the cable 1114 is configured to transmit high voltage signals for delivering electrotherapy to a patient. However, a wireless communication link between the removable cardiac/pulmonary resuscitative subsystem 1108 (or any electronic medical item) and the portable medical treatment and guidance apparatus 1100 may be used for transmitting data and status of the electronic medical device to the tablet device 1106 which can then communicate this data and status to the server 306 and database.

The cable 1114 additionally includes low voltage wires for transferring power, from an optional battery 1122 included within the case 1102 of the portable medical treatment and guidance apparatus 1100, and communication signals for the removable cardiac/pulmonary resuscitative subsystem 1108 to communicate with the tablet device 1106. The low voltage signals and power may take the form of a 4-wire USB or other serial communication interface. The removable cardiac/pulmonary resuscitative subsystem 1108 may include a processor and memory for communication and processing of attached sensor data (e.g., electrocardiogram (ECG) sensors), for performing self-evaluations (e.g., is the operation device operating properly), and for communicating with external devices (e.g., the tablet device 1106 and smartphones, such as the mobile device 104). For example, the removable cardiac/pulmonary resuscitative subsystem 1108 may include the electronics of computer device 1850 described with reference to FIG. 24.

In some implementations, the removable cardiac/pulmonary resuscitative subsystem 1108 includes one or both of a secondary display 1124 that can provide instructions to the caregiver or status lights 1126a, 1126b.

The compartment 1104 that stores the removable cardiac/pulmonary resuscitative subsystem 1108 includes at least one sensor for detecting when the removable cardiac/pulmonary resuscitative subsystem 1108 is removed from the compartment 1104.

In some implementations, the portable medical treatment and guidance apparatus 1100 includes one or more RFID readers similar to, or the same as, the RFID readers 120 of the portable medical treatment and guidance apparatus 102 described with reference to FIG. 2B. Similarly, each of the medical items may include an RFID tag readable by the RFID readers of the portable medical treatment and guidance apparatus 1100. In some examples, the at least one sensor may be an RFID reader that is configured to receive an RFID signal from the removable cardiac/pulmonary resuscitative subsystem 1108. For example, the removable cardiac/pulmonary resuscitative subsystem 1108 may include a RFID tag that includes a radio transponder, a radio receiver, and transmitter. When the RFID tag is triggered by an electromagnetic pulse from the RFID reader within the compartment 1104, the RFID tag transmits data back to the RFID reader. When data is received by the RFID reader, it transmits (e.g., wirelessly via a NFC protocol such as Bluetooth) a signal to the processor of the tablet device 1106 indicating that a medical item is present within the compartment 1104. If no data is received when an electromagnetic pulse is transmitted by the RFID reader, the RFID reader transmits a signal to the processor of the tablet device 1106 indicating that a medical item is not present within the compartment 1104. In some versions, the RFID tag may be self-battery-powered, or alternatively, be powered by the electromagnetic energy delivered to it by the RFID reader.

In some implementations, the RFID tag included in the medical item includes data that identifies the medical item as described with reference to FIG. 2B. For example, as shown in FIG. 2B, each medical item 124 may include an RFID tag 126 on the packaging of the medical item. For example, each of the following medical items may include an RFID tag on a packaging of the medical item or within the packaging of the medical item: a SOF-T Wide tourniquet, a QuikClot bleeding control dressing, a 6" flat emergency trauma dressing, a Hyfin chest seal, a Water-Jel universal burn dressing, a triangular bandage (or pack of bandages), a 4.5" sterile conforming stretch gauze (or pack of gauze), a 5"×9" sterile combine ABD pad (or pack of pads), a 10"×30" sterile multi-trauma dressing, a 36" SAM emergency splint, a 4" elastic wrap bandage, a 4"×5" cold compress, a roll of adhesive tape (e.g., 2.5 yd), a CPR face shield with bite block, a bottle of 81 mg chewable aspirin, a box of 12 mg dissolvable allergy tablets, a 15 mg Insta-Glucose, an emergency space Mylar blanket, a portable charger and charging cord, a USB charging cube, an inspection card, a pack of proof seals, a bag with biohazard markings, a pair of trauma shears, a pair of nitrile gloves, a user manual and inventory card, an eye pad, adhesive bandages (assorted sizes), a burn cream packet, 10× triple antibiotic ointment packets, antiseptic wipes, a pair of tweezers, hand sanitizer packets, an eye wash, and a first aid guide.

In other examples, the removable cardiac/pulmonary resuscitative subsystem 1108 may include an RFID tag that includes data specifying that the device is a removable cardiac/pulmonary resuscitative subsystem. This information can be used by the processor of the tablet device 1106 to determine what particular medical item is present and also missing at any given time. For example, knowledge that the removable cardiac/pulmonary resuscitative subsystem 1108 was removed can be used by the processor of the tablet device 1106 to tailor the medical instructions. In particular, it can infer that electrotherapy treatment is needed and immediately provide instructions regarding the use of administering electrotherapy treatment. This can save previous time during an emergency event.

In some implementations, the RFID tag includes information on expiration date of the medical item. The expiration date may then be transmitted from the tablet device 1106 to the server 306 and stored in the database. The expiration date can be for the medical item itself, such as medication having an expiration date after which the medication should be disposed of and not used, or can be for software installed on the medical item. Software expiring indicates a date after which the software should be upgraded or updated, not that the medical item itself needs to be disposed of and not used.

In some implementations, the RFID reader is capable of reading multiple RFID tags as described with reference to FIG. 2B. For example, one RFID reader within the portable medical treatment and guidance apparatus 1100 is capable or knowing which medical items are present within all compartments 1104 of the portable medical treatment and guidance apparatus 1100.

While described in the context of the portable medical treatment and guidance apparatus 1100, in some implementations, RFID readers and RFID tags are used with the portable medical treatment and guidance apparatuses 700, 1000. For example, some RFID tags can be read up to 1-2 meters away from a RFID reader.

Information on whether or not a medical device is located within a compartment 1104 may also be transmitted to the server 306 and stored in the database. For example, an output signal may be transmitted to the server 306 and database based on the detected removal of the at least one medical item. In this way, the transmitting to the server 306 may be automatic (i.e., as soon as the sensor indicates a change). This provides a status indication (e.g., which medical items are present, which are removed, which medical treatment is being performed, etc.) regarding the portable medical treatment and guidance apparatus 1100. This is helpful when the medical item may be detached or permanently removed from the portable medical treatment and guidance apparatus 1100 so the database can be updated to be representative of an inventory of the portable medical treatment and guidance apparatus 1100. For example, in some implementations, the status indication identifies an inventory of the plurality of medical supplies. In some implementations, the status indication identifies an expiration date of the plurality of medical supplies. This information may then be used by an inspector or manager of the portable medical treatment and guidance apparatus(es) to determine whether and when servicing may be needed.

In some implementations, the at least one sensor is a proximity sensor (a Hall Effect sensor or RF sensor) that is configured to receive a proximity signal from the at least one medical item. For example, a Hall Effect sensor integrated into the case transmits a signal indicative of the case 1102 opening due to a magnetic field moving away from or closer to the Hall Effect sensor. In another example, separate Hall Effect sensors may be located in the case at the bottom of individual compartments for each medical item. Magnets may be located at the bottom of the packaging for each medical item that, when placed in its appropriate compartment, cause the Hall Effect sensor for that particular compartment to trigger, indicating to the processor the presence of the medical item identified in advance with that particular compartment.

In some implementations, the at least one sensor is an optical sensor (e.g., a photodetector) that is configured to detect when an optical beam is broken indicating that a medical item has been removed from the compartment 1104. In some implementations, the at least one sensor is a pressure sensor for determining an amount of force (e.g., weight) that is applied to the pressure sensor.

In some implementations, the at least one sensor is part of a near-field communication link between the tablet device 1106 and an electronic medical item (i.e., a medical item that includes at least a processor and memory to facilitate a near-field communication link). For example, a preconfigured Bluetooth pairing can be setup when the portable medical treatment and guidance apparatus 1100 is first configured to be part of a network and communicate with the server 306 and database. An inspector performing such setup would press a button on the electronic medical item to pair with the tablet device 1106. Afterwards, data and information can be continuously communicated between the electronic medical item and the tablet device 1106 and also the server 306 and database.

The portable medical treatment and guidance apparatus 1100 may also detect the presence or absence of non-electronic medical items. For example, in some implementations, the medical item 1110 is a pair of medical gloves 1110. In this situation, an RFID tag within, attached to, or otherwise implemented with the medical gloves 1110 is detected by the RFID reader of the portable medical treatment and guidance apparatus 1100. In fact, any of the medical items described with reference to the portable medical treatment and guidance apparatuses 100, 700, 1000 may be detected using an RFID tag included in each respective medical item (the removable cardiac/pulmonary resuscitative subsystem 1108, a pair of scissors, a roll of gauze, a single dose pack of aspirin, etc.), or a package of medical items (e.g., a multi-pack of Band-Aids, a bottle of aspirin, etc.).

In some implementations, the medical item 1112 is ventilation equipment 1112 for providing manual ventilation to a patient. In the illustrated example, the removable ventilation equipment 1112 includes a face mask 1116 (e.g., bag-valve mask) and a ventilation bag 1118. The ventilation equipment can include status lights 1120*a*, 1120*b*, and/or may include other relevant user interactive display features for assisting the user in carrying out manual ventilation according to the provided instructions. Accordingly, the instructions may instruct the caregiver to take the removable ventilation equipment 1112 out from the case 1102, and attach the face mask 1116 to the patient using the straps, and to apply the ventilation bag 1118 to the face mask 1116, so that manual ventilations can be administered. In some implementations, the face mask and bag assembly includes an airflow sensor to measure inspiratory and/or expiratory flow so as to determine the effectiveness of the ventilations, for example, by assessing the tidal volume on each positive pressure breath administration and/or ventilation rate in breaths per minute. In some implementations, the ventilation equipment 1112 may include the electronics of computer device 1850 described with reference to FIG. 24.

When the medical item is an electronic medical item, the tablet device 1106 can communicate with the medical item and provide a level of control of the medical item. For example, if the tablet device 1106 is providing instructions for using the removable cardiac/pulmonary resuscitative subsystem 1108, the tablet device 1106 may communicate with the removable cardiac/pulmonary resuscitative subsystem 1108 (e.g., via the low voltage connection in cable 1114 or a wireless link such a Bluetooth) and adjust settings of the removable cardiac/pulmonary resuscitative subsystem 1108 according to the instructions. As a basic example, the tablet device 1106 can control the removable cardiac/pulmonary resuscitative subsystem 1108 to turn on.

By further monitoring when the removable cardiac/pulmonary resuscitative subsystem 1108 is removed from the compartment 1104 via the sensors within the compartment 1104, the instructions can be appropriately modified since it is assumed the caregiver has taken the removable cardiac/pulmonary resuscitative subsystem 1108 out of the compartment 1104 to begin administering medical treatment. In other words, the instructions are updated in real-time based on the detected removal of the medical item. In some implementations, the tablet device 1106 is configured to present via the user interface instructions for administering medical treatment based on the detected removal of the at least one medical item. In some case, the tablet device 1106 may prompt the user to confirm that the medical item(s) have been removed and to indicate whether the interactive query flow should proceed to the portion that corresponds to the removed medical item(s). The instructions for administering medical treatment involve one or more steps for using the at least one medical item.

In particular, the tablet device 1106 is configured to receive remote control information regarding remote control of an operation of the at least one medical item. For example, the tablet device 1106 can receive remote control instructions from the server 306 asking the tablet device 1106 to turn on the removable cardiac/pulmonary resuscitative subsystem 1108. As a further example, an emergency responder can transmit commands to the tablet device 1106 via the server 306 and a broader network. Such a feature could be implemented by an emergency responder "remote connecting" into the tablet device 1106 and the removable cardiac/pulmonary resuscitative subsystem 1108 for this remote control.

Aspects of this control can also be shared with the database. For example, not only can the tablet device 1106 communicate with the database to indicate that the removable cardiac/pulmonary resuscitative subsystem 1108 has been removed from the case 1102, but this information sent to the database can also indicate a status (e.g., is the device on, off, working properly, etc.) of the removable cardiac/pulmonary resuscitative subsystem 1108 itself.

In this way, data is communicable in both directions, from the removable devices (e.g., the removable cardiac/pulmonary resuscitative subsystem 1108) to the tablet device 1106 (and therefore the server 306 and database), and vice versa—from the server 306 and database to the removable device itself. For example, in some implementations, the tablet device 1106 is configured to receive instructions for administering medical treatment from the removable medical item. In the case of a removable cardiac/pulmonary resuscitative subsystem 1108, the instructions shown on the tablet device 1106 may be received from the removable cardiac/pulmonary resuscitative subsystem 1108 when they are stored in local memory of the removable cardiac/pulmonary resuscitative subsystem 1108 itself.

In some implementations, the status indication regarding the at least one medical item identifies a readiness status of whether the at least one medical item is ready to be used in an emergency. For example, if part or all of the medical item is missing (e.g., half a roll of gauze was used or the aspirin bottle is empty), the medical item may be characterized as not ready, needs inspection, or partially ready (e.g., some usable contents may be available whereas others might not). If on the other hand, the medical item is believed to be present and ready for use (e.g., aspirin bottle at least partially full) and does not have any missing parts, the medical item may be characterized as ready.

In some implementations, the status indication regarding the at least one medical item identifies a battery charge level of a battery of the at least one medical item. For example, in the situation where the medical item is an electronic device, such as the removable cardiac/pulmonary resuscitative subsystem 1108, the battery charge level represents the battery charge level of the battery of the removable cardiac/pulmonary resuscitative subsystem 1108.

In some implementations, the status indication regarding the at least one medical item identifies an expiration date of the at least one medical item.

In some implementations, the tablet device 1106 is configured to receive a self-diagnostic signal from the server 306 indicating that a self-diagnostic test of the at least one medical item is required. The self-diagnostic test may include powering on/off, checking communications to sensors and/or the tablet device 1106, and checking voltage levels.

In the situations where the medical item is electronic, the tablet device 1106 is configured to communicate the self-diagnostic signal to the medical item so a processor of the medical item can execute the self-diagnostic testing. The self-diagnostic test may include ensuring a battery level of the at least one medical item is above a threshold, ensuring an expiration date of the at least one medical item has not occurred, and ensuring the at least one medical item is present in the portable medical treatment and guidance apparatus. In some implementations, self-diagnostic testing tests all circuits, CPR capabilities, pacing, power, parameters, electrode expiration, and gel condition.

In some implementations, the tablet device 1106 is configured to determine when a self-diagnostic test of the at least one medical item is required. In these situations, the tablet device 1106 is configured to transmit a self-diagnostic signal indicating that a self-diagnostic test of the at least one medical item is required. The tablet device 1106 may also be configured to transmit a self-diagnostic signal to the at least one medical item to initiate a self-diagnostic test of the at least one medical item. The tablet device 1106 may also be configured to determine when a component of the at least one medical item is missing based on a result of a self-diagnostic test and the at least one sensor.

In some implementations, the portable medical treatment and guidance apparatus 1100 includes an indicator (e.g., visual indicator such as lights or a display, an audible indicator such as a speaker or buzzer, and/or a haptic indicator such as vibration generator) configured to alert a user that the at least one medical item has failed a self-diagnostic test and needs servicing. In these situations, the tablet device 1106 may be configured to present instructions to use a spare at least one medical item to replace a functionality of the at least one medical item that has failed a self-diagnostic test.

Furthermore, the tablet device 1106 may determine when a component of the at least one medical item has failed a self-diagnostic test based on a result of the self-diagnostic test. The tablet device 1106 may determine identifying information of the component of the at least one medical item that has failed the self-diagnostic test, present the determined identifying information of the component to the user interface, and/or present repair instructions for the component to the user interface. The repair instructions may include instructions to partially disassemble the at least one medical item.

In some implementations, the tablet device 1106 may determine when a component of the at least one medical item has passed a self-diagnostic test based on a result of the self-diagnostic test. The tablet device 1106 may notify a user when the at least one medical item has passed a self-diagnostic test and is ready for use.

FIG. 15A illustrates various components of the portable medical treatment and guidance apparatus 1100, and FIG. 15B shows which components are removable by a user versus components are static (i.e., not removable from the case 1102). The components include the medical supplies and equipment previously described as well as the physical sensors and computer hardware to perform the actions previously described. The portable case 1102 includes patient sensors 1218, electrotherapy components 1208, device sensors, the touchscreen display (e.g., of a tablet device 1106), a second display 1248, a speaker 1290, network connectivity 1260, power connections 1276, power circuitry 1271, a processor 1232, an externally swappable battery 1274, and an auxiliary battery 1272.

In some implementations, the medical instructions are broadcast from the portable medical treatment and guidance apparatus 1100 using the speaker 1290 integrated into the housing 1102.

The patient sensors 1218 can include a pulse oximeter 1211, blood pressure monitor 1213, capnography instrumentation 1215, an ECG 1217, and electrotherapy leads 1220a, 1220b.

The electrotherapy components 1208 can include a front end 1212, a pulse generator 1226, a capacitor 1228, and a control board 1224.

The device sensors can include image sensors, weight sensors, force sensors, photodetectors, optical sensors, electro-magnetic sensors, Hall effect sensors 1242, capacitive sensors, accelerometers 1240, a gyroscope, or pairs of distance (proximity) estimation sensors (e.g., radiofrequency sensors, Bluetooth based sensors or magnetic sensors). In some implementations, the device sensors include dedicated interrupters (e.g., photo-interrupters) that are located in the bottom of each compartment. Each stored item can be housed in a structure with an interrupter vane that blocks the light across the photo-interrupter when the item is inserted in the compartment. For example, determining whether a light sensor 1246 or an image sensor 1244 has transmitted a signal indicating that the light sensor 1246 or the image sensor 1244 light has sensed light (e.g., due to the case 1102 being opened in a lighted environment).

The portable medical treatment and guidance apparatus 1100 may also include one or more wireless radios 1260 that enable the portable medical treatment and guidance apparatus 1100 to wirelessly communicate with various different systems. Example wireless radios 1260 include a Wi-Fi radio 1262, a near-field communication radio 1264, a 4G and/or 5G radio 1266 for communication with a distributed network of cellular towers, and a Bluetooth radio 1268. Longer range radios (e.g., the Wi-Fi radio 1262 and the 4G/5G radios 1266) may be used by the apparatus 1100 to communicate with remote systems that allow administrators to monitor inventory or status of the portable medical treatment and guidance apparatus 1100, and/or allow the portable medical treatment and guidance apparatus 1000 to communicate with a remote system to indicate that the portable medical treatment and guidance apparatus is being used in an emergency.

For example, the portable medical treatment and guidance apparatus 1100 may be configured to call 911 or other appropriate emergency services and indicate that an emergency is happening at a specific location identified by a GPS system of the portable medical treatment and guidance apparatus 1100. Shorter range radios, such as Bluetooth radio 1268, may be used by the processor 1232 to wirelessly communicate with other components of the portable medical treatment and guidance apparatus 1100 that may not be physically connected to the case 1102 (e.g., a wireless pulse oximeter 1211).

In some implementations, the wireless radios 1260 are configured to transmit the status indication regarding the portable medical treatment and guidance apparatus 1100 to a nearby mobile device (e.g., an inspector's smart phone).

The near-field communication radio 1264 can be used by the portable medical treatment and guidance apparatus 1100 to identify that the case 1210 has been placed near a particular location (e.g., a docking station or another portable medical treatment and guidance apparatus). In various embodiments, the interactive query flow may continuously provide throughout each inquiry page an input for the medical treatment and guidance apparatus 1100 to call emergency services, so that when the caregiver actuates the input to call emergency services, the connection may then be made. Or, in some embodiments, the medical treatment and guidance apparatus 1100 may automatically call emergency services, if not done so already, based upon caregiver answers to the interactive query flow. For example, if the caregiver inputs to the apparatus that the victim is unconscious and without a pulse, then the medical treatment and guidance apparatus may automatically prompt the victim to input whether emergency services has been called, along with proceeding immediately to the resuscitation portion of the query flow. If answered in the negative that emergency services have not been called, then the medical treatment and guidance apparatus 1100 may automatically do so or at least instruct the caregiver to do so, in a manner that does not detract from providing resuscitative treatment to the victim.

The portable nature of the medical treatment and guidance apparatus 1100 is facilitated by one or more batteries that are able to power the electronics of the portable medical treatment and guidance apparatus 1100, for example, an auxiliary battery 1272 and an externally-swappable battery 1280. The batteries 1272, 1280 may lose charge over time, either due to parasitic drain or due to use for occasional operations, such as wireless communications with the server 306 and database that monitors the inventory of the apparatus 1100. The portable medical treatment and guidance apparatus 1100 includes various different components to resupply power to the batteries 1272, 1280. In some examples, one or more of the batteries 1272, 1280 may be charged by an external supply of power. For example, the portable medical treatment and guidance apparatus 1100 may be stored in a cabinet or docking system that is connected to an external supply of power, and that cabinet or docking system may electrically communicate with the portable medical treatment and guidance apparatus 1100 to provide power through an input power terminal 1282, input power contact pads 1284 (e.g., pads that are contacted by pogo pins of the cabinet or docking system), or through a wireless power receiver 1281. The portable medical treatment and guidance apparatus 1100 may include power circuitry 1271 that controls charging of the auxiliary battery 1272 and/or the externally swappable battery 1280, and the distribution of power along the electrical busses 1236 of the portable medical treatment and guidance apparatus 1100.

FIG. 16 is a flowchart of a computer-implemented method 1300 for monitoring when a removable device is removed from the portable medical treatment and guidance apparatus and performing actions as a consequence of the removal. While described primarily with reference to the portable medical treatment and guidance apparatus 1100, the portable medical treatment and guidance apparatus can be any of the portable medical treatment and guidance apparatuses 100, 700, 1000, 1100 previously described.

The method is performed by a processor of the tablet device, a mobile device, and/or the server 306. At least one sensor within the portable medical treatment and guidance apparatus 1100 is in communication this this processor. The processor monitors 1302 the at least one sensor within the portable medical treatment and guidance apparatus for the presence of a medical item. When a user removes 1304 the medical item, the at least one sensor transmits a signal to the processor indicating the removal where the processor detects the removal 1306 of the medical item.

In some implementations, medical item information is encoded into the signal (e.g., identifying information of the medical item is encoded into the RFID tag as previously described) and transmitted to the processor with the signal from the at least one sensor. This information is used by the processor to identify 1308 which medical item was removed.

Identifying information of the medical item is used by the processor to query 1310 an operations database to determine which instructions to show on a display of the case 1102 and announce on a speaker 1290 of the case 1102. For example, knowing that the removed device is the removable cardiac/pulmonary resuscitative subsystem 1108, the instructions may begin with instructions on the use of the removable cardiac/pulmonary resuscitative subsystem 1108 directly, or may alternatively provide a notification for the user to confirm that the interactive query flow should jump to the portion that corresponds to usage of the removable cardiac/pulmonary resuscitative subsystem 1108. The operations database may be implemented at the server 306 level.

As part of proving the instructions to the user, the processor displays 1312 instructions on the display (e.g., the display of the tablet device, mobile device, or built-in display). The processor announces 1314 instructions using the speaker 1290. The processor receives 1316 feedback from the medical item and/or from the user via the user interface during use. For example, the feedback may be from the medical item directly (e.g., patient vital signs) or from the user (e.g., confirm Aspirin was administered). The processor advances 1318 through the queried flow-chart of instructions and repeats this process for each individual instruction.

The processor is also configured to communicate with the server 306 either simultaneously with or sequentially to providing medical instructions to a user. The processor transmits 1320 information of the identity of the medical item to a server 306. For example, the information may represent the serial number or type of medical item removed from the portable medical treatment and guidance apparatus 1100. The processor may update 1322 the database with the medical part information (e.g., inventory, usage). The processor may also alert 1324 personnel of database changes, part information changes, and/or that the medical item is being used. For example, a push notification to a smartphone of an inspector could indicate that removable cardiac/pulmonary resuscitative subsystem 1108 was removed from the portable medical treatment and guidance apparatus 1100.

In response to receiving the case report, the server 306 is configured to provide a notification that the medical treatment has been initiated, update the database, using the first identifying information associated with the housing of the medical treatment and guidance apparatus system, to indicate that the medical treatment and guidance apparatus system has been used, and update the database, using the second identifying information associated with the housing of the medical treatment and guidance apparatus system, to indicate that the at least one medical item has been used.

In some implementations, the server 306 is configured to perform a query of the database for respective portable medical treatment and guidance apparatus associated with past due inspections and in responsive to the querying, presenting a notification that the respective medical treatment and guidance apparatus systems are associated with the past due inspections. In some implementations, the mobile device 104 is configured to instruct the server 306 to perform a query of the database for respective medical treatment and guidance apparatus systems associated with past due inspections; and responsive to the querying, presenting a notification that the respective medical treatment and guidance apparatus systems are associated with the past due inspections.

In some implementations, the server 306 is configured to receive status updates regarding the plurality of portable medical treatment and guidance apparatuses, update the status information in the database based on the received status updates, and control the user interface to present the status indication of the plurality of portable medical treatment and guidance apparatuses based on the updated status information.

In some implementations, the received status updates identify a presence of at least one medical item housed within at least one of the plurality of portable medical treatment and guidance apparatuses. In some implementations, the received status updates identify battery levels for at least one medical item housed within at least one of the plurality of portable medical treatment and guidance apparatuses. In some implementations, the received status updates identify a readiness of at least one medical item housed within at least one of the plurality of portable medical treatment and guidance apparatuses.

In some implementations, the server 306 is configured to determine an inventory of at least one medical item housed within at least one of the plurality of portable medical treatment and guidance apparatuses. In some implementations, the server 306 is configured to determine whether the inventory of the at least one medical item is below a threshold. For example, the server 306 may compare the inventory of the at least one medical item with a predetermined expected inventory level for that medical item. In this scenario, the database can maintain expected inventory levels (e.g., defined during initial setup, or user controlled). If the inventory level is below the threshold, the server 306 can initiate a purchase of more medical items or alert an inspector to check on the status of the portable medical guidance and treatment apparatus.

In some implementations, the server 306 is configured to present via the user interface whether the inventory of the at least one medical item is below a threshold.

In some implementations, the server 306 is configured to initiate a replenishment of the at least one medical item associated with the medical treatment and guidance apparatus system. For example, the server 306 may transmit a request to a supplier so that the supplier ships replacement medical items to a location of the medical treatment and guidance apparatus system (e.g., if there are multiple buildings, the medical items can be shipped directly to the building that needs the medical item), or may alternatively generate a record for a manager and/or supplier to note that the medical item may need to be replenished. In some examples, the request to replenish the medical item is initiated when the inventory of the medical item is below a threshold. In this way, the server 306 is configured to initiate a request to acquire more of at least one medical item. In some implementations, the server 306 is configured to prioritize a purchase of at least one medical item over another at least one medical item (e.g., based on a predicted need using historical inventory levels represented in database).

In some implementations, the server 306 is configured to determine the closest nearby portable medical treatment and guidance apparatuses to a respective portable medical treatment and guidance apparatus.

In some implementations, the server 306 is configured to remote control at least one of the plurality of portable medical treatment and guidance apparatuses. For example, in some cases, remote control is achieved by controlling, from the server 306, or via an external device, the tablet device within the portable medical treatment and guidance apparatus. Remote control can be achieved using a remote desktop application. In this scenario, remote control from the server 306 or external device enables a remote user to control of the tablet device as if the user was in front of the tablet. In some implementations, the server 306 is configured to remote control at least one medical item (e.g., an AED) within a respective portable medical treatment and guidance apparatus of the plurality of portable medical treatment and guidance apparatuses.

Remote control is advantageous in a few scenarios. One scenario is where an untrained caregiver needs assistance in navigating the application running on the tablet during an emergency event. This could happen if the caregiver does not understand the query/instructions or if the caregiver is too preoccupied on the patient. Responders could remote connect into the system to assist the caregiver in this scenario. A second scenario is where an inspector would like to confirm the tablet device is functioning without having to travel to the portable medical treatment and guidance apparatus and manually confirm. In this scenario, the inspector could simulate an emergency event on the tablet device from a remote site to ensure proper functionality.

In some implementations, the server 306 is configured to notify mobile devices within a proximal location of a respective portable medical treatment and guidance apparatus of the plurality of portable medical treatment and guidance apparatuses when the respective portable medical treatment and guidance apparatus is turned on. In some implementations, the server 306 is configured to notify mobile devices within a proximal location of a respective portable medical treatment and guidance apparatuses of the plurality of portable medical treatment and guidance apparatuses when at least one medical item is removed from the respective portable medical treatment and guidance apparatuses.

In some implementations, the server 306 is configured to transmit a request for a status update of each portable medical treatment and guidance apparatus of the plurality of portable medical treatment and guidance apparatuses. In some implementations, the status update includes battery levels for each battery operable medical item within the respective portable medical treatment and guidance apparatus. In some implementations, the status update includes an expiration date of each expireable medical item within the respective portable medical treatment and guidance apparatus.

Upon receiving the status update, the server 306 can compare the battery levels to a threshold to ensure the batteries are sufficiently charged. The server 306 can also compare the current date to the received expiration date of each expireable medical item. In some examples, the battery status and expiration information is updated in the database.

In some implementations, the server 306 is configured to transmit a request for a self-diagnostic test to be performed by each portable medical treatment and guidance apparatuses of the plurality of portable medical treatment and guidance apparatuses that supports a self-diagnostic capability (e.g., defibrillators, etc.). In some implementations, the self-diagnostic test includes ensuring that a defibrillator charge and discharge capability is functioning properly. Proper functionality is determined when one or more of the following conditions are satisfied. In some examples, the defibrillator verifies that the defibrillation electrodes are properly preconnected to the device. In some examples, the defibrillator verifies that the ECG signal acquisition and processing electronics are functional. In some examples, the defibrillator verifies that the device's defibrillator electronics are functional and can charge and discharge at up to 200 joules. In some examples, the defibrillator verifies proper function of the Fully Automatic AED Plus microprocessor electronics and the integrity of its software. In some examples, the defibrillator verifies that CPR monitoring and compression depth detection are functional. In some examples, the defibrillator verifies that voice prompts are functional.

The received status updates include information related to a self-diagnostic test for at least one medical item housed within at least one of a plurality of portable medical treatment and guidance apparatuses. The updated status information includes updating whether a respective portable medical treatment and guidance apparatus has passed a self-diagnostic test.

In some implementations, the server 306 is configured to indicate which portable medical treatment and guidance apparatuses of the plurality of portable medical treatment and guidance apparatuses have passed a self-diagnostic test representing that the respective portable medical treatment and guidance apparatus is ready for use. In some implementations, the server 306 is configured to indicate which portable medical treatment and guidance apparatuses of the plurality of portable medical treatment and guidance apparatuses require attention. In some implementations, the server 306 is configured to indicate a location of each portable medical treatment and guidance apparatuses of the plurality of portable medical treatment and guidance apparatuses that require attention. In some implementations, the server 306 is configured to indicate a date that each portable medical treatment and guidance apparatuses of the plurality of portable medical treatment and guidance apparatuses last passed a self-diagnostic test. In some implementations, the server 306 is configured to indicate a date that each portable medical treatment and guidance apparatuses of the plurality of portable medical treatment and guidance apparatuses was last opened. In some implementations, the server 306 is configured to indicate a date that each portable medical treatment and guidance apparatuses of the plurality of portable medical treatment and guidance apparatuses was last used.

As discussed herein, a caregiver may remove one or more medical items from a portable medical treatment and guidance apparatus during the course of the apparatus's use. Some caregivers will be familiar with the medical treatment and guidance apparatus and/or with the medical items contained therein and thus be able to quickly locate and remove a desired medical item from the medical treatment and guidance apparatus. However, in a high stress emergency situation even caregivers familiar with the medical treatment and guidance apparatus and/or with the medical items contained therein may have difficulty quickly locating and removing a desired medical item from the medical treatment and guidance apparatus, thereby delaying use of the medical item and accordant medical treatment of the victim/patient. Additionally, some caregivers will not be familiar with the medical treatment and guidance apparatus and/or with the medical items contained therein and thus may have difficulty quickly locating and removing a desired medical item from the medical treatment and guidance apparatus, thereby delaying use of the medical item and accordant medical treatment of the victim/patient.

As also discussed herein, a mobile device, a tablet device, etc. can electronically provide instructions, e.g., via an application, to a caregiver for administering medical treatment using the medical treatment and guidance apparatus, and the instructions can include guiding the caregiver to retrieve a medical item from the medical treatment and guidance apparatus. In some implementations, each of the medical items in the medical treatment and guidance apparatus includes a tag (active or passive), which may facilitate quick location and removal of a desired medical item from the medical treatment and guidance apparatus. For example, as discussed above, each medical item within the medical treatment and guidance apparatus may include an RFID tag on the packaging of the medical item. Another example of a tag that may be included on a medical item's packaging is an NFC tag. In some instances, the tag may not be included on the medical item's packaging but otherwise be included with the medical item within the medical treatment and guidance apparatus, such as by being attached to a metallic or plastic housing of the medical item. By including a tag, any medical item within the medical treatment and guidance apparatus can have smart functionality to facilitate quick location and removal of the medical item from the apparatus even if the medical item is "dumb" and does not have any electronic or communication functionality, such as gauze, bandages, a tourniquet, etc.

As discussed herein, medical items within the medical treatment and guidance apparatus can each include a tag (e.g., an RFID tag or other tag) readable by a reader (e.g., an RFID reader or other reader) to indicate that a medical item is present within a particular compartment (e.g., pocket, drawer, partition, etc.) of the medical treatment and guidance apparatus. Each of the compartments can include at least one light emitting diode (LED) or other light configured to be visible, when illuminated, from outside the medical treatment and guidance apparatus.

In some implementations, when an instruction is provided to a caregiver guiding the caregiver to retrieve a medical item from the medical treatment and guidance apparatus, the at least one light for the compartment in which the medical item is located can illuminate. The illumination provides a visual indication to the caregiver where the medical item is located within the medical treatment and guidance apparatus, thereby helping the caregiver quickly retrieve the medical item.

One or more medical items in the medical treatment and guidance apparatus may be reusable. Reusable medical items, such as glucose meters, lactate meters, point-of-care ultrasound probes, and pulse oximeters, tend to be expensive items that would be costly and burdensome to replace if left at the scene of an emergency. Instructing a caregiver to return a reusable medical item to the medical treatment and guidance apparatus and where to return the reusable medical item within the medical treatment and guidance apparatus may help reduce costs. Existing techniques to avoid loss of reusable medical items after removed from a medical treatment and guidance apparatus include physically tying or tethering reusable medical items to the medical treatment and guidance apparatus with a cable, which can get tangled and/or interfere with the caregiver's movements and/or with other medical items. Another existing technique is using a manual checklist to account that every reusable medical item has been returned to or is present in the medical treatment and guidance apparatus, which can be time consuming and can require returning to a scene to retrieve an unreturned medical item if the checklist is not completed on scene. An emergency situation may require that the checklist not be completed on scene, e.g., so the patient can be transported more quickly to a hospital. In some implementations, when an instruction is provided to a caregiver guiding the caregiver to return a medical item to the medical treatment and guidance apparatus, e.g., because the medical item is a reusable item that is no longer needed for use with the patient/victim, the at least one light for the compartment in which the medical item should be stowed can illuminate. The illumination provides a visual reminder to the caregiver that the medical item needs to be returned to the medical treatment and guidance apparatus and a visual indication to the caregiver where the medical item should be placed within the medical treatment and guidance apparatus, thereby helping to ensure that the medical item is returned to the medical treatment and guidance apparatus, helping the caregiver quickly return the medical item to a correct location within the medical treatment and guidance apparatus, and helping to ensure that the medical item is consistently at a same location within the medical treatment and guidance apparatus so repeated users of the medical treatment and guidance apparatus can predictably know where the medical item is located within the medical treatment and guidance apparatus.

In some implementations, the lights of the medical treatment and guidance apparatus can be color coded to the medical items. As discussed herein, each medical item can be associated with color information, such as by that color being on a label attached to the medical item along with the medical item's associated group/label. Table 1 above shows some examples of colors associated with certain medical items. The color of the light that illuminates for a particular medical item to be retrieved or returned can correspond to the medical item's color information, which may help the caregiver quickly locate that medical item within or return that medical item to the compartment of medical treatment and guidance apparatus. Different medical items in the same compartment may all have the same color information such that only one color of light is needed for that compartment. Different medical items in the same compartment may not all have the same color information such that more than one color of light is needed for that compartment.

In some implementations, the lights of the medical treatment and guidance apparatus can be color coded to status of the medical items. A light for a compartment associated with a medical item to be retrieved can illuminate in a first color to indicate that the medical item should be retrieved from the compartment, and the light can illuminate in a second, different color in response to the medical item's removal from the compartment to indicate that the medical item has been removed and should be returned to the compartment.

In some implementations, the lights of the medical treatment and guidance apparatus can indicate a number of medical items. A number of lights that illuminate for a compartment associated with a medical item to be retrieved can correspond to a total number of that item within the compartment. Then, in response to one or more of the medical item being retrieved from the medical treatment and guidance and apparatus, a corresponding number of the lights can be turned off or can be changed to a different color of illumination. For example, five lights can illuminate to indicate that five tourniquets are located in the compartment, and in response to one of the tourniquets being removed from the compartment, one of the lights can be turned off (or changed to a different color) with four lights remaining illuminated.

In some implementations, an audible sound can be provided, e.g., via a mobile device, a tablet device, etc., in conjunction with light illumination to help ensure that the caregiver takes notice of illuminated light(s).

In some implementations, when a caregiver retrieves a reusable medical item from the medical treatment and guidance apparatus, a current geographic location, such as GPS, can be stored using a geographic sensor on board the medical treatment and guidance apparatus (e.g., on a tablet device thereof) or included with the device (e.g., a mobile device) otherwise providing instructions to the caregiver. The medical item's retrieval and the geographic location can thus be correlated, e.g., by date/time stamp, to indicate a geographic location where the reusable medical item was removed from the medical treatment and guidance apparatus. In this way, if the reusable medical item is not returned to the medical treatment and guidance apparatus on scene, the medical item's likely geographic location can be determined to facilitate its retrieval and return to the medical treatment and guidance apparatus. In an emergency situation there may not be time to return the reusable medical item to the medical treatment and guidance apparatus before transporting the patient to a hospital, or the stress of the emergency situation may lead to the reusable medical item accidentally not being returned to the medical treatment and guidance apparatus.

In some implementations, when a caregiver retrieves a reusable medical item from the medical treatment and guidance apparatus, a distance of the reusable medical item from the medical treatment and guidance apparatus can be determined. The distance may be useful in providing a more precise instruction is provided to a caregiver guiding the caregiver to return the medical item to the medical treatment and guidance apparatus by indicating the medical item's current distance from the medical treatment and guidance apparatus. The distance can be determined in a variety of ways, such as by using wireless signal strength between the medical item and the medical treatment and guidance apparatus (e.g., a tablet device thereof) or a device (e.g., a mobile device) being used in conjunction with the medical treatment and guidance apparatus. Some reusable medical items, such as at least some pulse oximeters, have a built-in capability for wireless communication, thereby allowing the medical item and the medical treatment and guidance apparatus (e.g., a tablet device thereof) or the device (e.g., a mobile device) to detect signal strength. The stronger the signal, the closer the medical item.

In some instances, a reusable medical item should be sanitized or sterilized before being returned to the medical treatment and guidance apparatus for subsequent use. In such instances, an instruction to return a reusable medical item to the medical treatment and guidance apparatus and where to return the reusable medical item within the medical treatment and guidance apparatus can also include a warning to the caregiver that the reusable medical item should be sanitized or sterilized before being returned to the medical treatment and guidance apparatus.

In some instances, a reusable medical item may have a limited number of uses before the reusable medical item should be calibrated before subsequent use or before the reusable medical item should be disposed of and not reused. In such instances, an app (online or on a tablet device or mobile device) can be configured to track a number of uses of the reusable medical item by using a counter to count a number of times that the reusable medical item is removed from the medical treatment and guidance apparatus. If the count is less than a predetermined maximum number of permitted uses, an instruction is provided to a caregiver guiding the caregiver to return the medical item to the medical treatment and guidance apparatus. If the count is greater than the predetermined maximum number of permitted uses, an instruction is provided to a caregiver warning the caregiver that the medical item must be calibrated before being returned to the medical treatment and guidance apparatus or that the medical item should be disposed of and not reused or returned to the medical treatment and guidance apparatus.

In some instances, a reusable medical item may not be returned to the medical treatment and guidance apparatus, such as if the medical item is lost or is broken or otherwise becomes unusable. An instruction may still be provided to a caregiver guiding the caregiver to return the reusable medical item to the medical treatment and guidance apparatus, but instead of returning the exact medical item removed from the bag, a replacement, functional medical item may instead be put in the medical treatment and guidance apparatus.

FIG. 17 shows another implementation of a portable medical treatment and guidance apparatus 2100 including a plurality of compartments (bag pockets, as shown) 2102 each including at least one medical item therein (only one medical item 2104 is shown in FIG. 17) and each having a light 2106 associated therewith. In this implementation, the portable medical treatment and guidance apparatus 2100 is a defibrillator/monitor device, but it can be appreciated that other such portable medical treatment and guidance apparatuses may be used, for example, interactive trauma kits described herein, ventilators, or other such devices. The medical item 2104 can include one or more items that typically come along with a portable medical treatment and guidance apparatus, such as a glucose meter, lactate meter, ultrasound probe, camera and/or imaging device, capnography sensor, airflow sensor, ventilation bag or device, pulse oximeter, mobile device, or other appropriate item. The lights 2106 are LED strips in the example of FIG. 17 but can have other configurations in other implementations. The portable medical treatment and guidance apparatus 2100 houses a tablet device 2108, which can be removable from the portable medical treatment and guidance apparatus 2100 similar to that discussed above regarding the portable medical treatment and guidance apparatuses 700, 1100. Each of the compartments 2102 includes a reader configured to read a tag of each of the medical items contained in that compartment 2012. Only one reader 2110 is shown in FIG. 17, for the compartment 2102 in which the medical item 2104 including a tag 2112 on its packaging is located. The reader and the tablet device 2108 are configured to communicate, as discussed herein. The tablet device 2108 is also configured to cause illumination of the lights 2106, as discussed further below. Instead of the tablet device 2108, a mobile device can similarly be used as discussed herein.

As shown in FIG. 17, when a caregiver receives an instruction, e.g., via the tablet device 2108, to retrieve the medical item 2104 from the portable medical treatment and guidance apparatus 2100, the light 2106 for the compartment 2102 in which the medical item 2104 is located illuminates, e.g., in response to a signal from the tablet device 2108. The illuminated light 2106 in FIG. 17 is green but can be another color. When the tablet device 2108 provides an instruction to retrieve a medical item 2104 from the portable medical treatment and guidance apparatus 2100, the tablet device 2108 can be configured to in conjunction therewith cause the light 2106 for the compartment 2102 in which the medical item 2104 is located illuminates. In other words, the providing of the instruction can trigger the tablet device 2108 to cause the appropriate light 2106 to illuminate. The proper one of the lights 2106 can be identified by the tablet device 2108, for example, by consulting a stored lookup table correlating each of the medical items 2104 with one of the lights 2106.

Similarly, in an instance in which the medical item 2104 is a reusable item, when a caregiver receives an instruction, e.g., via the tablet device 2108, to return the medical item 2104 to the portable medical treatment and guidance apparatus 2100, the light 2106 for the compartment 2102 in which the medical item 2104 should be placed illuminates, e.g., in response to a signal from the tablet device 2108. When the tablet device 2108 provides an instruction to return a medical item 2104 to the portable medical treatment and guidance apparatus 2100, the tablet device 2108 can be configured to in conjunction therewith cause the light 2106 for the compartment 2102 to which the medical item 2104 should be returned illuminates. In other words, the providing of the instruction can trigger the tablet device 2108 to cause the appropriate light 2106 to illuminate.

The tablet device 2108 can be configured to cause the appropriate light 2106 to illuminate in any of a variety of ways, whether the light 2106 is being illuminated for retrieval or returning purposes. For example, the lights 2106 can each be operatively coupled to a switch that is operatively coupled to the tablet device 2108. The tablet device 2108 can be configured to cause the appropriate one of the switches to close to cause light 2106 illumination and to cause the appropriate one of the switches to open to stop light 2106 illumination.

In some implementations, the tablet device 2108 can be configured to not provide a text and/or graphical instruction to retrieve a medical item 2104 and instead cause light 2106 illumination to indicate to a caregiver to retrieve a medical item 2104 from the compartment 2102 associated with the illuminated light 2106. In such implementations, the text and/or graphical instruction may be provided by another device, such as a mobile device. The other device, e.g., mobile device, can be configured to transmit an instruction to the tablet device 2108 to cause the appropriate one of the lights 2106 to illuminate. An app running on the other device can be configured to determine the appropriate one of the lights 2106 to instruct the tablet device 2108 to illuminate, such as by using a lookup table similar to that discussed above.

FIG. 18 shows a medical treatment and guidance apparatus management system 1400 where the portable medical treatment and guidance apparatuses 100, 700, 1000, 1100, 2100 communicate with a server 306 and database for inventory management. Notably, the server 306 and database is compatible with any or all of the portable medical treatment and guidance apparatuses 100, 700, 1000, 1100, 1200. Computational devices (e.g., the mobile devices 104 or 308a, a laptop computer 308b, etc.) may be used to manage the database of inventory information. For example, the laptop computer 308b may be in communication with the server 306 via the Internet, and database information associated with the server 306 can be queried and/or updated by the laptop 308b.

In addition, electronic devices 1402, 1404, 1406 (e.g., the "other devices" 40 as described with reference to FIG. 1), may also be included in the medical treatment and guidance apparatus management system 1400 such that the inventory, status, and/or readiness of the electronic devices 1402, 1404, 1406 may be included in the database. For example, a hospital can manage inventory of all electronic medical items and all portable medical treatment and guidance apparatuses. In this example, when a user removes one of the portable medical treatment and guidance apparatuses from a wall of the hospital (e.g., using GPS data, or other sensors), a notification is sent to the server 306 that the portable medical treatment and guidance apparatus has been moved being used. Furthermore, as a user opens a case of the portable medical treatment and guidance apparatuses and removes a medical item, a processor associated with the portable medical treatment and guidance apparatus communicates this information over the medical treatment and guidance apparatus management system 1400 to the server 306 and to the associated computers 308b, tablet devices, and mobile devices 104, 308a.

In this way, a medical treatment and guidance apparatus management system includes a plurality of portable medical treatment and guidance apparatuses, each portable medical treatment and guidance apparatus including a treatment and guidance user interface configured to provide an interactive query flow for assisting a user in providing medical treatment, a plurality of medical supplies for the user to provide the medical treatment, and communications circuitry configured to provide status information of the portable medical treatment and guidance apparatus to at least one medical treatment and guidance apparatus management device wherein the status information includes at least inventory data for the portable medical treatment and guidance apparatus; the at least one medical treatment and guidance apparatus management device having a management user interface for providing a status indication of the plurality of portable medical treatment and guidance apparatuses, the at least one medical treatment and guidance apparatus management device configured to: receive status updates regarding the plurality of portable medical treatment and guidance apparatuses, and update, on the management user interface, the status indication of the plurality of portable medical treatment and guidance apparatuses based on the received status updates.

In some implementations, the status indication of the plurality of portable medical treatment and guidance apparatuses includes readiness information of each respective portable medical treatment and guidance apparatus representing whether each respective portable medical treatment and guidance apparatus is ready to be used. In some implementations, the status indication of the plurality of portable medical treatment and guidance apparatuses includes battery information of each respective portable medical treatment and guidance apparatus representing whether each respective portable medical treatment and guidance apparatus is sufficiently charged.

In some implementations, the status indication of the plurality of portable medical treatment and guidance apparatuses comprises self-diagnostic information of each respective portable medical treatment and guidance apparatus representing whether each respective portable medical treatment and guidance apparatus has passed a self-diagnostic test. In some implementations, the self-diagnostic test includes ensuring battery levels for each battery operable medical item within the respective portable medical treatment and guidance apparatus is above a threshold, ensuring an expiration date of each expireable medical item within the respective portable medical treatment and guidance apparatus has not occurred, and ensuring each removable medical item is present within the respective portable medical treatment and guidance apparatus.

In some implementations, the at least one medical treatment and guidance apparatus management device is further configured to transmit a request for a self-diagnostic test to be performed by at least one of a plurality of portable medical treatment and guidance apparatuses. In some implementations, the at least one medical treatment and guidance apparatus management device is further configured to transmit a request for a self-diagnostic test to be performed by at least one medical item housed within at least one of the plurality of portable medical treatment and guidance apparatuses.

In some implementations, the self-diagnostic test includes ensuring a battery level of the at least one medical item is above a threshold, ensuring an expiration date of the at least one medical item has not occurred, and ensuring the at least one medical item is present in the respective portable medical treatment and guidance apparatus.

In some implementations, the at least one medical treatment and guidance apparatus management device is further configured to present via the management user interface whether the inventory data for the portable medical treatment and guidance apparatus is below a threshold.

FIGS. 19A-19D show screenshots 1500, 1550, 1560, 1570 of information displayed on a mobile device (e.g., mobile device 104) when querying the database for inventory management status of one of more portable medical treatment and guidance apparatuses. For example, the mobile device can run a mobile software application to provide real-time database queries to help inspectors manage one of more portable medical treatment and guidance apparatuses and other electronic devices. The app shown in FIGS. 19A-19D can be similar to, or the same as, the app shown being used by an inspector 302 in FIG. 6 and/or FIG. 12. In other words, the app described in FIGS. 19A-19D is capable of imaging portable medical treatment and guidance apparatuses to assess inventory (e.g., via imaging processing) and communicate the inventory information to a database. In general, the application also queries the database and presents inventory status, readiness status, and self-diagnostic status to the user or inspector (e.g., the inspector 302 of FIG. 6 and/or FIG. 12). For example, once the user selects a particular portable medical treatment and guidance apparatus in the database, the mobile device is configured to show one or more indicators 1502 representing whether the portable medical treatment and guidance apparatus is ready to be used (e.g., inventory is full and that no medical items are missing).

Figure 19A:
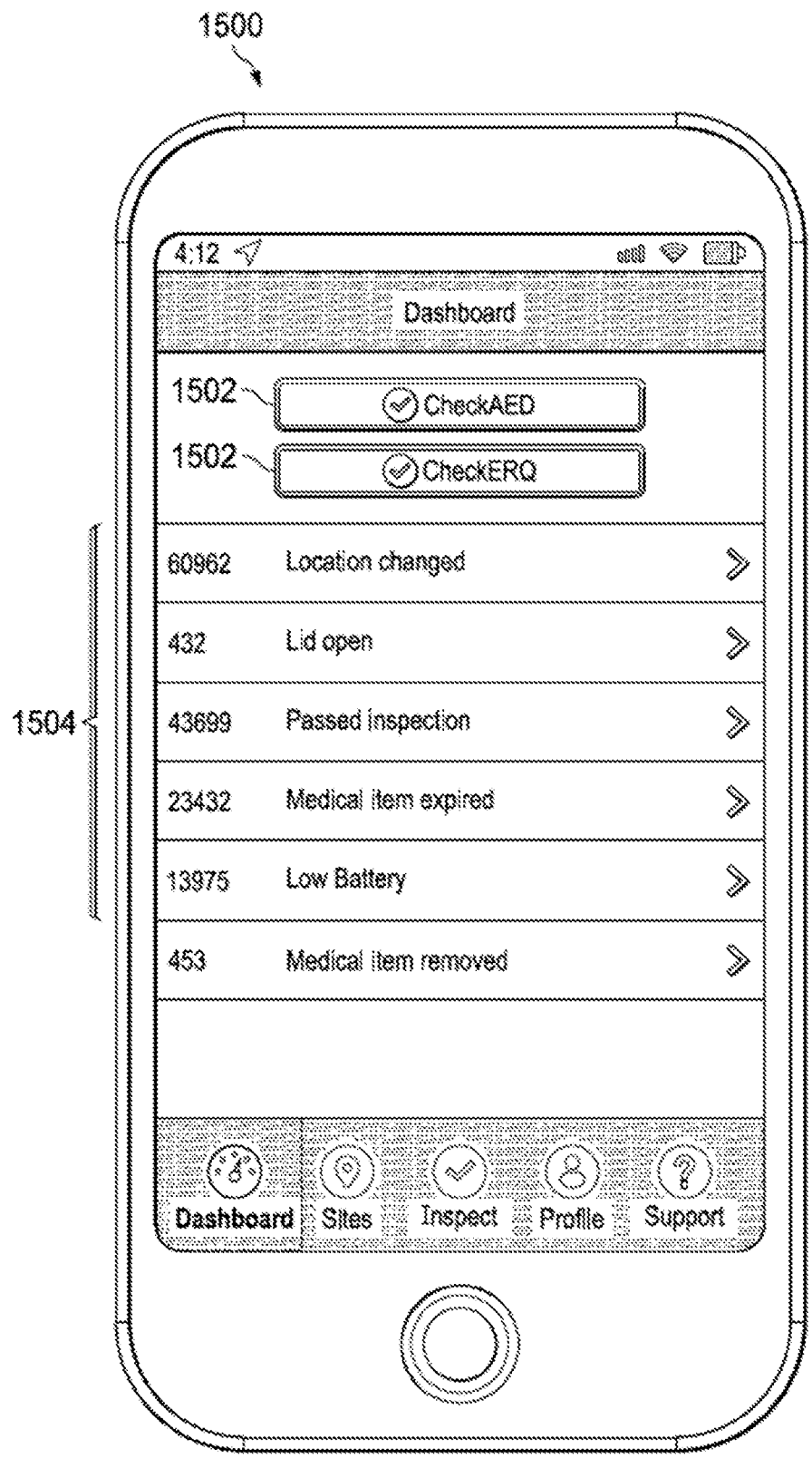

FIG. 19A shows a chronological list of events 1504 that have been stored in the database. This list of events 1504 include but is not limited to whether medical items within the portable medical treatment and guidance apparatus have passed or failed inspections, whether a portable medical treatment and guidance apparatuses has been opened, whether a portable medical treatment and guidance apparatuses has been moved, whether a medical item has been removed from a compartment of the portable medical treatment and guidance apparatus, whether a medical item has expired, and whether a battery needs charging. Furthermore, via this app, the inspector has the ability to manually override and manually enter information. For example, an inspector may swipe one way to pass, other way to fail. In some implementations, the inspector can add details into the app that is synchronized with the database and shared with the other mobile devices of the medical treatment and guidance apparatus management system.

Figure 19B:
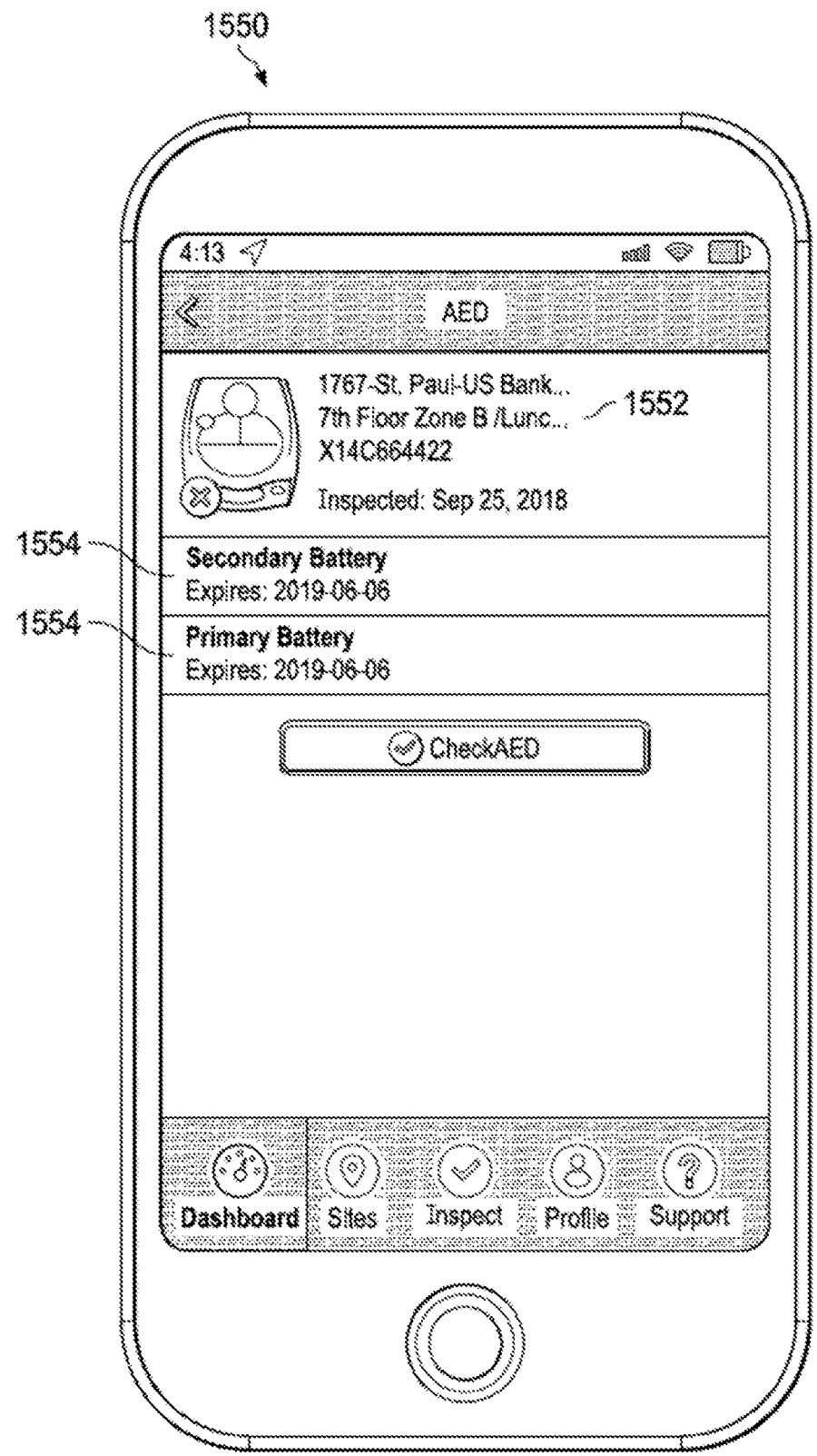

FIG. 19B shows a detailed view of a medical item within the portable medical treatment and guidance apparatus shown in FIG. 19A. Here, the mobile device shows location data 1552 of the medical item and the expiration dates 1554 of the primary and secondary batteries of the medical item.

The app is configured to prompt an inspector if a portable medical treatment and guidance apparatus and/or a medical item within a portable medical treatment and guidance apparatus requires an inspector's attention. For example, a push alert can notify the inspector. In some implementations, an alert is sent to the inspector's mobile device when inventory needs to be replenished (e.g., once the database receives information that a medical item has been used, it requests an alert be sent to the inspector). In some implementations, the database can request an email to be sent by the server 306 requesting a replenishment of such inventory. In some implementations, an alert is sent to the inspector when a battery is not charged or has not been initially charged (i.e., charged within a predetermined time (e.g., 1 day, 2 days) of being initially setup).

In some implementations, an alert is sent if too long has passed since receiving the most recent status update from the portable medical treatment and guidance apparatus (e.g., 2 days or 2 weeks has passed). This alert can instruct the inspector to review the portable medical treatment and guidance apparatus to check that it is connected to the medical treatment and guidance apparatus management system and sufficiently charged.

The app is also configured to show a map of portable medical treatment and guidance apparatuses that have failed inspection or have a negative status that requires immediate attention.

Figure 19C:
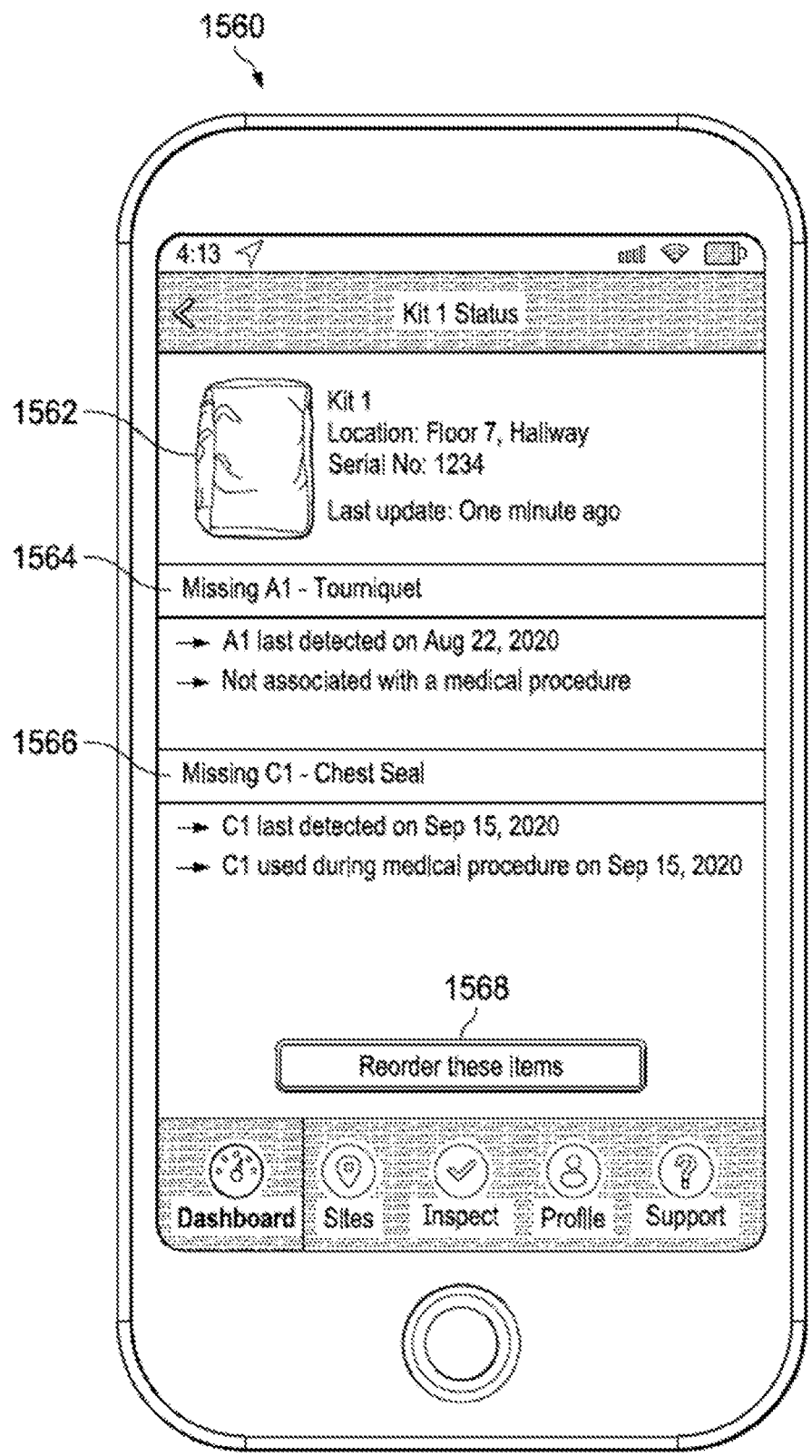

FIG. 19C shows a screenshot 1560 of the app showing a portable medical treatment and guidance apparatus 1562 nicknamed "kit 1" with the last known location, serial number, and time since last update. The app indicates that the A1 Tourniquet 1564 is missing from "kit 1" and provides details that the A1 Tourniquet was last detected (e.g., confirmed via inspector entry, detected by RFID sensors of "kit 1", detected by image processing of a mobile device or server, or inferred from the summary report sent from the mobile device) on Aug. 22, 2020. The app indicates that the missing A1 Tourniquet was not associated with a medical procedure (e.g., the server 306 queried the summary reports associated with "kit 1" for an instance where a Tourniquet was instructed to be used in a medical procedure). Such an indication means that the inspector should physically confirm that the A1 Tourniquet is in fact missing since it may have been stolen or there may be a malfunction with the item and/or portable medical treatment and guidance apparatus.

Similarly, the app shows that the C1 Chest Seal 1566 is also missing from "kit 1" and was last detected on Sep. 15, 2020. The app indicates that the C1 Chest Seal was used in a medical procedure on Sep. 15, 2020. As described above, the server 306 can query the status reports associated with "kit 1" to make this determination. In this scenario, the last detected date corresponds with the date when the C1 Chest Seal was used in a medical procedure.

Figure 19D:
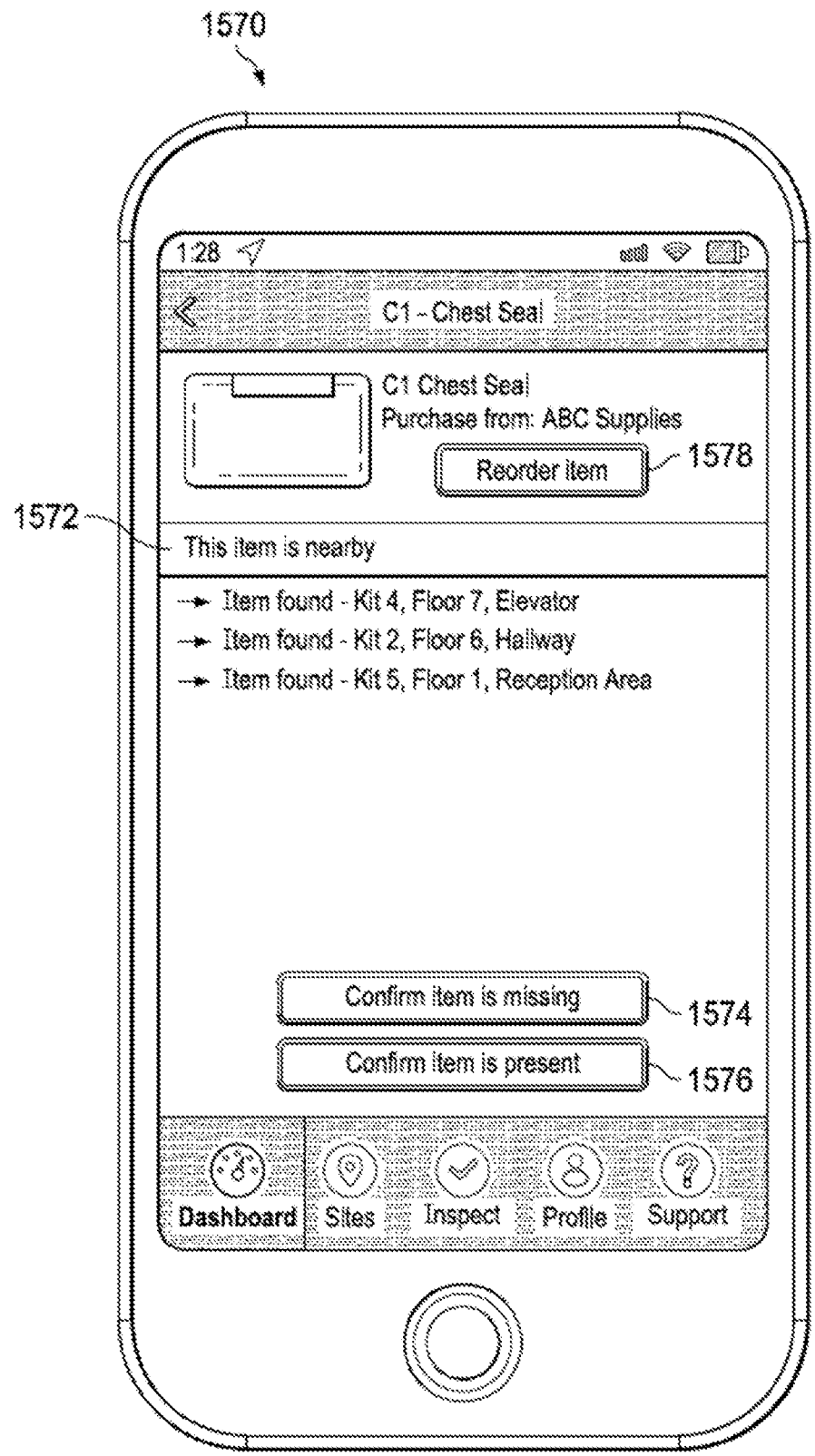

The app also includes a reorder button 1568 to reorder the items shown above, namely the A1 Tourniquet and the C1 Chest Seal. When an inspector clicks the reorder button 1568 a request to reorder one Tourniquet and one Chest Seal is sent to a supplier with a request to deliver the one Tourniquet and the one Chest Seal to the location of "kit 1." In this scenario, the "Floor 7, Hallway" will be printed on the shipping label such that when the package is received by shipping and receiving, they will deliver the items to the approximate location of "kit 1." FIG. 19D shows a screenshot 1570 with additional details of the C1 Chest Seal from FIG. 19C. The additional details can be invoked when a user clicks on the C1 Chest Seal indication shown in FIG. 19C. A reorder button 1578 enables the inspector to reorder this item.

Furthermore, the additional details show that other C1 Chest Seals are nearby 1572. In this scenario, the app indicates that additional C1 Chest Seals can be found in "Kit 4," "Kit 2," and "Kit 5." The respective locations of these kits are also indicated. In some examples, this detail screen indicates all stock of C1 Chest Seals including C1 Chest Seals that are in a stock room. Such information can aid the inspector in determining whether to purchase more or move supplies from other kits if necessary.

The app includes a missing confirmation button 1574 that, when pressed, stores an entry in the database that the item was confirmed missing by the identification of the inspector (e.g., known via a log-in to the app, etc.) on today's date. Similarly, the app includes a present confirmation button 1576 that, when pressed, stores an entry in the database that the item was confirmed present by the identification of the inspector on today's date. Upon pressing either the missing confirmation button 1574 or the present confirmation button 1576, the inspector will be asked to enter any notes to be stored in the database.

FIGS. 20A and 20B show screenshots 1600, 1650 of information displayed on medical treatment and guidance apparatus management devices (e.g., the medical treatment and guidance apparatus management devices 40 as described with reference to FIG. 1 or the computational devices [a second mobile device 308*a*, a laptop computer 308*b*] as described with reference to FIG. 18) for inventory management of one of more portable medical treatment and guidance apparatuses and other electronic devices.

A list 1602 shows portable medical treatment and guidance apparatuses 1604 (e.g., any of the portable medical treatment and guidance apparatuses described herein) along with other electronic devices 1606 (e.g., AEDs, ventilators, or any of the "other devices" 40 as described and shown with reference to FIG. 1 or the electronic devices 1402, 1404, 1406 as described with reference to FIG. 18) within the medical treatment and guidance apparatus management system.

The medical treatment and guidance apparatus management devices may be used to manage, via a communication link 310 (as shown in FIG. 18), a database of inventory information by connecting to a server and accessing the database. The app shown in FIGS. 20A and 20B is similar to the app shown in FIGS. 19A-19D. In some examples, the app shown in FIGS. 19A-19D is intended to be performed by an inspector in a mobile setting (e.g., as the inspector travels to and from each portable medical treatment and guidance apparatus to confirm inventory and check status). Conversely, the app shown in FIGS. 20A and 20B is intended to be performed by an inspector in a non-mobile setting (e.g., from a desk). However, the app shown in FIGS. 20A and 20B can be performed in a mobile setting and the app shown in FIGS. 19A-19D can be performed in a non-mobile setting. In other words, either of these apps or a combination of their features may be performed by an inspector or person managing the inventory from any location as long as access to the database is achieved. Furthermore, any of the information stored in the database may be queried and shown in the list 1602.

In some implementations, each portable medical treatment and guidance apparatus is associated with an image identifier. For example, a stock image can be used in the "Kit" column to indicate whether the kit is the portable medical treatment and guidance apparatus 100, the portable medical treatment and guidance apparatus 102, the portable medical treatment and guidance apparatus 700, the portable medical treatment and guidance apparatus 1000, the portable medical treatment and guidance apparatus 1100, or the portable medical treatment and guidance apparatus 2100. In examples where the "kit" is not one of the portable medical treatment and guidance apparatus, a stock image of another device can be used.

Each portable medical treatment and guidance apparatus includes serial number information (or asset tag) that is a manufacturer-assigned identification number that uniquely identifies the portable medical treatment and guidance apparatus or other device.

Each portable medical treatment and guidance apparatus includes last checked status information that indicates the most recent "check-in" of the portable medical treatment and guidance apparatus. In some scenarios, the last checked status is provided by an inspector actually confirming the status and in other scenarios, the last checked status represents the most recent time when the portable medical treatment and guidance apparatus sent status information to the database automatically (e.g., by querying the RFID tags, by sending a summary report of a use of the portable medical treatment and guidance apparatus etc.). In examples with other devices that include self-diagnostic capabilities (e.g., for AEDs) the last checked date can represent the most recent date a self-diagnostic check was received by the database.

Each portable medical treatment and guidance apparatus includes summary information (or readiness information). The summary information indicates whether the portable medical treatment and guidance apparatus is determined to be ready for use, i.e., ready to be used for a medical emergency. In some scenarios, "ready for use" indicates that the portable medical treatment and guidance apparatus is fully stocked and, when applicable, has a sufficiently charged battery (e.g., above 75% charge). Conversely, a determination that the portable medical treatment and guidance "needs inspection" indicates that the portable medical treatment and guidance apparatus requires inspection. In some scenarios, "needs inspection" indicates that the portable medical treatment and guidance apparatus is missing medical items (e.g., needs replenishment) and/or includes a low battery (e.g., the battery needs to be charged).

However, a portable medical treatment and guidance apparatus with a "needs inspection" indication may, of course, be used during a medical emergency, with the caveat that something is amiss (e.g., missing medical items, low battery). Therefore, in some examples, it is incumbent on the inspector to review the portable medical treatment and guidance apparatuses with a "needs inspection" indication to review whether these portable medical treatment and guidance apparatuses are suitable for use in a medical emergency (e.g., usable but not fully replenished).

Determining whether the portable medical treatment and guidance apparatus is "ready for use" vs. "needs inspection" is a user programmable setting (e.g., via settings within the "Setup" menu) and, in some cases, includes all or some of the following conditions.

The ready for use determination may require that the inventory of the portable medical treatment and guidance apparatus is full (e.g., no medical items are determined to be missing (e.g., inferred via imaging processing, inferred via the status report, or inferred via the RFID tags) or no medical items are confirmed to be missing (e.g., by the inspector manually)).

The ready for use determination may require that each battery associated with the portable medical treatment and guidance apparatus is above a threshold (e.g., above 20%, above 50%, or above 75%). The specific battery level used in determining whether the portable medical treatment and guidance apparatus is ready for us is also user programmable (e.g., via settings within the "Setup" menu). In some examples, the battery is the battery of the mobile devices or tablets 702, 1002 within the portable medical treatment and guidance apparatus.

The ready for use determination may require that the last checked status (e.g., last test data) be within a recent time frame (e.g., within the last 1 month, or within the last 2 months). If the last checked status was received before this time frame, the server determines that the portable medical treatment and guidance apparatus may not be ready for use and flags it (e.g., via the "needs inspection" indication) for an inspector to check on the status manually. For example, in some scenarios, the battery of the mobile device or tablet has died and status updates are no longer received by the database. In other examples, the portable medical treatment and guidance apparatus has moved outside of the network and is no longer able to send status updates. In this scenario, the location of the portable medical treatment and guidance apparatus may be updated to reflect an "Unknown" location 1608.

The ready for use determination may require that a device included in the portable medical treatment and guidance apparatus pass a self-diagnostic check. For example, in scenarios where the portable medical treatment and guidance apparatus includes a device that supports self-checks or self-diagnostic capability (e.g., AEDs), the device may report in the status of the self-diagnostic check and the results may be indicated in the "Summary" column.

In some cases, a treatment and guidance apparatus needing inspection that is "suitable for use" represents a scenario where a portable medical treatment and guidance apparatus needing inspection is usable to treat at least some of the medical emergencies that a ready for use portable medical treatment and guidance apparatus can treat. In some examples, the "suitable for use" determination is made by the inspector and entered into the database (e.g., entered by the inspector via one or more of the portable medical treatment and guidance apparatus management devices described herein and stored in the database via inclusion in the summary information).

In some examples, the "suitable for use" determination is performed by the medical treatment and guidance apparatus management device and included in the database, e.g., via inclusion in the summary information. In some examples, the "suitable for use" indication is presented on the user interfaces of the portable medical treatment and guidance apparatus management devices. In some examples, the ready for use determination is based on the portable medical treatment and guidance apparatus including, one or more of the following conditions: a majority of medical items are present, at least particular medical items are present (e.g., an A1 Tourniquet and a C1 Chest Seal), and/or a battery is low but not empty (e.g., between 25% and 75%), among others).

Each portable medical treatment and guidance apparatus includes location information. The location information may indicate the building identification, a floor, a room, or a hallway location of the portable medical treatment and guidance apparatus or device.

The portable medical treatment and guidance apparatus management system also provides a detailed view with additional information for the inspector. For example, if an inspector selects the portable medical treatment and guidance apparatus 1610 (e.g., by clicking on the image shown in the "Kit" column), the portable medical treatment and guidance apparatus management system changes view to the view shown in FIG. 20B.

FIG. 20B presents an example of a detailed view of the portable medical treatment and guidance apparatus 1610 shown in FIG. 20A. The portable medical treatment and guidance apparatus management system shows a screenshot 1560 that includes current information 1652 that includes the data purchased, the date initialized (e.g., the date the portable medical treatment and guidance apparatus was initially set-up), the last update date (e.g., the date last checked in FIG. 20A), the battery status (if applicable), whether the mobile device or tablet is charging (if applicable), whether the portable medical treatment and guidance apparatus is ready or not (e.g., as shown in the "Summary" column of FIG. 20A). An edit current information button 1654 is provided such that when the edit current information button 1654 is pressed, the information in the current information window 1652 may be modified by the inspector.

The portable medical treatment and guidance apparatus management system includes status information 1656 that presented a chronological order of status information received from the portable medical treatment and guidance apparatus. The status information 1656 also includes manual updates from inspectors. The status information 1656 includes a readiness status in accordance with the determination described with reference to the "Summary" column of FIG. 20A.

The portable medical treatment and guidance apparatus management system includes an inventory snapshot 1658 that includes a list of each part number, part name, group/label identification, color, and quantity of each medical item within the portable medical treatment and guidance apparatus 1610. In some examples, expiration date information is also included in the list. The specific columns shown can be changed via a settings option within the "Setup" menu.

In some implementations, the inventory snapshot 1658 emphases a medical item with a determined quantity that is less than an expected quantity. For example, the expected quantity is configurable when setting up the portable medical treatment and guidance apparatus management system and/or anytime via the application (e.g., via the edit current information button 1654). In the example shown, the "HyFin Chest Seal" shows a quantity of "0" while the portable medical treatment and guidance apparatus 1610 expects a quantity of "1." As a result, the application shows the row emphasized in bold font (but different colors or highlighting may also be used) to direct the inspectors attention to the medical item. Referring back to FIG. 20A, the portable medical treatment and guidance apparatus 1610 shows a "Summary" of "Missing 1 Item" indicative of the missing HyFin Chest Seal. In implementations in which an inspector is in a mobile setting at a portable medical treatment and guidance apparatus to confirm inventory and check status and in which the portable medical treatment and guidance apparatus includes lights associated with its various compartments, the light(s) for a compartment in which the relevant medical item should be located to direct the inspector's attention to that compartment for inspection. The light(s) can color coded to the medical item, as discussed above.

The portable medical treatment and guidance apparatus management system includes a button (or option) to "Reorder Missing Items" 1662 that transmits a request to purchase 1 HyFin Chest Seal from a supplier. In some examples, the portable medical treatment and guidance apparatus management system can be configured to request the medical item be shipped to the location of the portable medical treatment and guidance apparatus itself.

In some implementations, the portable medical treatment and guidance apparatus management system includes a button (or option) to generate a record (not shown) to generate a report of the missing medical items that is then stored in the database for querying by the devices of the portable medical treatment and guidance apparatus management system. In some implementations, the portable medical treatment and guidance apparatus management system includes a button (or option) to provide a notification to an inspector (e.g., via a mobile phone) so that the inspector is notified to confirm whether the medical item needs to be replenished or if the notification can be dismissed (i.e., the medical item does not need to be replenished).

The portable medical treatment and guidance apparatus management system includes a button (or option) to "Delete this Record" 1664 that removes specific columns from the list.

The portable medical treatment and guidance apparatus management system includes a button (or option) to "Dispatch Inspector" 1666 that transmits a request to inspectors within the network or inspectors within a radius to the portable medical treatment and guidance apparatus 1610 to check on the status of the portable medical treatment and guidance apparatus 1610. Along with the dispatch request, the portable medical treatment and guidance apparatus management system sends details about the missing items so the inspector is aware what he/she is expected to confirm.

The portable medical treatment and guidance apparatus management system includes a button (or option) to "Modify Status" 1668 that edits specific columns within the list. For example, if one or more details within the table is wrong, the details can be edited using this option.

The portable medical treatment and guidance apparatus management system includes a button (or option) to "Remove Kit from List" 1670 that removes the entire portable medical treatment and guidance apparatus 1610 from the portable medical treatment and guidance apparatus management system.

FIGS. 21A and 21B show a map 1700, 1750 of a building 1702 that includes three portable medical treatment and guidance apparatuses "A" 1704, "B" 1706, and "C" 1708. The location and readiness of each of the portable medical treatment and guidance apparatuses are communicated to the server and the database. Suppose a patient 1710 is in need of a tourniquet during an emergency. A caregiver may approach portable medical treatment and guidance apparatus "B" 1706 since it is the closest to the patient 1710, but instead the caregiver opens an application on his/her mobile device 1712 and indicates to the application that a tourniquet is needed for treatment. The application communicates with the server and the database and determines that portable medical treatment and guidance apparatuses "A" 1704 and "C" 1708 have a tourniquet ready. This is shown by the checkmarks 1752 on the map in FIG. 21B. Conversely, portable medical treatment and guidance apparatus "B" does not have a tourniquet and is therefore needs to be inspected by the inspector as shown by the 'x' marker 1754. In some implementations, a caution marker may be used to denote partial issues (e.g., some unrelated inventory missing, unknown status, etc.).

Additionally, the caregiver does not need to down filter by tourniquets, and instead can view ready portable medical treatment and guidance apparatuses nearby. In this situation, the database will be queried to determine portable medical treatment and guidance apparatuses with complete inventory with no expired medical items. Directions to the closest portable medical treatment and guidance apparatus may be provided to the caregiver visually (e.g., on the screen of the mobile device 1712) or audibly (e.g., via a speaker of the mobile device 1712).

In some implementations, the mobile device 1712 is configured to search for a nearby spare of the at least one medical item. In some implementations, the mobile device 1712 is configured to present via the user interface a map of the portable medical treatment and guidance apparatus and a distance of the portable medical treatment and guidance apparatus relative to a current position of the mobile device 1712. The map indicates whether the portable medical treatment and guidance apparatus is missing the at least one medical item.

Knowledge of all nearby ready portable medical treatment and guidance apparatuses is helpful for caregivers to know since it reduces wasted time while administering medical treatment. In addition, when using the application, the caregiver can signal to first responders where the medical treatment is taking place.

As discussed above, a device such as a mobile device or a tablet device can run an application useful for inventory management and for providing instructions to a caregiver for administering medical treatment using a medical treatment and guidance apparatus. In some implementations, the device will have the app pre-installed thereon and be ready for use before the need arises for a caregiver to administer medical treatment using the medical treatment and guidance apparatus. The app may thus be executed/run on the device when the need arises for a caregiver to administer medical treatment using the medical treatment and guidance apparatus without the app first needing to be installed on the device. The app on the device may be pre-associated with the medical treatment and guidance apparatus, such as by being presentable on a list of selectable medical treatment and guidance apparatuses, similar to the list 1602 of FIG. 20A discussed above, that the caregiver can select when running the app, so as to be ready for use with the medical treatment and guidance apparatus. Selecting the particular medical treatment and guidance apparatus that the caregiver desires to use with a victim/patient may facilitate inventory management and/or providing instruction for particular medical items in the medical treatment and guidance apparatus, as discussed herein.

For example, certain caregivers may be medical practitioners such as emergency medical technicians (EMTs), paramedics, doctors, nurses, and other medical professionals. Such a caregiver may have the app installed and ready for use on their mobile device, which may be a personal device or an employer-provided device, in anticipation of the app's potential future use in the course of the caregiver's work. Being a known medical treatment and guidance apparatus accessible to the caregiver during the course of the caregiver's work, the medical treatment and guidance apparatus may be pre-associated with the app installed on the device. For another example, certain caregivers may be employees at a facility (e.g., a hospital, a clinic, or other medical facility; a university or other school; a corporate office; a government building; etc.) at which the medical treatment and guidance apparatus is stored and made available for use. Such caregivers may or may not be medical professionals but may need to use the medical treatment and guidance apparatus in an emergency situation. Such a caregiver may have the app installed and ready for use on their device, which may be a personal device or an employer-provided device, either voluntarily or as suggested or required by the employer, in anticipation of the app's potential future use while the caregiver is at work. Being a known medical treatment and guidance apparatus accessible to the caregiver at the facility, the medical treatment and guidance apparatus may be pre-associated with the app installed on the device. For yet another example, a medical treatment and guidance apparatus can include a removable tablet device, such as the portable medical treatment and guidance apparatus 700 with removable tablet device 702 discussed above. The removable tablet device can have the app pre-installed thereon since the tablet device is known to be used with the medical treatment and guidance apparatus with which it is included.

In some implementations, the device will not have the app pre-installed thereon before the need arises for a caregiver to administer medical treatment using the medical treatment and guidance apparatus. The app thus cannot be executed/run on the device when the need arises for a caregiver to administer medical treatment using the medical treatment and guidance apparatus without the app first being installed on the device. Installing the app on the device will take time that could otherwise be used for the caregiver to provide care to the victim/patient, which is a delay that may adversely affect the victim's/patient's outcome. Installing the app on the device may involve the caregiver using the device to navigate to an app store or other site that has the app available and download the app from the app store or other site to be installed on the device. To complete installation, the caregiver may need to register an account associated with the app before the app can be used on the device and/or may need to associate the app with the particular medical treatment and guidance apparatus that the caregiver desires to use on a victim/patient. In some instances, a caregiver may forgo installing the app in favor of saving time and more quickly treating the victim/patient, which may result in improper use of medical item(s) in the medical treatment and guidance apparatus, may result in not using medical item(s) in the medical treatment and guidance apparatus at all or at the proper time during medical treatment, and/or may result in inefficient inventory management.

For example, certain caregivers may be at a facility, such as by being a student at school, a visitor to a building, etc., but generally not expect to encounter an emergency situation in which their use of the medical treatment and guidance apparatus is needed and thus not have the app pre-installed on their device. For another example, a caregiver may expect to use a medical treatment and guidance apparatus's removable tablet device and thus not have the app pre-installed on another device, such as the caregiver's mobile phone. In the event that the removable tablet device cannot be used, such as due to low battery, broken screen, etc., the caregiver may need to use another device that does not have the app pre-installed thereon.

In some implementations, a medical treatment and guidance apparatus can include an identifying feature (e.g., QR code, UPC barcode, etc.) associated with the medical treatment and guidance apparatus and configured to facilitate use of an app with the medical treatment and guidance apparatus when the app has not been pre-installed on a caregiver's device. The identifying feature can be on the medical treatment and guidance apparatus, such as being on an exterior surface thereof or on an interior surface thereof, so as to be easily noticeable by and accessible to a caregiver accessing the medical treatment and guidance apparatus even if the caregiver does not have previous experience with the medical treatment and guidance apparatus. The identifying feature being on an interior surface thereof, such as on an interior surface of a lid or other portion of the medical treatment and guidance apparatus, may provide security by only providing access to the identifying feature upon opening of the medical treatment and guidance apparatus.

Using at least one camera and/or reader of the device, the caregiver can capture an image of or otherwise read the identifying feature to provide the device with access to the app. The access to the app can be a download of the app to the device such that the app runs on the device or browser direction to a website providing online functionality of the app. Downloading the app to the device may facilitate usability since many caregivers will be familiar with using apps on the device and/or may eliminate a provider or other administrator of the medical treatment and guidance apparatus needing to maintain a website providing emergency app access. Using a website allows the device to be used by the caregiver in conjunction with use of the medical treatment and guidance apparatus without the app needing to be installed on the device, which may save time during medical treatment and/or may end access to the app upon closing of the browser so as to facilitate the caregiver's one-time emergency use of the app.

The identifying feature can be unique to the medical treatment and guidance apparatus. In this way, the medical treatment and guidance apparatus can be uniquely identified by reading the identifying feature.

FIG. 22 shows a flowchart 1900 of a computer-implemented method for downloading an app to a device using an identifying feature associated with a medical treatment and guidance apparatus, such as any of the portable medical treatment and guidance apparatuses 100, 700, 1000, 1100, 2100 previously described. The method is performed by a processor of the device, and/or a server such as a server 60, 306 previously described.

The device reads 1902 an identifying feature of the medical treatment and guidance apparatus, e.g., using a camera or reader of the device. Reading 1902 the identifying feature automatically directs 1904 the device, e.g., a browser thereof, to a site allowing download of the application. The site can be, for example, a page for the application at an online app store, a website maintained by a provider of the medical treatment and guidance apparatus, or other site. The device can then download and install 1906 the application from the site. In some implementations, the download begins automatically, which may save time in an emergency situation. In other implementations, a user of the device provides an input, e.g., touchscreen input, button press, etc., to the device to begin the download and installation 1906 of the application, which may allow for confirmation that the website was not accessed accidentally.

As discussed herein, uniquely identifying the medical treatment and guidance apparatus may facilitate inventory management and/or providing instruction for particular medical items in the medical treatment and guidance apparatus. For example, as discussed above, uniquely identifying the medical treatment and guidance apparatus may allow for determination of which groups of medical items are present in the medical treatment and guidance apparatus. For another example, as also discussed above, uniquely identifying the medical treatment and guidance apparatus may allow for determination of the inventory for the particular portable medical treatment and guidance apparatus.

In some implementations, the medical treatment and guidance apparatus can be uniquely identified by the reading 1902 of the identifying feature, such as by a QR code, UPC barcode, etc. providing unique identification information for the medical treatment and guidance apparatus. In such instances, the installed application can run 1910 with the identity of the medical treatment and guidance apparatus being known 1908. In other implementations, the medical treatment and guidance apparatus will not be uniquely identified by the reading 1902 of the identifying feature. The device, however, can have a known 1912 device identifier. One example of such a device identifier, as shown in the implementation of FIG. 22, is an IP address. IP addresses are associated with particular geographic locations, so the known 1912 IP address can be associated with a particular geographic location. Particular medical treatment and guidance apparatuses are associated with particular geographic locations based on the medical treatment and guide apparatus's current location. The known 1912 IP address may therefore be able to be associated 1914 with a particular medical treatment and guide apparatus if the location of a single medical treatment and guidance apparatus matches the location of the known 1912 IP address. The association 1914 can be performed, for example, by the server, such as the server providing the app for download, configured to access a database or lookup table associating each of a plurality of medical treatment and guide apparatuses with geographic locations. If the known 1912 IP address is associated 1914 with a particular medical treatment and guide apparatus, then the application can run 1910 on the device with the identity of the medical treatment and guidance apparatus being known. If the IP address is not known 1912 or if the known 1912 IP address is not associated 1914 with a particular medical treatment and guide apparatus, the device via the app can provide 1916 a list of medical treatment and guide apparatuses, similar to the list 1602 of FIG. 20A discussed above, to allow a user of the device to select the one of the apparatuses that the user has available for use (the apparatus from which the identifying feature was read 1902). The list may be provided 1916 based on the IP address, if known 1912, such that only medical treatment and guide apparatuses within a certain distance of the known geographic location are provided 1916 in the list. Upon receipt 1918 of the user's selection, the application can run 1910 on the device with the identity of the medical treatment and guidance apparatus being known.

The application can be installed on the device until a user of the device uninstalls the application. Alternatively, the application can be installed on the device on a temporary basis not under the control of the user of the device. The caregiver did not already have the app installed on the device and is therefore likely using the medical treatment and guide apparatus, and thus the app, in an emergency situation and is unlikely to need to use the medical treatment and guide apparatus after this one use. The app may therefore be uninstalled from the device to avoid unnecessary memory usage of the device and/or to avoid unintentional subsequent use of the app that may interfere with inventory management of the medical treatment and guide apparatus.

In response to the application starting to run 1910 on the device, a counter, e.g., a timer, a clock, etc., on the device and/or provided by the app can start 1918 counting time. In response to a predetermined amount of time having elapsed 1920, and measured by the counter, the application can be automatically uninstalled 1922 from the device. In some implementations, the device's user can be prompted to acknowledge with an input the application's uninstallation 1922 before the uninstallation begins. The predetermined amount of time can vary but, in general, is an amount of time longer than the medical treatment and guide apparatus would expected to be used with a victim/patient so that the app is not uninstalled 1922 before the caregiver has completed use of the medical treatment and guide apparatus with the victim/patient. Before the application is uninstalled 1922, a record (or case report) of medical instructions that had been presented on the device during use for administering medical treatment is preferably communicated to a database (e.g., via the server 60 of FIG. 1) and used by a management system (e.g., the management system 10 of FIG. 1) for updating inventory status of the portable medical treatment and guidance apparatus and taking action (e.g., reordering medical items, notifying inspectors to confirm usage, etc. as described with reference to FIG. 1 above).

In other implementations, instead of starting 1918 the counter in response to the application starting to run 1910 on the device, the device, e.g., via the app, can begin, in response to the application starting to run 1910 on the device, monitoring whether the app has been closed 1924. The app being closed 1924 is indicative of the caregiver completing use of the medical treatment and guide apparatus with the victim/patient. However, in some instances, the app may have been closed 1924 accidentally or prematurely and may again need to be used by the caregiver. Thus, in response to the app having been closed 1924, a counter, e.g., a timer, a clock, etc., on the device and/or provided by the app can start 1926 counting time. In response to a predetermined amount of time having elapsed 1928, and measured by the counter, the application can be automatically uninstalled 1930 from the device. The predetermined amount of time can vary but, in general, is an amount of time longer than the medical treatment and guide apparatus would expected to be used with a victim/patient so that the app is not uninstalled 1922 before the caregiver has completed use of the medical treatment and guide apparatus with the victim/patient. If the app is re-opened 1932 before the predetermined amount of time has elapsed 1928, the device, e.g., via the app, can again begin monitoring whether the app has been closed 1924.

FIG. 23 shows a flowchart 2000 of a method for providing online functionality of an app using an identifying feature associated with a medical treatment and guidance apparatus, such as any of the portable medical treatment and guidance apparatuses 100, 700, 1000, 1100, 2100 previously described. The method is performed by a processor of the device, and/or a server such as a server 60, 306 previously described. The method is similar to the method of FIG. 22 except that an app is run online, e.g., on a website, instead of on a device to which an app is downloaded.

The device reads 2002 an identifying feature of the medical treatment and guidance apparatus, e.g., using a camera or reader of the device. Reading 2002 the identifying feature automatically directs 2004 the device, e.g., a browser thereof, to a website providing online functionality of the app.

In some implementations, the medical treatment and guidance apparatus can be uniquely identified by the reading 2002 of the identifying feature, such as by a QR code, UPC barcode, etc. providing unique identification information for the medical treatment and guidance apparatus. In such instances, the website can provide instruction and/or perform inventory management functions with the identity of the medical treatment and guidance apparatus being known 2006. In other implementations, the medical treatment and guidance apparatus will not be uniquely identified by the reading 2002 of the identifying feature. A device identifier, such as the device's IP address may, however, be known 2008. Similar to that discussed above regarding the method 1900 of FIG. 22, the known 1912 IP address may be able to be associated 2010 with a particular medical treatment and guide apparatus such that the application can run 2012 on the website (or the website can provide the app's functionality without running the app as it would be installed on a mobile device or tablet device) with the identity of the medical treatment and guidance apparatus being known. Alternatively, also similar to that discussed above regarding the method 1900 of FIG. 22, if the IP address is not known 2008 or if the known 2008 IP address is not associated 2010 with a particular medical treatment and guide apparatus, the website can provide 2014 a list of medical treatment and guide apparatuses to allow a user of the device to select the one of the apparatuses that the user has available for use (the apparatus from which the identifying feature was read 2002). The list may be provided 2014 based on the IP address, if known 2008, such that only medical treatment and guide apparatuses within a certain distance of the known geographic location are provided 2014 in the list. Upon receipt 2016 of the user's selection, the website can provide 2012 online functionality of an app with the identity of the medical treatment and guidance apparatus being known.

The website can remain open on the device, e.g., on the browser thereof, until a user of the device closes the website (which may include closing the browser entirely). Alternatively, the website can remain open on the device on a limited time basis not under the control of the user of the device. The caregiver did not already have the app installed on the device and is therefore likely using the medical treatment and guide apparatus, and thus the website, in an emergency situation and is unlikely to need to use the medical treatment and guide apparatus after this one use. The website may therefore be closed to avoid unnecessary memory usage of the device and/or to avoid unintentional subsequent use of the website that may interfere with inventory management of the medical treatment and guide apparatus.

In response to the website starting to run 2012 the application, a counter, e.g., a timer, a clock, etc., on the server providing the website can start 2014 counting time. In response to a predetermined amount of time having elapsed 2016, and measured by the counter, the website can be automatically closed 2018 on the device, e.g., closing a browser tab in which the website was open, stopping access to the app's functionality on the website and providing notice of ended access on the page, etc. In some implementations, the device's user can be prompted to acknowledge with an input the website's closing 2018 before the uninstallation begins. The predetermined amount of time can vary but, in general, is an amount of time longer than the medical treatment and guide apparatus would expected to be used with a victim/patient so that the website is not closed 2018 before the caregiver has completed use of the medical treatment and guide apparatus with the victim/patient.

FIG. 24 shows an example of example computing device 1800 and example mobile computing device 1850 which can be used to implement the techniques previously described. Computing device 1800 is intended to represent various forms of digital computers, including, e.g., laptops, desktops, workstations, personal digital assistants, servers, blade servers, mainframes, and other appropriate computers. Computing device 1850 is intended to represent various forms of mobile devices, including, e.g., personal digital assistants, tablet computing devices, cellular telephones, smartphones, and other similar computing devices. The components shown here, their connections and relationships, and their functions, are meant to be examples only, and are not meant to limit implementations of the techniques described and/or claimed in this document.

Computing device 1800 includes processor 1802, memory 1804, storage device 1806, high-speed interface 1808 connecting to memory 1804 and high-speed expansion ports 1810, and low speed interface 1820 connecting to low speed bus 1814 and storage device 1806. Each of components 1802, 1804, 1806, 1808, 1810, and 1820 are interconnected using various busses and can be mounted on a common motherboard or in other manners as appropriate.

Processor 1802 can process instructions for execution within computing device 1800, including instructions stored in memory 1804 or on storage device 1806 to display graphical data for a GUI on an external input/output device, including, e.g., display 1816 coupled to high speed interface 1808. In other implementations, multiple processors and/or multiple busses can be used, as appropriate, along with multiple memories and types of memory. Also, multiple computing devices 1800 can be connected, with each device providing portions of the necessary operations (e.g., as a server bank, a group of blade servers, or a multi-processor system).

Memory 1804 stores data within computing device 1800. In one implementation, memory 1804 is a volatile memory unit or units. In another implementation, memory 1804 is a non-volatile memory unit or units. Memory 1804 also can be another form of computer-readable medium (e.g., a magnetic or optical disk). Memory 1804 may be non-transitory.

Storage device 1806 is capable of providing mass storage for computing device 1800. In one implementation, storage device 1806 can be or contain a computer-readable medium (e.g., a floppy disk device, a hard disk device, an optical disk device, or a tape device, a flash memory or other similar solid state memory device, or an array of devices, such as devices in a storage area network or other configurations.) A computer program product can be tangibly embodied in a data carrier. The computer program product also can contain instructions that, when executed, perform one or more methods (e.g., those described above.) The data carrier is a computer- or machine-readable medium, (e.g., memory 1804, storage device 1806, memory on processor 1802, and the like.)

High-speed controller 1808 manages bandwidth-intensive operations for computing device 1800, while low speed controller 1820 manages lower bandwidth-intensive operations. Such allocation of functions is an example only. In one implementation, high-speed controller 1808 is coupled to memory 1804, display 1816 (e.g., through a graphics processor or accelerator), and to high-speed expansion ports 1810, which can accept various expansion cards (not shown). In the implementation, low-speed controller 1820 is coupled to storage device 1806 and low-speed expansion port 1814. The low-speed expansion port, which can include various communication ports (e.g., USB, Bluetooth®, Ethernet, wireless Ethernet), can be coupled to one or more input/output devices, (e.g., a keyboard, a pointing device, a scanner, or a networking device including a switch or router, e.g., through a network adapter.)

Computing device 1800 can be implemented in a number of different forms, as shown in the FIG. 24. For example, it can be implemented as standard server 1820, or multiple times in a group of such servers. It also can be implemented as part of rack server system 1824. In addition or as an alternative, it can be implemented in a personal computer (e.g., laptop computer 1822). In some examples, components from computing device 1800 can be combined with other components in a mobile device (not shown), e.g., device 1850. Each of such devices can contain one or more of computing device 1800, 1850, and an entire system can be made up of multiple computing devices 1800, 1850 communicating with each other.

Computing device 1850 includes processor 1852, memory 1864, an input/output device (e.g., display 1854, communication interface 1866, and transceiver 1868) among other components. Device 1850 also can be provided with a storage device, (e.g., a microdrive or other device) to provide additional storage. Each of components 1850, 1852, 1864, 1854, 1866, 1868 are interconnected using various buses, and several of the components can be mounted on a common motherboard or in other manners as appropriate.

Processor 1852 can execute instructions within computing device 1850, including instructions stored in memory 1864. The processor 1852 can be implemented as a chipset of chips that include separate and multiple analog and digital processors. The processor 1852 can provide, for example, for coordination of the other components of device 1850, e.g., control of user interfaces, applications run by device 1850, and wireless communication by device 1850.

Processor 1852 can communicate with a user through control interface 1858 and display interface coupled to display 1854. Display 1854 can be, for example, a TFT LCD (Thin-Film-Transistor Liquid Crystal Display) or an OLED (Organic Light Emitting Diode) display, or other appropriate display technology. Display interface can comprise appropriate circuitry for driving display 1854 to present graphical and other data to a user. Control interface 1858 can receive commands from a user and convert them for submission to processor 1852. In addition, external interface 1862 can communicate with processor 1852, so as to enable near area communication of device 1850 with other devices. External interface 1862 can provide, for example, for wired communication in some implementations, or for wireless communication in other implementations, and multiple interfaces also can be used.

Memory 1864 stores data within computing device 1850. Memory 1864 can be implemented as one or more of a computer-readable medium or media, a volatile memory unit or units, or a non-volatile memory unit or units. Expansion memory 1874 also can be provided and connected to device 1850 through expansion interface 1872, which can include, for example, a SIMM (Single In Line Memory Module) card interface. Such expansion memory 1874 can provide extra storage space for device 1850, or also can store applications or other data for device 1850. Specifically, expansion memory 1874 can include instructions to carry out or supplement the processes described above, and can include secure data also. Thus, for example, expansion memory 1874 can be provided as a security module for device 1850, and can be programmed with instructions that permit secure use of device 1850. In addition, secure applications can be provided through the SIMM cards, along with additional data, (e.g., placing identifying data on the SIMM card in a non-hackable manner.)

The memory can include, for example, flash memory and/or NVRAM memory, as discussed below. In one implementation, a computer program product is tangibly embodied in a data carrier. The computer program product contains instructions that, when executed, perform one or more methods, e.g., those described above. The data carrier is a computer- or machine-readable medium (e.g., memory 1864, expansion memory 1874, and/or memory on processor 1852), which can be received, for example, over transceiver 1868 or external interface 1862.

Device 1850 can communicate wirelessly through communication interface 1866, which can include digital signal processing circuitry where necessary. Communication interface 1866 can provide for communications under various modes or protocols (e.g., GSM voice calls, SMS, EMS, or MMS messaging, CDMA, TDMA, PDC, WCDMA, CDMA1800, or GPRS, among others.) Such communication can occur, for example, through radio-frequency transceiver 1868. In addition, short-range communication can occur, e.g., using a Bluetooth®, WiFi, or other such transceiver (not shown). In addition, GPS (Global Positioning System) receiver module 1870 can provide additional navigation- and location-related wireless data to device 1850, which can be used as appropriate by applications running on device 1850. Sensors and modules such as cameras, microphones, compasses, accelerators (for orientation sensing), etc. may be included in the device.

Device 1850 also can communicate audibly using audio codec 1860, which can receive spoken data from a user and convert it to usable digital data. Audio codec 1860 can likewise generate audible sound for a user, (e.g., through a speaker in a handset of device 1850). Such sound can include sound from voice telephone calls, can include recorded sound (e.g., voice messages, music files, and the like) and also can include sound generated by applications operating on device 1850.

Computing device 1850 can be implemented in a number of different forms, as shown in the FIG. 24. For example, it can be implemented as cellular telephone 1880. It also can be implemented as part of smartphone 1882, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor. The programmable processor can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to a computer program product, apparatus and/or device (e.g., magnetic discs, optical disks, memory, Programmable Logic Devices (PLDs)) used to provide machine instructions and/or data to a programmable processor, including a machine-readable medium that receives machine instructions.

To provide for interaction with a user, the systems and techniques described here can be implemented on a computer having a device for displaying data to the user (e.g., a CRT (cathode ray tube) or LCD (liquid crystal display) monitor), and a keyboard and a pointing device (e.g., a mouse or a trackball) by which the user can provide input to the computer. Other kinds of devices can be used to provide for interaction with a user as well; for example, feedback provided to the user can be a form of sensory feedback (e.g., visual feedback, auditory feedback, or tactile feedback); and input from the user can be received in a form, including acoustic, speech, or tactile input.

The systems and techniques described here can be implemented in a computing system that includes a backend component (e.g., as a data server), or that includes a middleware component (e.g., an application server), or that includes a frontend component (e.g., a client computer having a user interface or a Web browser through which a user can interact with an implementation of the systems and techniques described here), or a combination of such back end, middleware, or frontend components. The components of the system can be interconnected by a form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

While the inventive features described herein have been described in terms of a preferred embodiment for achieving the objectives, it will be appreciated by those skilled in the art that variations may be accomplished in view of these teachings without deviating from the spirit or scope of the present disclosure.

What is claimed is:

1. A portable medical treatment and guidance apparatus for assisting a user in treating a patient, the apparatus comprising:
   a housing having at least one compartment;
   a plurality of medical supplies housed within the at least one compartment;
   a user interface configured to provide an interactive query flow for assisting the user in providing medical treatment;
   at least one sensor adapted to detect removal of at least one medical item of the plurality of medical supplies; and
   at least one processor and memory mechanically coupled to the housing and communicatively coupled to the user interface, the at least one sensor, and communications circuitry, the at least one processor and memory configured to:
      present via the user interface at least one inquiry as part of the interactive query flow,
      receive at least one user input via the user interface in response to the at least one inquiry,
      present via the user interface instructions for administering medical treatment based on the at least one user input,
      determine whether the at least one sensor has detected removal of the at least one medical item, and
      transmit an output signal based on the detected removal of the at least one medical item to provide a status indication regarding the portable medical treatment and guidance apparatus;
   wherein the at least one processor and memory are further configured to receive a self-diagnostic signal indicating that a self-diagnostic test of the at least one medical item is required, wherein the self-diagnostic test comprises ensuring a battery level of the at least one medical item is above a threshold, ensuring an expiration date of the at least one medical item has not occurred, and ensuring the at least one medical item is present in the portable medical treatment and guidance apparatus.

2. The portable medical treatment and guidance apparatus of claim 1, wherein the at least one processor and memory are further configured to present via the user interface instructions for administering medical treatment based on the detected removal of the at least one medical item.

3. The portable medical treatment and guidance apparatus of claim 1, wherein the instructions for administering medical treatment involve one or more steps for using the at least one medical item.

4. The portable medical treatment and guidance apparatus of claim 1, wherein the status indication regarding the portable medical treatment and guidance apparatus identifies an inventory of the plurality of medical supplies.

5. The portable medical treatment and guidance apparatus of claim 1, wherein the status indication regarding the portable medical treatment and guidance apparatus identifies an expiration date of the plurality of medical supplies.

6. The portable medical treatment and guidance apparatus of claim 1, wherein the at least one processor and memory are further configured to receive the instructions from the at least one medical item.

7. The portable medical treatment and guidance apparatus of claim 1, wherein the at least one processor and memory are further configured to control an operation of the at least one medical item.

8. The portable medical treatment and guidance apparatus of claim 1, wherein the at least one processor and memory are further configured to receive remote control information regarding remote control of an operation of the at least one medical item.

9. The portable medical treatment and guidance apparatus of claim 1, wherein the at least one processor and memory are further configured to receive a status indication regarding the at least one medical item.

10. The portable medical treatment and guidance apparatus of claim 1, wherein the at least one processor and memory are further configured to transmit a status indication regarding the at least one medical item.

11. The portable medical treatment and guidance apparatus of claim 10, wherein the status indication regarding the at least one medical item identifies a readiness status of whether the at least one medical item is ready to be used in an emergency.

12. The portable medical treatment and guidance apparatus of claim 10, wherein the status indication regarding the at least one medical item identifies a battery charge level of a battery of the at least one medical item.

13. The portable medical treatment and guidance apparatus of claim 10, wherein the status indication regarding the at least one medical item identifies an expiration date of the at least one medical item.

14. The portable medical treatment and guidance apparatus of claim 1, wherein the at least one processor and memory are further configured to determine when a self-diagnostic test of the at least one medical item is required.

15. The portable medical treatment and guidance apparatus of claim 1, wherein the at least one processor and memory are further configured to transmit a self-diagnostic signal to the at least one medical item to initiate a self-diagnostic test of the at least one medical item.

16. The portable medical treatment and guidance apparatus of claim 1, wherein the at least one processor and memory are further configured to present instructions to use a spare at least one medical item to replace a functionality of the at least one medical item that has failed a self-diagnostic test.

17. The portable medical treatment and guidance apparatus of claim 1, wherein the at least one processor and memory are further configured to search for a nearby spare at least one medical item matching a functionality of the at least one medical item.

18. The portable medical treatment and guidance apparatus of claim 1, wherein presenting via the user interface comprises displaying the instructions on a display integrated into the housing.

19. The portable medical treatment and guidance apparatus of claim 1, wherein presenting via the user interface comprises verbalizing the instructions using a speaker integrated into the housing.

20. The portable medical treatment and guidance apparatus of claim 1, further comprising a near-field communication device configured to communicate with an external device, wherein the near-field communication device is configured to transmit the status indication regarding the portable medical treatment and guidance apparatus to a nearby mobile device.

21. The portable medical treatment and guidance apparatus of claim 1, wherein the at least one sensor is a radio frequency identification (RFID) reader and is configured to receive an RFID signal from the at least one medical item.

22. The portable medical treatment and guidance apparatus of claim 1, wherein the at least one sensor is an optical sensor.

23. The portable medical treatment and guidance apparatus of claim 1, wherein the at least one processor and memory are further configured to determine when a component of the at least one medical item is missing based on a result of a self-diagnostic test and the at least one sensor.

24. The portable medical treatment and guidance apparatus of claim 17, wherein the at least one processor and memory are further configured to determine whether the nearby spare at least one medical item is ready for use; and
the at least one processor and memory are further configured to present a notification that the nearby spare at least one medical item is nearby and ready for use.

25. The portable medical treatment and guidance apparatus of claim 17, wherein the at least one processor and memory are further configured to present directions for navigating to the nearby spare at least one medical item.

26. The portable medical treatment and guidance apparatus of claim 1, wherein the at least one processor and memory are further configured to determine when a component of the at least one medical item has failed a self-diagnostic test based on a result of the self-diagnostic test;
the at least one processor and memory are further configured to determine identifying information of the component of the at least one medical item that has failed the self-diagnostic test; and
the at least one processor and memory are further configured to present the determined identifying information of the component to the user interface.

27. The portable medical treatment and guidance apparatus of claim 1, wherein the at least one processor and memory are further configured to determine when a component of the at least one medical item has failed a self-diagnostic test based on a result of the self-diagnostic test;
the at least one processor and memory are further configured to determine identifying information of the component of the at least one medical item that has failed the self-diagnostic test; and
the at least one processor and memory are further configured to present repair instructions for the component to the user interface.

28. The portable medical treatment and guidance apparatus of claim 1, further comprising an indicator configured to alert a user that the at least one medical item has failed a self-diagnostic test and needs servicing.

29. The portable medical treatment and guidance apparatus of claim 1, wherein the at least one processor and memory are further configured to determine when a component of the at least one medical item has passed a self-diagnostic test based on a result of the self-diagnostic test.

30. The portable medical treatment and guidance apparatus of claim 1, further comprising an indicator configured to notify a user when the at least one medical item has passed a self-diagnostic test and is ready for use.

31. The portable medical treatment and guidance apparatus of claim 21, each of the at least one compartments has at least one light associated therewith; and
in response to the interactive query flow indicating that the at least one medical item should be removed from the portable medical treatment and guidance apparatus, the light associated with the compartment in which the at least one medical item is located illuminates.

32. The portable medical treatment and guidance apparatus of claim 31, wherein the at least one medical item that is removed is reusable; and
in response to the interactive query flow indicating that the at least one medical item that is reusable should be returned to the portable medical treatment and guidance apparatus, the light associated with the compartment in which the at least one medical item should be located illuminates.

33. The portable medical treatment and guidance apparatus of claim 1, wherein the plurality of medical supplies comprise electrodes for electrotherapy treatment.

34. The portable medical treatment and guidance apparatus of claim 1, wherein the plurality of medical supplies comprise a resuscitation treatment protocol corresponding to electrotherapy treatment.

* * * * *